United States Patent
Wang et al.

(10) Patent No.: US 11,884,961 B2
(45) Date of Patent: Jan. 30, 2024

(54) DNA-GLYCAN CONJUGATES AND METHODS OF USE

(71) Applicant: GEORGIA STATE UNIVERSITY RESEARCH FOUNDATION, INC., Atlanta, GA (US)

(72) Inventors: Peng George Wang, Johns Creek, GA (US); Jing Song, Johns Creek, GA (US); Muhammed Shukkoor Kondengaden, Kerala (IN); Aishwarya Parameswaran, Perungalatur (IN)

(73) Assignee: GEORGIA STATE UNIVERSITY RESEARCH FOUNDATION, INC., Atlanta, GA (US)

( * ) Notice: Subject to any disclaimer, the term of this patent is extended or adjusted under 35 U.S.C. 154(b) by 957 days.

(21) Appl. No.: 16/617,756

(22) PCT Filed: Jun. 1, 2018

(86) PCT No.: PCT/US2018/035629
§ 371 (c)(1),
(2) Date: Nov. 27, 2019

(87) PCT Pub. No.: WO2018/223014
PCT Pub. Date: Dec. 6, 2018

(65) Prior Publication Data
US 2020/0109435 A1  Apr. 9, 2020

Related U.S. Application Data

(60) Provisional application No. 62/514,419, filed on Jun. 2, 2017.

(51) Int. Cl.
*C12Q 1/6804* (2018.01)
*G16B 30/00* (2019.01)
(Continued)

(52) U.S. Cl.
CPC ....... *C12Q 1/6804* (2013.01); *G01N 33/5308* (2013.01); *G01N 33/80* (2013.01);
(Continued)

(58) Field of Classification Search
CPC ............... G01N 33/80; G01N 2400/02; G01N 2400/38; G01N 2458/10
See application file for complete search history.

(56) References Cited

U.S. PATENT DOCUMENTS 8,030,006 B2   10/2011   Robb et al.
9,029,136 B2    5/2015   Heidtman et al.
(Continued)

FOREIGN PATENT DOCUMENTS

TW      1479024 B        4/2015
WO   WO-2007053358 A2 *  5/2007  ............. C07H 21/00
(Continued)

OTHER PUBLICATIONS

Gorska et al. Angew Chem Int Ed. 2009. 48:7695-7700. (Year: 2009).*

(Continued)

*Primary Examiner* — Joseph G. Dauner
(74) *Attorney, Agent, or Firm* — MUETING RAASCH GROUP

(57) ABSTRACT

Provided herein are DNA-glycan conjugates that include a glycan and a covalently attached polynucleotide. The polynucleotide includes a plurality of modules. Each module includes a nucleotide string, and the plurality of modules includes a monomer module that corresponds to each carbohydrate monomer present in the DNA-glycan conjugate, and a linkage module that corresponds to each glycosidic linkage present between each carbohydrate monomer in the DNA-glycan conjugate. The nucleotide sequence of the plurality of modules corresponds to the glycan structure.

(Continued)

Also provided herein are methods for making and using the DNA-glycan conjugates. Further provided is a computer-implemented method for translating data from a nucleotide sequence to a glycan structure, a system for converting data from a glycan structure to a nucleotide sequence, and a system for translating data from a nucleotide sequence to a glycan structure.

19 Claims, 39 Drawing Sheets

Specification includes a Sequence Listing.

(51) Int. Cl.
  G16B 40/20 (2019.01)
  G01N 33/53 (2006.01)
  G01N 33/80 (2006.01)
(52) U.S. Cl.
  CPC ............. *G16B 30/00* (2019.02); *G16B 40/20* (2019.02); *G01N 2400/02* (2013.01); *G01N 2400/38* (2013.01); *G01N 2458/10* (2013.01); *Y10T 436/143333* (2015.01)

(56) References Cited

U.S. PATENT DOCUMENTS

| | | | |
|---|---|---|---|
| 2007/0059769 A1* | 3/2007 | Blixt | A61P 31/12 435/7.1 |
| 2009/0075397 A1 | 3/2009 | Lin et al. | |
| 2009/0275484 A1 | 11/2009 | Wong et al. | |
| 2010/0016177 A1* | 1/2010 | Pedersen | C07D 405/04 506/17 |
| 2013/0331280 A1 | 12/2013 | Cummings et al. | |
| 2014/0087957 A1 | 3/2014 | Vuskovic et al. | |

FOREIGN PATENT DOCUMENTS

| | | |
|---|---|---|
| WO | WO 2014/145870 A2 | 9/2014 |
| WO | WO 2016/014595 A2 | 1/2016 |
| WO | WO 2016/077558 A1 | 5/2016 |
| WO | WO 2016/090165 A1 | 6/2016 |

OTHER PUBLICATIONS

Huang et al. ChemBioChem. 2011. 12:56-60. (Year: 2011).*
Daguer et al. Chem Sci. 2011. 2:625-632. (Year: 2011).*
Zambaldo et al. Current Opinion in Chemical Biology. 2015. 26:8-15. (Year: 2015).*
Delbianco et al. J Am Chem Soc. 2018. 140:5421-5426. (Year: 2018).*
Kondengaden et al. "DNA Encoded Glycan Libraries as a next-generation tool for the study of glycan-protein interactions" Retrieved from bioRxiv preprint doi: https://doi.org/10.1101/2020.03.30. 017012. Posted Mar. 31, 2020. (Year: 2020).*
Alam et al., "FASTAptamer: A Bioinformatic Toolkit for High-throughput Sequence Analysis of Combinatorial Selections," *Mol Ther Nucleic Acids*, Mar. 3, 2015; 4:e230.
Aoki-Kinoshita et al., "GlyTouCan 1.0—The international glycan structure repository," *Nucleic acids research*, 2015; 18(9):858-863.
Ban et al., "Discovery of glycosyltransferases using carbohydrate arrays and mass spectrometry," *Nat Chem Biol.*, Sep. 2012; 8(9):769-773.
Barnett et al., "The Glycome Analytics Platform: an integrative framework for glycobioninformatics," *Bioinformatics*, Jun. 10, 2016; 32(19):3005-3011.
Brenner et al., "Encoded combinatorial chemistry," *Proceedings of the National Academy of Sciences*, 1992; 89(12):5381-5383.
Chan et al., "Novel selection methods for DNA-encoded chemical libraries," *Current Opin Chem Biol.*, Jun. 2015; 26:55-61.
Chang et al., "Expression of Globo H and SSEA3 in breast cancer stem cells and the involvement of fucosyl transferases 1 and 2 in Globo H synthesis," *Proc Natl Acad Sci U S A*, Aug. 19, 2008; 105(33):11667-72.
Chen et al., "Aberrant expression of tumor-associated carbohydrate antigen Globo H in thyroid carcinoma," *J. Surg Oncol.*, Dec. 2016; 114(7)853-858.
Chevolot et al., "DNA-based carbohydrate biochips: a platform for surface glyco-engineering," *Angew Chem Int Ed Engl*, 2007; 46(14):2398-402.
Ciobanu et al., "Selection of a synthetic glycan oligomer from a library of DNA-templated fragments against DC-SIGN and inhibition of HIV gp120 binding to dendritic cells," *Chem Commun.*, 2011; 47:9321-9323.
Citartan et al., "Asymmetric PCR for good quality ssDNA generation towards DNA aptamer production," *Sonklanakarin Journal of Science and Technology*, 2012; 34(2), 125.
Clark et al., "Design, synthesis and selection of DNA-encoded small-molecule libraries," *Nat Chem Biol* 2009, 5 (9), 647-54.
Danishefsky et al., "Development of Globo-H cancer vaccine," *Acc Chem Res*, Mar. 17, 2015; 48(3):643-652.
Denong Wang et al., "Carbohydrate microarrays for the recognition of cross-reactive molecular markers of microbes and host cells," *Nature Bitotechnol*, Mar. 2002; 20(3):275-281.
D-glucan, A., IUPAC-IUB Joint Commission on Biochemical Nomenclature (JCBN), "Polysaccharide nomenclature. Recommendations 1980," *Euro J Biochem.*, Sep. 1, 1982; 126(3):439-441.
Dotz et al., "Histo-blood group glycans in the context of personalized medicine," Biochimica et Biophysica Acta 1860, Aug. 2016, 1596-1607.
Dube et al., "Glycans in cancer and inflammation—potential for therapeutics and diagnostics," *Nat Rev Drug Discov.*, Jun. 2005; 4(6):477.
El-Sagheer et al., "Click chemistry with DNA", Applications of click chemistry themed issue, *Chemical Society reviews*, Feb. 2010, 39 (4), 1388-1405.
Fernandez-Tejada et al., "Recent Developments in Synthetic Carbohydrate-Based Diagnostics, Vaccines, and Therapeutics," *Chemistry*, Jul. 20, 2015; 21(30):10616-10628.
Goodnow et al., "DNA-encoded chemistry: enabling the deeper sampling of chemical space," *Nat Rev Drug Discov*, Dec. 2016; 16(2):1-17.
Goodwin et al., "Coming of age: ten years of next-generation sequencing technologies," *Nat Rev Genet*, 2016; 17(6):333-351.
Hahm et al., "Automated glycan assembly using the Glyconeer 2.1 synthesizer," *Proceedings of the National Academy of Sciences*, Apr. 25, 2017; 114(17):E3385-3389.
Harvey et al., "Symbol nomenclature for representing glycan structures: Extension to cover different carbohydrate types," *Proteomics*, 2011; 11(22):4291-4295.
Hein et al., "Click Chemistry, a Powerful Tool for Pharmaceutical Sciences," *Pharm Res.*, Oct. 2008; 25(10):2216-2230.
Horlacher et al., "Carbohydrate arrays as tools for research and diagnostics," *Chem Soc Rev*, Jul. 2008; 37(7):1414-22.
Huang et al., "Carbohydrate microarray for profiling the antibodies interacting with Globo H tumor antigen," *Proc Natl Acad Sci U S A*, Jan. 3, 2006; 103(1):15-20.
International Preliminary Report on Patentability dated Dec. 12, 2019 for International Application No. PCT/US2018/035629; 8 pages.
International Search Report and Written Opinion dated Aug. 16, 2018 for International Application No. PCT/US2018/035629; 16 pages.
Jungbauer et al., "High-throughput multiplex PCR genotyping for 35 red blood cell antigens in blood donors," *Vox sanguinis* 2012, 102 (3), 234-42.
Kleiner et al., "Small-molecule discovery from DNA-encoded chemical libraries," *Chem Soc Rev*, Dec. 2011; 40(12): 5707-5717.
Kornfeld et al., "The synthesis of complex-type oligosaccharides. II. Characterization of the processing intermediates in the synthesis of the complex oligosaccharide units of the vesicular stomatitis virus G protein," *Journal of Biological Chemistry*, Apr. 1978; 253(21), 7771-7778.

(56) References Cited

OTHER PUBLICATIONS

Kudryashov et al., "Characterization of a mouse monoclonal IgG3 antibody to the tumor-associated globo H structure produced by immunization with a synthetic glycoconjugate," *Glycoconj J*, Mar. 1998; 15(3):243-249.

Kwon et al., "High sensitivity detection of active botulinum neurotoxin by glyco-quantitative polymerase chain-reaction," *Anal Chem*, 2014; 86(5):2279-84.

Kwon et al., "Signal Amplification by Glyco-qPCR for Ultrasensitive Detection of Carbohydrates: Applications in Glycobiology," *Angew Chem Int Edit*, 2012; 51(47):11800-11804.

Lau et al., "Highly efficient chemoenzymatic synthesis of β1-4-linked galactosides with promiscuous bacterial β1-4-galactosyltransferases," *Chem. Commun. 46*, 2010; 6066-6068.

Lerner et al., "DNA-Encoded Compound Libraries as Open Source: A Powerful Pathway to New Drugs," *Angewandte Chemie International Edition*, 2017; 56(5):1164-1165.

Li et al., "Efficient Chemoenzymatic Synthesis of an N-glycan Isomer Library," *Chem Sci*, Oct. 1, 2015; 6(10):5652-5661.

Li et al., "Novel encoding methods for DNA-templated chemical libraries," *Current Opinion in Chemical Biology*, 2015; 26:25-33.

Li Yanhong et al., "Donor substrate promiscuity of bacterial β1-3-N-acetylglucosaminyltransferases and acceptor substrate flexibility of β1-4-galactosyltransferases," *Biorg. Med. Chem. 24*, 2016; 1696-1705.

Liao et al., "Immunization of fucose-containing polysaccharides from Reishi mushroom induces antibodies to tumor-associated Globo H-series epitopes," *Proc Natl Acad Sci U S A*, Aug. 20, 2013; 110(34): 13809-13814.

Litovchik et al., "Encoded Library Synthesis Using Chemical Ligation and the Discovery of sEH Inhibitors from a 334-Million Member Library," *Sci Rep.*, Jun. 10, 2015; 2015(5):10916.

McGregor et al., "Identification of ligand-target pairs from combined libraries of small molecules and unpurified protein targets in cell lysates," *J Am Chem Soc*, Feb. 26, 2014; 136(8):3264-3670.

McNaught, "Nomenclature of Carbohydrates," *Pure and Applied Chemistry*, 1996; 68(10):1919-2008.

Melkko et al., "Lead discovery by DNA-encoded chemical libraries," *Drug discovery today* 2007, 12 (11-12), 465-71.

Muthana et al., "Efficient one-pot multienzyme synthesis of UDP-sugars using a promiscuous UDP-sugar pyrophosphorylase from Bifidobacterium longum (BLUSP)," *Chem. Commun. 48*, 2012; 1-18.

O'Cearbhaill et al., "A Phase I Study of Unimolecular Pentavalent (Globo-H-GM2-sTn-TF-Tn) Immunization of Patients with Epithelial Ovarian, Fallopian Tube, or Peritoneal Cancer in First Remission," *Cancers*, 2016; 8(4).

Pinho et al., "Glycosylation in cancer: mechanisms and clinical implications," *Nat Rev Cancer*, Sep. 2015; 15(9):540-550.

Pochechueva et al., "Comparison of printed glycan array, suspension array and ELISA in the detection of human anti-gylcan antibodies," *Glyconj J*, 2011; 28(8-9):507-517.

Pochechueva et al., "Multiplex suspension array for human anti-carbohydrate antibody profiling," Analyst, Feb. 7, 2011; 136(3):560-569.

Pochechueva et al., "Naturally occurring anti-glycan antibodies binding to Globo H-expressing cells identify ovarian cancer patients," *J. Ovarian Res.*, Feb. 10, 2017; 10(1):8.

Purohit et al., "Multiplex glycan bead array for high throughput and high content analyses of glycan binding proteins," *Nature Communication*, 2018; 9.

Robinson et al., "Glyco-seek: Ultrasensitive Detection of Protein-Specific Glycosylation by Proximity Ligation Polymerase Chain Reaction," Journal of the American Chemical Society, 2016; 138:10722-10725.

Sanchez et al., "Linear-After-The-Exponential (LATE)—PCR: An advanced method of asymmetric PCR and its uses in quantitative real-time analysis," *Proceedings of the National Academy of Sciences*, 2004; 101(7):1933-1938.

Sano et al., "Immuno-PCR: Very sensitive antigen detection by means of specific antibody-DNA conjugates," *Science*, Oct. 2, 1992; 258(5079):120-122.

Scheuermann et al., "DNA-encoded chemical libraries," *Journal of Biotechnology*, 2006; 126(4):568-81.

Seto et al., "Enzymatic synthesis of blood group A and B trisaccharide analogues," *Carbohydr. Res. 324*, 2000; 161-169.

Shi et al., "Recent advances on the encoding and selection methods of DNA-encoded chemical library," *Bioorganic & Medicinal Chemistry Letters*, 2017; 361-369.

Shinmachi et al., "Using GlyTouCan Version 1.0: The First International Glycan Structure Repository," in a Practical Guide to Using Glycomics Databases. Aoki-Kinoshita (Ed.) Springer: Japan, 2017; 41-73.

Song et al., "Chemistry of natural glycan microarrays," Current Opinion in chemical biology, 2014; 18:70-77.

Song et al., "Glycan microarrays of fluorescently-tagged natural glycans," *Glycoconj Journal*, Oct. 2015; 32(7):465-473.

Su et al., "Enzymatic synthesis of tumor-associated carbohydrate antigen Globo-H hexasaccharide," *Organic letters 10*, 2008; 1009-1012.

Temme et al., "Directed evolution of 2G12-targeted nonamannose glycoclusters by SELMA," *Chemistry*, Dec. 16, 2013; 19(51):17291-17295.

Thomas et al., "Application of Biocatalysis to on-DNA Carbohydrate Library Synthesis," *Chembiochem*, May 4, 2017; 18(9):858-863.

Tilley et al., "Is Next Generation Sequencing the future of blood group testing?," *Transfusion and apheresis science, Science Direct*, 50 (2), Apr. 2014, pp. 183-188.

Tsai et al., "Ultrasensitive Antibody Detection by Agglutination-PCR (ADAP)," *ACS Central Science*, 2016; 2:139-147.

Turnbull et al., "Dissecting the cholera toxin-ganglioside GM1 interaction by isothermal titration calorimetry," *J Am Chem Soc.*, Feb. 4, 2004; 126(4):1047-1054.

Varki et al., "Symbol nomenclature for glycan representation," *Proteomics*, Dec. 2009; 9(24):5398-5399.

Wang et al., "Cross-platform comparison of glycan microarray formats," *Glycobiology*, Jun. 2014; 24(6):507-517.

Wang et al., "Glycan microarray of Globo H and related structures for quantitative analysis of breast cancer," *Proc Natl Acad Sci U S A*, Aug. 19, 2008; 105(33):11661-6.

Wu et al., "Electrophoretic deposition of poly [3-(3-N, N-diethylaminopropoxy)thiphene] and composite films," *Materials Chemistry and Physics*, 2011; 103(1):15-20.

www.functionalglycomics.org, "Symbol and Text Nomenclature for Representation of Glycan Structure," Nomenclature Committee, Consortium for Functional Glycomics, May 2012. www.functionalglycomics.org/static/consortium/Nomenclature.shtml [online].

Xiao et al., "Chemoenzymatic Synthesis of a Library of Human Milk Oligosaccharides," *Journal of organic chemistry*, Jul. 15, 2016; 81(14):5851-5865.

Yunlong Chen et al., "Arrayed Profiling of Multiple Glycans on Whole Living Cell Surfaces," *Anal Chem*, 2013; 85:11153-11158.

Zeng et al., "Glycosylated Conductive Polymer: A Multimodal Biointerface for Studying Carbohydrate-Protein Interactions," *Acc Chem Res*, Sep. 20, 2016; 49(9):1624-1633.

Zhang et al., "Carbohydrate-protein interactions by "clicked" carbohydrate self-assembled monolayers," Anal Chem, Mar. 15, 2006; 78(6):2001-2008.

Zhang et al., "Selection of tumor antigens as targets for immune attack using immunohistochemistry: I. Focus on gangliosides," *Int. J. Cancer*, Sep. 26, 1997; 73:42-49.

Zhang et al., "Selection of tumor antigens as targets for immune attack using immunohistochemistry: II. Blood group-related antigens," *Int. J. Cancer*, Sep. 26, 1997; 73.

Zhao et al., "Enzymatic route to preparative-scale synthesis of UDP-GlcNAc/GalNAc, their analogues and GDP-fucose," *Nature Protocols 5*, 2010; 636-646.

Zhou et al., "A Fully Synthetic Self-Adjuvanting Globo H-Based Vaccine Elicited Strong T Cell-Mediated Antitumor Immunity," *Chem Sci*, Dec. 1, 2015; 6(12):7112-7121.

(56) References Cited

OTHER PUBLICATIONS

Zhugong Liu et al., "Extended blood group molecular typing and next-generation sequencing," *Transfusion medicine reviews* 2014, 28 (4), 177-86.

Chen, Y., et al., "Arrayed profiling of multiple glycans on whole living cell surfaces." Analyt Chem, 2013, 85(22): p. 11153-11158.

Cheng, S. P., et al., "Aberrant expression of tumor-associated carbohydrate antigen Globo H in thyroid carcinoma." J Surg Oncol, 2016, 114(7): p. 853-858.

Dauger, J. P., et al., "DNA-templated combinatorial assembly of small molecule fragments amenable to selection/amplification cycles." Chem Sci, 2011, 2: p. 625-632.

Gorska, K., et al., "DNA-templated homo- and heterodimerization of peptide nucleic acid encoded oligosaccharides that mimic the carbohydrate epitope of HIV." Angew. chem. Int. Ed. 2009, 48: p. 7695-7700.

Huang, K., et al., "Combinatorial self-assembly of glycan fragments into microarrays." ChemBioChem, 2011, 12: p. 56-60.

Seeberger, P. H., "The logic of automated glycan assembly. Accounts of chemical research." 2015, 48(5): p. 1450-1463.

Zambaldo, C. et al., "PNA-encoded chemical libraries." Curr Op in Chem Bio, 2015, 26: p. 8-15.

\* cited by examiner

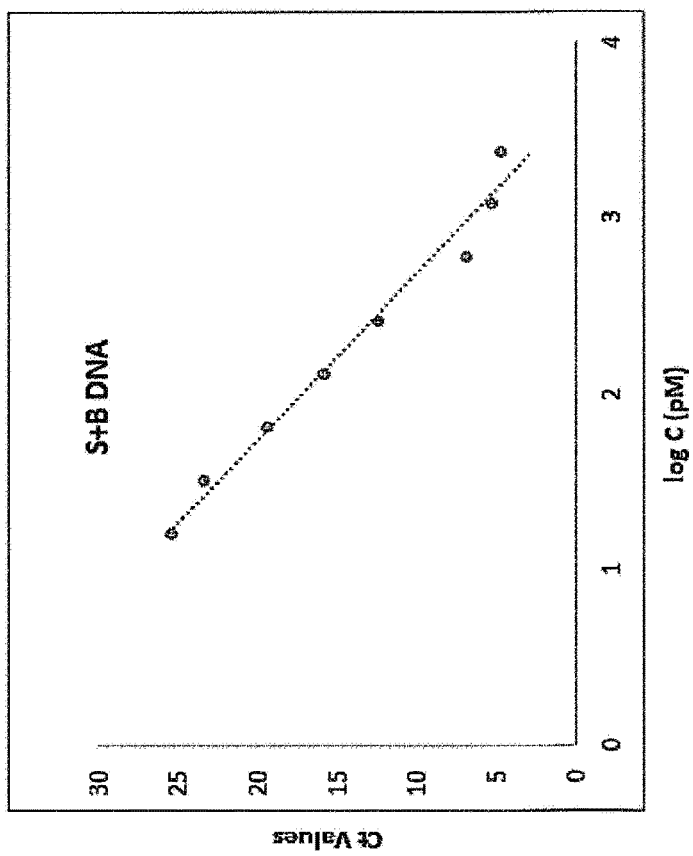
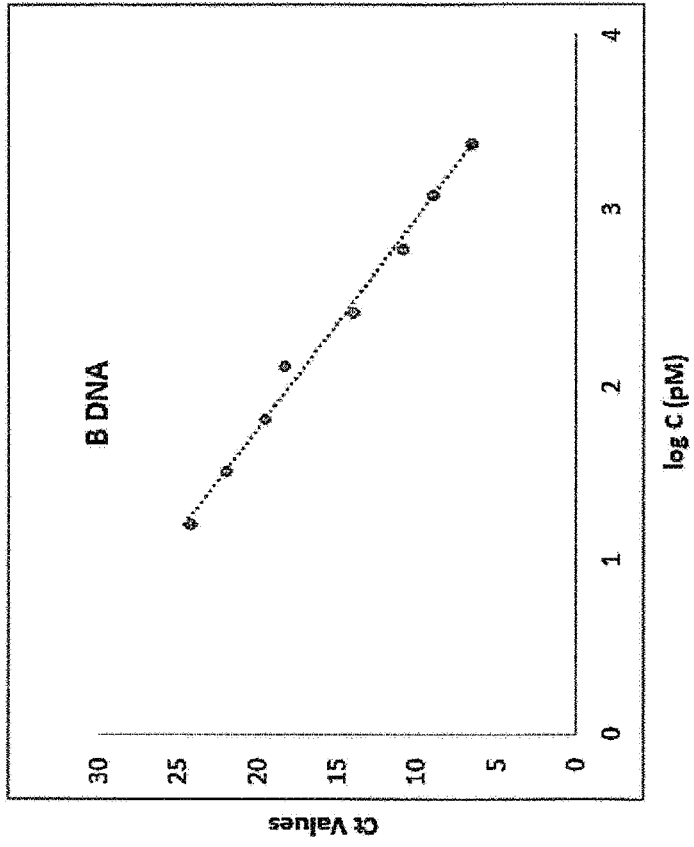
FIG. 17

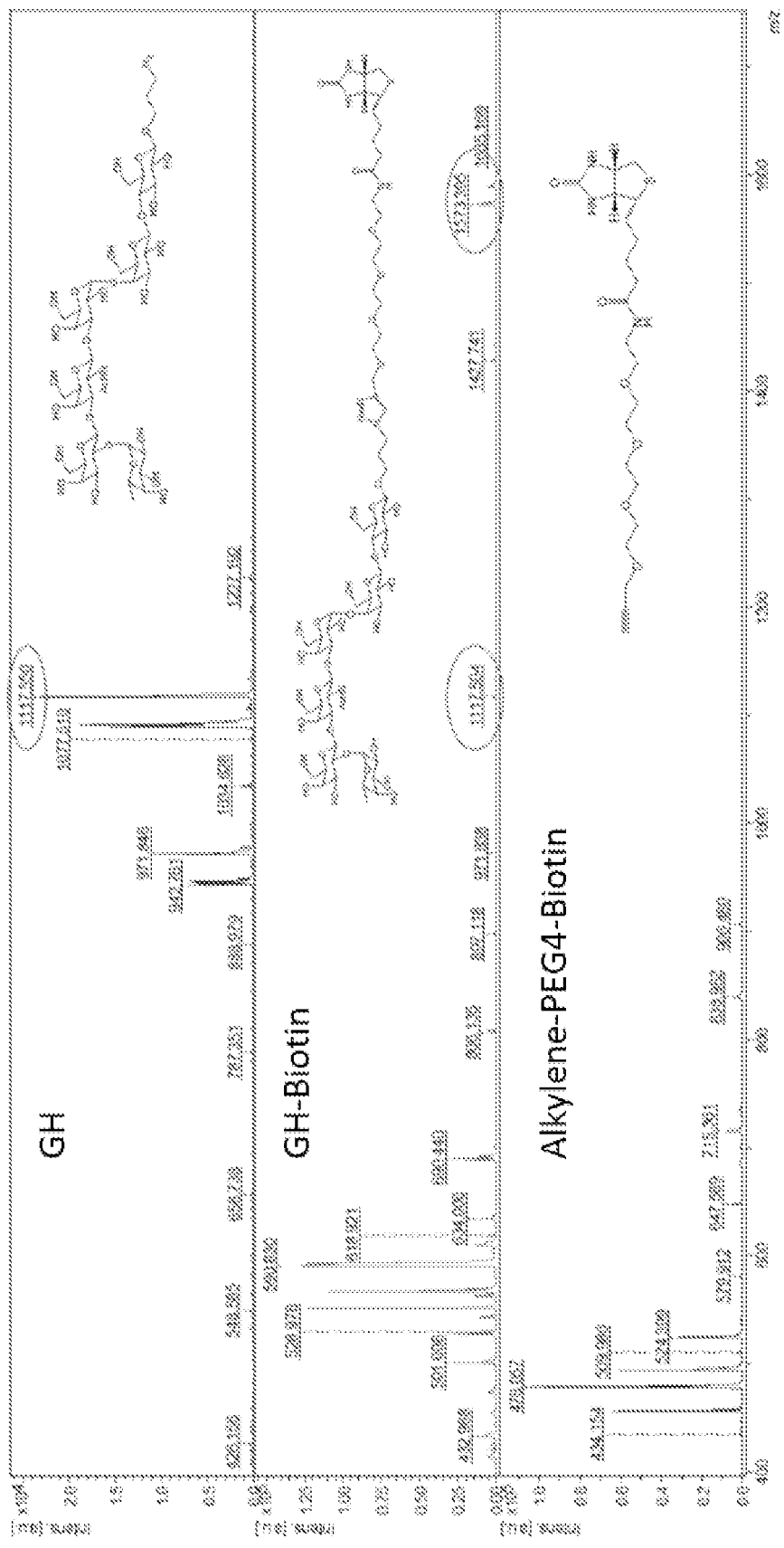
FIG. 30, continued

FIG. 31B

Step 1:

Click conjugation of head piece

/5Hexynyl/AAT GAT ACG GCG A-OH + Glycan = Glycan-AAT GAT ACG GCG A-OH
(headpiece)                                 (Glycan + headpiece)

Step 2:

Hybridize with reverse DNA

Glycan-AAT GAT ACG GCG A-OH (Glycan + headpiece) +

5' GTGACTGGAGTTCAGACGTGTCTTACACATCGTAGAGCTTAGATCGTTTTCTTTTCTAAAGTTGCGTTCGGTGGTCGCCGTATCATT

→

Glycan-AATGATACGGCGA-3'

3'-TTACTATGCCGCTGGTGGCTTGCGTTGAAATCTTTTCTTTTGCTAGATTCGAGATGCTACATTCTGTGCAGACTT
GAGGTCAGTG

Step 3:

Add tail DNA and ligate

P-CCACCGAACGCAACTTTAGAAAAGAAAACGATCTAAGCTCTACGATGTAAGACACGTCTGAACTC

→

Glycan-AATGATACGGCGACCACCGAACGCAACTTTAGAAAAGAAAACGATCTAAGCTCTACGATGTAAGACACGTCTGAACTC3'

3'TTACTATGCCGCTGGTGGCTTGCGTTGAAATCTTTTCTTTTGCTAGATTCGAGATGCTACATTCTGTGCAGACTT
GAGGTCAGTG

FIG. 33A
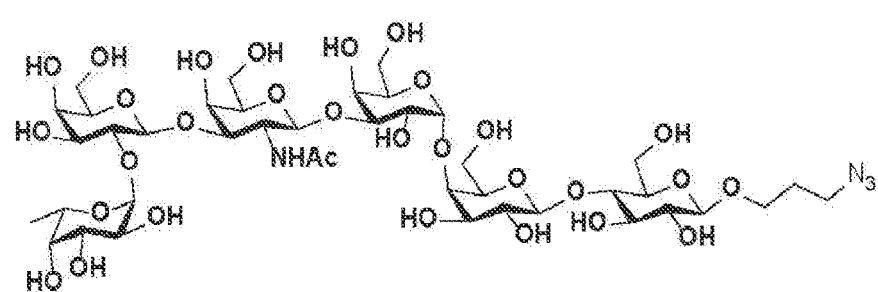
Chemical Formula: $C_{41}H_{70}N_4O_{30}$ Gb-H
Molecular Weight: 1099.01
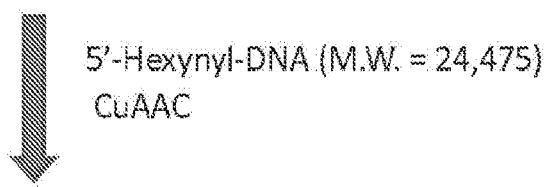
5'-Hexynyl-DNA (M.W. = 24,475)
CuAAC
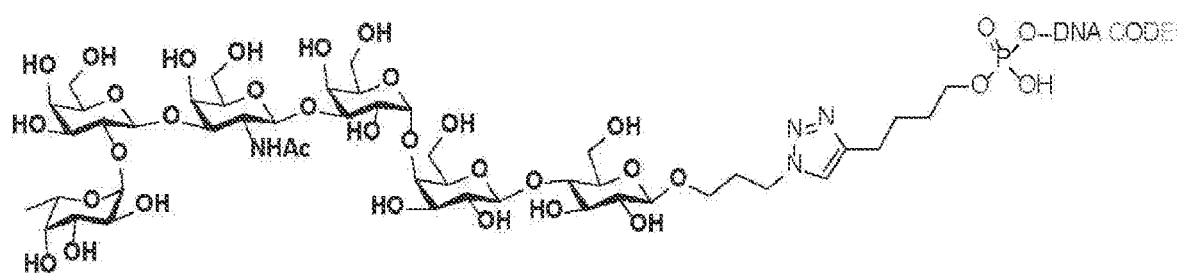
5Hexynyl/DNA code+ Globo H = GbH-DNA (M.W. =25,574)

SEQUENCE LISTING

```
<160> NUMBER OF SEQ ID NOS: 230

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
ccccagtcag gcctaacgta                                                20

<210> SEQ ID NO 2
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
aatatgtaag ctgttttaga aacaaaaaag c                                   31

<210> SEQ ID NO 3
<211> LENGTH: 25
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 3 ataacaaat atgtaagctg taagc                                      25

<210> SEQ ID NO 4
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
acgatgtaag ctgt                                                 14

<210> SEQ ID NO 5
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
acgaaacacg atgtaagctc a                                         21

<210> SEQ ID NO 6
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
acgaaacacg atgtaagctc t                                         21

<210> SEQ ID NO 7
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
acgatctaag ctgt                                                 14

<210> SEQ ID NO 8
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
aataaacaat aaca                                                 14
```

```
<210> SEQ ID NO 9
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
acgctgtaag ctca                                                      14

<210> SEQ ID NO 10
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
agaaaacaag ctca                                                      14

<210> SEQ ID NO 11
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
agaaaagacg atgttttaga aaacaaaaag ctca                                34

<210> SEQ ID NO 12
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
agaaaagacg atgtaagctc a                                              21

<210> SEQ ID NO 13
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
acgatgtttt agaaaacaaa aagctgt                                        27

<210> SEQ ID NO 14
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 14
acgctgtaag ctta                                                          14

<210> SEQ ID NO 15
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
acgatgtaag ctta                                                          14

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
aggcggtacg atgtaagctg t                                                  21

<210> SEQ ID NO 17
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
aggcggtacg atgtaagctt a                                                  21

<210> SEQ ID NO 18
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
acgctgtttt agaaagaaa aagctgtaat aaactttacg ctgttttaga aagaaaaag          60 ctgtaataac aaaaatatg taagctgttt tagaaacaaa aaagc                        105

<210> SEQ ID NO 19
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
acgatgtaag ctgtaataaa ctttacgatg taagctgtaa taacaaaaaa tatgtaagct        60
gttttagaaa caaaaaagc                                                     79
```

```
<210> SEQ ID NO 20
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
acgatgtaag ctgtaataaa ctttaagctg taataacaaa aaatatgtaa gctgttttag      60
aaacaaaaaa gc                                                         72

<210> SEQ ID NO 21
<211> LENGTH: 159
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
acgatggttc ttttacgatg ggttaaaaaa gctgtaagct caaataaact ttacgatggg      60
ttaacgatgg gtcttttacg atgggttaaa aaagctgtaa gctcaaataa caaaatttat     120
catcaaaaaa tatgtaagct gttttagaaa caaaaaagc                           159

<210> SEQ ID NO 22
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
acgaaacacg atgtaagctc atttacgaaa cacgatgtaa gctgtaaaaa taaactttac      60
gaaacacgat gtaagctcaa ataacaaaaa atatgtaagc tgttttagaa acaaaaaagc     120

<210> SEQ ID NO 23
<211> LENGTH: 113
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
acgaaacacg atgtaagctc atttacgatg taagctgtaa aaataaactt tacgaaacac      60
gatgtaagct caaataacaa aaatatgta agctgtttta gaaacaaaaa agc             113

<210> SEQ ID NO 24
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
acgaaacacg atgtaagctc aaataaactt tacgaaacac gatgtaagct caaataacaa      60
```

```
aaaatatgta agctgttttta gaaacaaaaa agc                                93
```

<210> SEQ ID NO 25
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25

```
acgaaacacg atgtaagctc aaataaactt tacgatgtaa gctcaaataa caaaaaatat    60
gtaagctgtt ttagaaacaa aaaagc                                        86
```

<210> SEQ ID NO 26
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26

```
acgaaacacg atgtaagctc aaataaactt taagctcaaa taacaaaaaa tatgtaagct    60
gttttagaaa caaaaaagc                                                79
```

<210> SEQ ID NO 27
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27

```
acgaaacacg atgtaagctc aaataaactt taataacaaa aaatatgtaa gctgttttag    60
aaacaaaaaa gc                                                       72
```

<210> SEQ ID NO 28
<211> LENGTH: 134
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28

```
acgaaacacg atgtaagctc ttttacgaaa cacgatgtaa gcttaaaaac gatgtaagct    60
caaataaact ttacgaaaca cgatgtaagc tcaaataaca aaaatatgt aagctgtttt   120 agaaacaaaa aagc                                                    134
```

<210> SEQ ID NO 29
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29

```
acgatgtaag ctcatttacg atctaagctg taaaaataaa ctttacgatg taagctcatt    60
tacgatgtaa gcttaaaaaa taacaaaaaa tatgtaagct gttttagaaa caaaaaagc    119

<210> SEQ ID NO 30
<211> LENGTH: 112
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30
acgatgtaag ctcatttacg atgttttaga aacaaaaag ctgtaaaaat aaactttacg    60
atgtaagctc aaataacaaa aaatatgtaa gctgttttag aaacaaaaaa gc           112

<210> SEQ ID NO 31
<211> LENGTH: 106
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31
acgatgtaag ctcatttacg atgtaagctg taaaaataaa ctttacgaaa cacgatgtaa    60
gctcaaataa caaaaaatat gtaagctgtt ttagaaacaa aaagc                    106

<210> SEQ ID NO 32
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32
acgatgtaag ctcatttacg atgtaagctg taaaaataaa ctttacgatg taagctcatt    60
tacgatgtaa gcttaaaaaa taacaaaaaa tatgtaagct gttttagaaa caaaaaagc    119

<210> SEQ ID NO 33
<211> LENGTH: 98
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
acgatgtttt agaaaacaaa aagctcaaat aaactttaat aaactttaat aacaaaaaat    60
aacaaaaaat atgtaagctg ttttagaaac aaaaaagc                            98

<210> SEQ ID NO 34
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 34
acgatgtttt agaaaacaaa aagctcaaat aaactttacg atgtaagctc aaataacaaa    60
aaatatgtaa gctgttttag aaacaaaaaa gc    92

<210> SEQ ID NO 35
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
acgatgtttt agaaaacaaa aagctcaaat aaactttaat aacaaaaaat atgtaagctg    60
ttttagaaac aaaaaagc    78

<210> SEQ ID NO 36
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
acgatctaag ctgtaagcag ttttaagcag taaaaataaa ctttaataag taataaacaa    60
aaatatgtaa gctgttttag aaacaaaaaa gc    92

<210> SEQ ID NO 37
<211> LENGTH: 112
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37
acgatgtttt agaaaacaaa aagctcattt acgatgtaag ctgtaaaaat aaactttacg    60
atgtaagctc aaataacaaa aaatatgtaa gctgttttag aaacaaaaaa gc    112

<210> SEQ ID NO 38
<211> LENGTH: 138
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38
acgatgtttt agaaaacaaa aagctcattt acgatgtttt agaaaacaaa aagctgtaaa    60
aataaacttt acgatgtttt agaaaacaaa aagctcaaat aacaaaaaat atgtaagctg    120
ttttagaaac aaaaaagc    138

<210> SEQ ID NO 39
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 39
acgatgtttt agaaaacaaa aagctcaaat aaactttacg atgttttaga aaacaaaaag    60
ctcaaataac aaaaaatatg taagctgttt tagaaacaaa aaagc    105

<210> SEQ ID NO 40
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 40
acgatgtaag ctcaaataaa ctttacgatg taagctcatt tacgctgtaa gcttaaaaaa    60
taacaaaaaa tatgtaagct gttttagaaa caaaaaagc    99

<210> SEQ ID NO 41
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 41
acgatgtaag ctcaaataac atttacgatg taagctcatt tacgctgtaa gcttaaaaaa    60
taaacaaaaa tatgtaagct gttttagaaa caaaaaagc    99

<210> SEQ ID NO 42
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 42
acgatgtaag ctcaaataaa ctttacgctg taagctcatt tacgatgtaa gcttaaaaaa    60
taacaaaaaa tatgtaagct gttttagaaa caaaaaagc    99

<210> SEQ ID NO 43
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 43
acgatgtaag ctcaaataaa ctttaggggt tacgatgtaa gctcaaataa caaaaaatat    60
gtaagctgtt ttagaaacaa aaagc    86

<210> SEQ ID NO 44
<211> LENGTH: 79
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 44
acgatgtaag ctcaaataaa ctttaataaa gaataaacaa taacaaaaaa tatgtaagct    60
gttttagaaa caaaaaagc                                                 79

<210> SEQ ID NO 45
<211> LENGTH: 85
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
acgatgtaag ctcaaataaa ctttaataaa ctttaataac aaaaaataac aaaaaatatg    60
taagctgttt tagaaacaaa aaagc                                          85

<210> SEQ ID NO 46
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
acgatgtaag ctcaaataaa ctttacgctg taagctcaaa taacaaaaaa tatgtaagct    60
gttttagaaa caaaaaagc                                                 79

<210> SEQ ID NO 47
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
acgatgtaag ctcaaataaa ctttaagctc aaataacaaa aaatatgtaa gctgttttag    60
aaacaaaaaa gc                                                        72

<210> SEQ ID NO 48
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
acgatgtaag ctcaaataaa ctttacgatg taagctcaaa taacaaaaaa tatgtaagct    60
gttttagaaa caaaaaagc                                                 79

<210> SEQ ID NO 49
<211> LENGTH: 99
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 49
acgatgtaag ctcaaataaa ctttacgatg taagctcatt tacgatgtaa gcttaaaaaa    60
taacaaaaaa tatgtaagct gttttagaaa caaaaaagc                           99

<210> SEQ ID NO 50
<211> LENGTH: 106
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50
acgatgtaag ctcaaataaa ctttacgatg taagctcatt tacgaaacac gatgtaagct    60
taaaaaataa caaaaatat gtaagctgtt ttagaaacaa aaaagc                   106

<210> SEQ ID NO 51
<211> LENGTH: 106
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51
acgatgtaag ctcaaataaa ctttacgaaa cacgatgtaa gctcatttac gatgtaagct    60
taaaaaataa caaaaatat gtaagctgtt ttagaaacaa aaaagc                   106

<210> SEQ ID NO 52
<211> LENGTH: 140
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 52
acgatgtaag ctcatttagg cggtacgatg taagctgtaa aaataaactt taggcggtac    60
gatgtaagct catttaggcg gtacgatgta agcttaaaaa ataacaaaaa atatgtaagc   120
tgttttagaa acaaaaaagc                                               140

<210> SEQ ID NO 53
<211> LENGTH: 133
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53
acgatgtaag ctcatttagg cggtacgatg taagctgtaa aaataaactt taggcggtac    60
gatgtaagct catttacgat gtaagcttaa aaataacaa aaatatgta agctgtttta    120 gaaacaaaaa agc                                                      133
```

<210> SEQ ID NO 54
<211> LENGTH: 133
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54
acgatgtaag ctcatttacg atgtaagctg taaaaataaa ctttaggcgg tacgatgtaa    60
gctcatttag gcggtacgat gtaagcttaa aaataacaa aaaatatgta agctgtttta    120
gaaacaaaaa agc                                                      133

<210> SEQ ID NO 55
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
acgatgtaag ctcatttacg atgtaagctg taaaaataaa ctttaagctc aaataacaaa    60
aaatatgtaa gctgttttag aaacaaaaaa gc                                  92

<210> SEQ ID NO 56
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
acgatgtaag ctcatttacg atgtaagctg taaaaataaa ctttacgatg taagctcaaa    60
taacaaaaaa tatgtaagct gttttagaaa caaaaaagc                           99

<210> SEQ ID NO 57
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
acgatgtaag ctgtaataaa ctttaataac aaaaaatatg taagctgttt tagaaacaaa    60
aaagc                                                                65

<210> SEQ ID NO 58
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
acgatgtaag ctctacgatg taagctcaaa taaactttac gatgtaagct caaataacaa    60
aaaatatgta agctgtttta gaaacaaaaa agc    93

<210> SEQ ID NO 59
<211> LENGTH: 161
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 59
acgatgtaag ctctacgatg taagctcatt tacgatgtaa gctgtaaaaa taaactttac    60
gatgtaagct ctacgatgta agctcattta cgatgtaagc tctacgatgt aagcttaaaa   120
aataacaaaa aatatgtaag ctgttttaga aacaaaaaag c                       161

<210> SEQ ID NO 60
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 60
acgctgtttt agaaacaaa aagctcaaat aaactttagg cggtacgctg taagctcaaa    60
taacaaaaaa tatgtaagct gttttagaaa caaaaaagc                          99

<210> SEQ ID NO 61
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 61
acgctgtttt agaaacaaaa aagctcaaat aaactttaat aacaaaaaat atgtaagctg    60
ttttagaaac aaaaaagc                                                 78

<210> SEQ ID NO 62
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 62
acgctgtttt agaaacaaaa aagctcaaat aaacttacg ctgtaagctc aaataacaaa     60
aaatatgtaa gctgttttag aaacaaaaaa gc                                 92

<210> SEQ ID NO 63
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

```
<400> SEQUENCE: 63
acgctgtttt agaaaacaaa aagctcaaat aaactttacg aaacacgatg taagctcaaa    60
taacaaaaaa tatgtaagct gttttagaaa caaaaaagc                          99

<210> SEQ ID NO 64
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
acgccatttg taagctcaaa taaactttaa taaacaataa caaaaaatat gtaagctgtt    60
ttagaaacaa aaaagc                                                   76

<210> SEQ ID NO 65
<211> LENGTH: 83
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
acgccatttg taagctcaaa taaactttac gctgtaagct caaataacaa aaaatatgta    60
agctgtttta gaaacaaaaa agc                                           83

<210> SEQ ID NO 66
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
acgccatttg taagctcaaa taaactttag gcggtacgat gtaagctcaa ataacaaaaa    60
atatgtaagc tgttttagaa acaaaaaagc                                    90

<210> SEQ ID NO 67
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
acgccatttg taagctcaaa taaactttag gcgttacgat gtaagctcaa ataacaaaaa    60
atatgtaagc tgttttagaa acaaaaaagc                                    90

<210> SEQ ID NO 68
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 68
acgctgtaag ctcaaataaa ctttaagctc atttacgctg taagcttaaa aaataacaaa    60
aaatatgtaa gctgttttag aaacaaaaaa gc                                  92

<210> SEQ ID NO 69
<211> LENGTH: 85
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
acgctgtaag ctcaaataaa ctttaagctc atttaagctt aaaaaataac aaaaaatatg    60
taagctgttt tagaaacaaa aaagc                                          85

<210> SEQ ID NO 70
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
acgctgtaag ctcaaataaa ctttaataac aaaaaatatg taagctgttt tagaaacaaa    60
aaagc                                                                65

<210> SEQ ID NO 71
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
acgctgtaag ctcaaataaa ctttaggcgt tacgatgtaa gctcaaataa caaaaaatat    60
gtaagctgtt ttagaaacaa aaaagc                                         86

<210> SEQ ID NO 72
<211> LENGTH: 83
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
acgctgtaag ctcaaataaa ctttacgcca tttgtaagct caaataacaa aaatatgta     60 agctgtttta gaaacaaaaa agc                                            83

<210> SEQ ID NO 73
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 73
acgctgtaag ctcaaataaa ctttacgatg taagctcatt tacgatgtaa gcttaaaaaa     60
taacaaaaaa tatgtaagct gttttagaaa caaaaaagc     99

<210> SEQ ID NO 74
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
acgctgtaag ctcaaataaa ctttacgatg taagctcaaa taacaaaaaa tatgtaagct     60
gttttagaaa caaaaaagc     79

<210> SEQ ID NO 75
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
acgctgtaag ctcatttacg atgtaagctg taaaaataaa ctttacgctg taagctcatt     60
tacgatgtaa gcttaaaaaa taacaaaaaa tatgtaagct gttttagaaa caaaaaagc     119

<210> SEQ ID NO 76
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
acgctgtaag ctcatttacg atgtaagctg taaaaataaa ctttacgatg taagctcaaa     60
taacaaaaaa tatgtaagct gttttagaaa caaaaaagc     99

<210> SEQ ID NO 77
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 77
acgctgtaag ctcatttacg atgtaagctg taaaaataaa ctttacgctg taagctcatt     60
tacgctgtaa gcttaaaaaa taacaaaaaa tatgtaagct gttttagaaa caaaaaagc    119

<210> SEQ ID NO 78
<211> LENGTH: 98
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 78
acgctgtaag ctcatttaag ctgtaaaaat aactttaag ctcatttaag cttaaaaat      60 aacaaaaaat atgtaagctg ttttagaaac aaaaaagc                            98

<210> SEQ ID NO 79
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 79
acgctgtaag ctcatttaag ctgtaaaaat aactttacg ctgtaagctc atttaagctt     60
aaaaaataac aaaaaatatg taagctgttt tagaaacaaa aaagc                    105

<210> SEQ ID NO 80
<211> LENGTH: 85
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 80
acgctgtaag ctcatttaag ctgtaaaaat aactttaag ctcaaataac aaaaaatatg     60
taagctgttt tagaaacaaa aaagc                                          85

<210> SEQ ID NO 81
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 81
acgctgtaag ctcaaataaa ctttacgctg taagctcaaa taacaaaaaa tatgtaagct    60
gttttagaaa caaaaaagc                                                 79

<210> SEQ ID NO 82
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 82
agaaaacaag ctcaaataaa ctttaataac aaaaaatatg taagctgttt tagaaacaaa    60
aaagc                                                                65

<210> SEQ ID NO 83
<211> LENGTH: 106
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"

<400> SEQUENCE: 83
agaaaagacg atgttttaga aaacaaaaag ctcaaataaa ctttagaaaa gacgatgtaa      60
gctcaaataa caaaaaatat gtaagctgtt ttagaaacaa aaagc                     106

<210> SEQ ID NO 84
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84
agaaaagacg atgttttaga aaacaaaaag ctcaaataaa ctttagaaaa gacgatgttt      60
tagaaaacaa aaagctcaaa taacaaaaaa tatgtaagct gttttagaaa caaaaaagc      119

<210> SEQ ID NO 85
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
agaaaagacg atgttttaga aaacaaaaag ctcaaataaa ctttaataaa ctttaataac      60
aaaaaataac aaaaaatatg taagctgttt tagaaacaaa aaagc                     105

<210> SEQ ID NO 86
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
agaaaagacg atgttttaga aaacaaaaag ctcaaataaa ctttaatagc caataacaaa      60
aaatatgtaa gctgttttag aaacaaaaaa gc                                    92

<210> SEQ ID NO 87
<211> LENGTH: 112
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 87
agaaaagacg atgttttaga aaacaaaaag ctcaaataaa ctttacgatg ttttagaaaa      60
caaaaagctc aaataacaaa aaatatgtaa gctgttttag aaacaaaaaa gc             112

<210> SEQ ID NO 88
<211> LENGTH: 159
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic polynucleotide"

<400> SEQUENCE: 88
agaaaagacg atgttttaga aaacaaaaag ctcatttaga aaagacgatg ttttagaaaa      60
caaaaagctg taaaaataaa ctttagaaaa gacgatgttt tagaaaacaa aaagctcaaa    120
taacaaaaaa tatgtaagct gttttagaaa caaaaaagc                           159

<210> SEQ ID NO 89
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
agaaaagacg atgtaagctc aaataaactt tagaaaagac gatgtaagct caaataacaa      60
aaaatatgta agctgtttta gaaacaaaaa agc                                 93

<210> SEQ ID NO 90
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
agaaaagacg atgtaagctc aaataaactt taatagccaa taacaaaaaa tatgtaagct      60
gttttagaaa caaaaaagc                                                 79

<210> SEQ ID NO 91
<211> LENGTH: 85
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
agaaaagacg atgttttaga aaacaaaaag ctcaaataaa ctttaataac aaaaaatatg      60
taagctgttt tagaaacaaa aaagc                                          85

<210> SEQ ID NO 92
<211> LENGTH: 86
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
agaaaagacg atgtaagctc aaataaactt tacgatgtaa gctcaaataa caaaaaatat      60
gtaagctgtt ttagaaacaa aaaagc                                         86

<210> SEQ ID NO 93

```
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 93
aagctgtttt acgatgtttt agaaaacaaa aagctcaaat aaacaaattt acgatgtaag      60
ctcaaataac aaaaaatatg taagctgttt tagaaacaaa aaagc                    105

<210> SEQ ID NO 94
<211> LENGTH: 98
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
aagctgtttt acgatgtaag ctcaaataaa caaatttaat aaactttaat aacaaaaaat      60
aacaaaaaat atgtaagctg ttttagaaac aaaaaagc                             98

<210> SEQ ID NO 95
<211> LENGTH: 105
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 95
aagctgtttt acgatgtaag ctcaaataaa caaatttacg atgttttaga aacaaaaag      60 ctcaaataac aaaaaatatg taagctgttt tagaaacaaa aaagc                   105

<210> SEQ ID NO 96
<211> LENGTH: 106
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 96
aagctgtttt aggtaacacg atgtaagctc aaataaacaa atttaggtaa cacgatgtaa      60
gctcaaataa caaaaaatat gtaagctgtt ttagaaacaa aaaagc                   106

<210> SEQ ID NO 97
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
aagctgtttt aataaacaaa tttaagctca aataacaaaa aatatgtaag ctgttttaga      60
aacaaaaaag c                                                          71
```

```
<210> SEQ ID NO 98
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
aagctgtttt aataaacaaa tttaataaca aaaatatgt aagctgtttt agaaacaaaa      60
aagc                                                                 64

<210> SEQ ID NO 99
<211> LENGTH: 98
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
aagctgtttt aagctcaaat aaacaaattt acgatgtttt agaaaacaaa aagctcaaat     60
aacaaaaaat atgtaagctg ttttagaaac aaaaaagc                            98

<210> SEQ ID NO 100
<211> LENGTH: 96
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
aagctgtttt acgctgtaag ctcaaataaa caaatttacg ccatttgtaa gctcaaataa     60
caaaaaatat gtaagctgtt ttagaaacaa aaaagc                              96

<210> SEQ ID NO 101
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
aagctgtttt aagctcaaat aaacaaattt aataacaaaa aatatgtaag ctgttttaga     60
aacaaaaaag c                                                         71

<210> SEQ ID NO 102
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
aagctcaaat aaactttaag ctcaaataac aaaaaatatg taagctgttt tagaaacaaa     60
aaagc                                                                65
```

<210> SEQ ID NO 103
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 103
aagctcaaat aaactttaat aaacaataac aaaaaatatg taagctgttt tagaaacaaa    60
aaagc                                                                65

<210> SEQ ID NO 104
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 104
aagcacaacg atgtaagctc aaataaactt taagcacaac gatgtaagct caaataacaa    60
aaaatatgta agctgtttta gaaacaaaaa agc                                 93

<210> SEQ ID NO 105
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 105
aagctcattt aagctgtaaa aataaacttt aagctcaaat aacaaaaaat atgtaagctg    60
ttttagaaac aaaaaagc                                                  78

<210> SEQ ID NO 106
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 106
aagctcattt aagctgtaaa aataaacttt aagctcattt aagcttaaaa aataacaaaa    60
aatatgtaag ctgttttaga aacaaaaaag c                                   91

<210> SEQ ID NO 107
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 107
aagctcaaat aaactttacg aaacacgatg taagctcaaa taacaaaaaa tatgtaagct    60
gttttagaaa caaaaaagc                                                 79

<210> SEQ ID NO 108
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
aagctcaaat aaactttaat aacaaaaaat atgtaagctg ttttagaaac aaaaaagc        58

<210> SEQ ID NO 109
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
aagctcaaat aaactttacg ccatttgtaa gctcaaataa caaaaaatat gtaagctgtt      60
ttagaaacaa aaaagc                                                     76

<210> SEQ ID NO 110
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
agaaaagacg atctaagctc tacgatgtaa ga                                   32

<210> SEQ ID NO 111
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
acgcaacttt agaaagaaa acgatctaag ctctacgatg taaga                      45

<210> SEQ ID NO 112
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
acgaaacttt agaaagaaa acgatctaag ctctacgatg taaga                      45

<210> SEQ ID NO 113
<211> LENGTH: 39
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 113
agaaaagacg atctacgctc tacgaataac gatgtaaga                                39

<210> SEQ ID NO 114
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
acgatctacg ctctacgaat aacgatgtaa ga                                       32

<210> SEQ ID NO 115
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
acgctctacg aataacgatg taaga                                               25

<210> SEQ ID NO 116
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
acgaataacg atgtaagacc ccagtcaggc ctaacgta                                 38

<210> SEQ ID NO 117
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
acgatgtaag accccagtca ggcctaacgt a                                        31

<210> SEQ ID NO 118
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
agaaaagacg atctacgctc tacga                                               25
```

<210> SEQ ID NO 119
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 119
agaaaagacg atctacgccc ccagtcaggc ctaacgta                    38

<210> SEQ ID NO 120
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 120
agaaaagacg accccagtca ggcctaacgt a                           31

<210> SEQ ID NO 121
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 121
acgctgtttt agaaagaaa aagctgtaat aaactttacg ctgttttaga aaagaaaaag    60
ctgtaataac aaaagtaca                                               79

<210> SEQ ID NO 122
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 122
gtacgaataa actttacgat gtaagctgta ataacaaaag taca             44

<210> SEQ ID NO 123
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 123
gtacgaataa actttaagct gtaataacaa aagtaca                     37

<210> SEQ ID NO 124
<211> LENGTH: 132
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 124
acgatggttc ttttacgatg ggttaaaaaa gctgtaagct caaataaact ttacgatggg    60
ttaacgatgg gtcttttacg atgggttaaa aaagctgtaa gctcaaataa caaaatttat   120
catcaaaagt ca                                                      132

<210> SEQ ID NO 125
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
acgaaacacg atgtaagctc atttacgaaa cgtacgaaaa ataaactttg taccaataac    60
aaaagtaca                                                           69

<210> SEQ ID NO 126
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
acgaaacacg atgtaagctc atttgtacga aaataaaact ttgtaccaat aacaaaagta    60
ca                                                                  62

<210> SEQ ID NO 127
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
gtaccaataa actttacgaa acacgatgta agctcaaata acaaaagtac a             51

<210> SEQ ID NO 128
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
gtaccaataa actttacgat gtaagctcaa ataacaaaag taca                    44

<210> SEQ ID NO 129
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
gtaccaataa actttaagct caaataacaa aagtaca                                    37

<210> SEQ ID NO 130
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
gtaccaataa actttaataa caaaagtaca                                            30

<210> SEQ ID NO 131
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131 gttatttac gaaacacgat gtaagcttaa aaacgatgta agctcaaata aactttgtac            60
caataacaaa agtaca                                                           76

<210> SEQ ID NO 132
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
acgatgtaag ctcatttgtt caaaaaataa actttacgat gtaagctcat ttacgatgta           60
agcttaaaaa ataacaaaag taca                                                  84

<210> SEQ ID NO 133
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
acgatgtaag ctcatttgtg agaaaaataa actttacgat gtaagctcaa ataacaaaag           60
taca                                                                        64

<210> SEQ ID NO 134
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134

```
acgatgtaag ctcatttgta cgaaaaataa actttgtacc aataacaaaa gtaca          55

<210> SEQ ID NO 135
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
acgatgtaag ctcatttgta cgaaaaataa actttacgat gtaagctcat ttacgatgta    60
agcttaaaaa ataacaaaag taca                                          84

<210> SEQ ID NO 136
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
acgatgtttt agaaaacaaa aagctcaaat aaactttaat aaactttaat aacaaaaaat    60 aacaaagta ca                                                        72

<210> SEQ ID NO 137
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
acgatgtttt agaaaacaaa aagctcaaat aaactttacg atgtaagctc aaataacaaa    60
agtaca                                                              66

<210> SEQ ID NO 138
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
acgatgtttt agaaaacaaa aagctcaaat aaactttaat aacaaagta ca             52

<210> SEQ ID NO 139
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
gttcaaagca gttttaagca gtaaaaataa actttaataa gtaataaaca aagtaca       57
```

```
<210> SEQ ID NO 140
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
acgatgtttt agaaaacaaa aagctcattt gtacgaaaaa taaactttac gatgtaagct      60
caaataacaa aagtaca                                                    77

<210> SEQ ID NO 141
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
acgatgtttt agaaaacaaa aagctcattt gtgagaaaaa taaactttac gatgttttag      60
aaaacaaaaa gctcaaataa caaaagtaca                                      90

<210> SEQ ID NO 142
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
acgatgtttt agaaaacaaa aagctcaaat aaactttacg atgttttaga aaacaaaaag      60
ctcaaataac aaaagtaca                                                  79

<210> SEQ ID NO 143
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
acgatgtaag ctcaaataaa ctttacgatg taagctcatt tgtgtcaaaa ataacaaaag      60
taca                                                                  64

<210> SEQ ID NO 144
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
acgatgtaag ctcaaataac atttacgatg taagctcatt tgtgtcaaaa ataaacaaag      60
taca                                                                  64
```

<210> SEQ ID NO 145
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 145
acgatgtaag ctcaaataaa ctttgtttct ttacgatgta agcttaaaaa ataacaaaag     60
taca                                                                 64

<210> SEQ ID NO 146
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 146
acgatgtaag ctcaaataaa ctttaggggt tacgatgtaa gctcaaataa caaaagtaca     60

<210> SEQ ID NO 147
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 147
acgatgtaag ctcaaataaa ctttaataaa gaataaacaa taacaaaagt aca            53

<210> SEQ ID NO 148
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 148
acgatgtaag ctcaaataaa ctttaataaa ctttaataac aaaaaataac aaaagtaca      59

<210> SEQ ID NO 149
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 149
acgatgtaag ctcaaataaa ctttgtttca ataacaaaag taca                     44

<210> SEQ ID NO 150
<211> LENGTH: 46
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 150
acgatgtaag ctcaaataaa ctttaagctc aaataacaaa agtaca                   46

<210> SEQ ID NO 151
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
acgatgtaag ctcaaataaa ctttacgatg taagctcaaa taacaaaagt aca           53

<210> SEQ ID NO 152
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
acgatgtaag ctcaaataaa ctttacgatg taagctcatt tgtgcgaaaa ataacaaaag    60
taca                                                                 64

<210> SEQ ID NO 153
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
acgatgtaag ctcaaataaa ctttacgatg taagctcatt tacgaaacgt gcgaaaata     60 acaaaagtac a                                                         71

<210> SEQ ID NO 154
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
acgatgtaag ctcaaataaa ctttacgaaa cacgatgtaa gctcatttgt gcgaaaata     60 acaaaagtac a                                                         71

<210> SEQ ID NO 155
<211> LENGTH: 98
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 155
acgatgtaag ctcatttagg cggtacgatg taagctgtaa aaataaactt taggcggtac    60
gatgtaagct catttgtggt aaaaataaca aaagtaca                            98

<210> SEQ ID NO 156
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
acgatgtaag ctcatttgtg gaaaaaataa actttaggcg gtacgatgta agctcatttg    60
tgcgaaaaat aacaaaagta ca                                             82

<210> SEQ ID NO 157
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
acgatgtaag ctcatttacg atgtaagctg taaaaataaa ctttaggcgg tacgatgtaa    60
gctcatttgt ggtaaaaata acaaaagtac a                                   91

<210> SEQ ID NO 158
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
acgatgtaag ctcatttgta cgaaaaataa actttaagct caaataacaa aagtaca       57

<210> SEQ ID NO 159
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
acgatgtaag ctcatttgta cgaaaaataa actttacgat gtaagctcaa ataacaaaag    60
taca                                                                 64

<210> SEQ ID NO 160
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160

```
gtacgaataa actttaataa caaaagtaca                                       30

<210> SEQ ID NO 161
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
acgatgtaag ctctacgatg taagctcaaa taaactttac gatgtaagct caaataacaa     60
aagtaca                                                               67

<210> SEQ ID NO 162
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 162
acgatgtaag ctctacgatg taagctcatt tacgatgtaa gctgtaaaaa taaactttac     60
gatgtaagct ctacgatgta agctcattta cgatgtaagc tctgtgcgaa aaataacaaa    120
agtaca                                                               126

<210> SEQ ID NO 163
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
acgctgtttt agaaaacaaa aagctcaaat aaactttagg cggtgtttca ataacaaaag     60
taca                                                                  64

<210> SEQ ID NO 164
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
acgctgtttt agaaaacaaa aagctcaaat aaactttaat aacaaagta ca              52

<210> SEQ ID NO 165
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
``` acgctgttttt agaaaacaaa aagctcaaat aaactttgtt tcaataacaa aagtaca    57

<210> SEQ ID NO 166
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166 acgctgttttt agaaaacaaa aagctcaaat aaactttgta ccaataacaa aagtaca    57

<210> SEQ ID NO 167
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
acgccatttg taagctcaaa taaactttaa taaacaataa caaaagtaca              50

<210> SEQ ID NO 168
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
acgccatttg taagctcaaa taaactttgt ttcaataaca aaagtaca                48

<210> SEQ ID NO 169
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
acgccatttg taagctcaaa taaactttag gcggtacgat gtaagctcaa ataacaaaag   60
taca                                                                64

<210> SEQ ID NO 170
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
acgccatttg taagctcaaa taaactttag gcgttacgat gtaagctcaa ataacaaaag   60
taca                                                                64

<210> SEQ ID NO 171
<211> LENGTH: 57

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
acgctgtaag ctcaaataaa ctttaagctc atttgtgtca aaataacaa aagtaca        57

<210> SEQ ID NO 172
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
gtttcaataa actttaagct catttaagct taaaaaataa caaaagtaca               50

<210> SEQ ID NO 173
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
gtttcaataa actttaataa caaaagtaca                                     30

<210> SEQ ID NO 174
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
gtttcaataa actttaggcg ttacgatgta agctcaaata acaaaagtac a             51

<210> SEQ ID NO 175
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
gtttcaataa actttacgcc atttgtaagc tcaaataaca aaagtaca                 48

<210> SEQ ID NO 176
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
```
gtttcaataa actttacgat gtaagctcat ttgtgcgaaa aataacaaaa gtaca    55

<210> SEQ ID NO 177
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
gtttcaataa actttacgat gtaagctcaa ataacaaaag taca    44

<210> SEQ ID NO 178
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
gtttctttac gatgtaagct gtaaaaataa actttacgct gtaagctcat ttgtgcgaaa    60
aataacaaaa gtaca    75

<210> SEQ ID NO 179
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
gtttctttgt cctaaaaata aactttacga tgtaagctca aataacaaaa gtaca    55

<210> SEQ ID NO 180
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
acgctgtaag ctcatttacg atgtaagctg taaaaataaa ctttacgctg taagctcatt    60
tgtgtcaaaa ataacaaaag taca    84

<210> SEQ ID NO 181
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
gttgaaataa actttaagct catttaagct taaaaaataa caaaagtaca    50

<210> SEQ ID NO 182
<211> LENGTH: 70

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
gtttctttaa gctgtaaaaa taaactttac gctgtaagct catttaagct taaaaaataa        60
caaaagtaca                                                              70

<210> SEQ ID NO 183
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
gtttctttaa gctgtaaaaa taaactttaa gctcaaataa caaaagtaca                   50

<210> SEQ ID NO 184
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
gtttcaataa actttacgct gtaagctcaa ataacaaaag taca                        44

<210> SEQ ID NO 185
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
gttgtaataa actttaataa caaaagtaca                                        30

<210> SEQ ID NO 186
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
gttggaataa actttgttgc aataacaaaa gtaca                                  35

<210> SEQ ID NO 187
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 187
gttggaataa actttagaaa agacgatgtt ttagaaaaca aaaagctcaa ataacaaaag    60
taca                                                                64

<210> SEQ ID NO 188
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
gttggaataa actttaataa actttaataa caaaaaataa caaaagtaca              50

<210> SEQ ID NO 189
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
gttggaataa actttaatag ccaataacaa aagtaca                            37

<210> SEQ ID NO 190
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
gttggaataa actttacgat gttttagaaa acaaaaagct caaataacaa aagtaca      57

<210> SEQ ID NO 191
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
gttggtttag aaaaggtgag aaaaataaac tttagaaaag acgatgtttt agaaaacaaa   60
aagctcaaat aacaaaagta ca                                            82

<210> SEQ ID NO 192
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
gttgcaataa actttagaaa agacgatgta agctcaaata acaaaagtac a            51
```

-continued

```
<210> SEQ ID NO 193
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
gttgcaataa actttaatag ccaataacaa aagtaca                              37

<210> SEQ ID NO 194
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
gttggaataa actttaataa caaaagtaca                                      30

<210> SEQ ID NO 195
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
gttgcaataa actttacgat gtaagctcaa ataacaaaag taca                      44

<210> SEQ ID NO 196
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
aagctgtttt acgatgtttt agaaaacaaa aagctcaaat aaacaaattt acgatgtaag     60
ctcaaataac aaaagtaca                                                  79

<210> SEQ ID NO 197
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
aagctgtttt acgatgtaag ctcaaataaa caaatttaat aaactttaat aacaaaaaat     60
aacaaaagta ca                                                         72

<210> SEQ ID NO 198
<211> LENGTH: 79
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"

<400> SEQUENCE: 198
aagctgtttt acgatgtaag ctcaaataaa caaatttacg atgttttaga aaacaaaaag    60
ctcaaataac aaaagtaca                                                 79

<210> SEQ ID NO 199
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
aagctgtttt aggtaacacg atgtaagctc aaataaacaa atttaggtaa cacgatgtaa    60 gctcaaaataa caaaagtaca                                               80

<210> SEQ ID NO 200
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
aagctgtttt aataaacaaa tttaagctca ataacaaaa gtaca                     45

<210> SEQ ID NO 201
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
aagctgtttt aataaacaaa tttaataaca aaagtaca                            38

<210> SEQ ID NO 202
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
aagctgtttt aagctcaaat aaacaaattt acgatgtttt agaaaacaaa aagctcaaat    60
aacaaaagta ca                                                        72

<210> SEQ ID NO 203
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
aagctgtttt gtttcaataa acaaatttac gccatttgta agctcaaata acaaaagtac    60
a    61

<210> SEQ ID NO 204
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
aagctgtttt aagctcaaat aaacaaattt aataacaaaa gtaca    45

<210> SEQ ID NO 205
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
aagctcaaat aaactttaag ctcaaataac aaaagtaca    39

<210> SEQ ID NO 206
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
aagctcaaat aaactttaat aaacaataac aaaagtaca    39

<210> SEQ ID NO 207
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
aagcacaacg atgtaagctc aaataaactt taagcacaac gatgtaagct caaataacaa    60
aagtaca    67

<210> SEQ ID NO 208
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
aagctcattt aagctgtaaa aataaacttt aagctcaaat aacaaaagta ca    52

```
<210> SEQ ID NO 209
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
aagctcattt aagctgtaaa aataaacttt aagctcattt aagcttaaaa aataacaaaa    60
gtaca                                                                65

<210> SEQ ID NO 210
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
aagctcaaat aaactttgta ccaataacaa aagtaca                              37

<210> SEQ ID NO 211
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
aagctcaaat aaactttaat aacaaaagta ca                                   32

<210> SEQ ID NO 212
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
aagctcaaat aaactttacg ccatttgtaa gctcaaataa caaaagtaca                50

<210> SEQ ID NO 213
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
aatgatacgg cgaccaccga agaaaagacg atctaagctc tacgatgtaa gacacgtctg    60
aactccagtc ac                                                        72

<210> SEQ ID NO 214
<211> LENGTH: 83
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 214
aatgatacgg cgaccaccga acgcaacttt agaaaagaaa acgatctaag atctacgatg    60
taacacgtct gaactccagt cac                                           83

<210> SEQ ID NO 215
<211> LENGTH: 85
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
aatgatacgg cgaccaccga acgaaacttt agaaaagaaa acgatctaag ctctacgatg    60
taagacacgt ctgaactcca gtcac                                         85

<210> SEQ ID NO 216
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
aatgatacgg cgaccaccga aagaaaagac gatctacgct ctacgaataa cgatgtaaga    60
cacgtctgaa ctccagtcac                                               80

<210> SEQ ID NO 217
<211> LENGTH: 73
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
aatgatacgg cgaccaccga aacgatctac gctctacgaa taacgatgta agacacgtct    60
gaactccagt cac                                                      73

<210> SEQ ID NO 218
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
aatgatacgg cgaccaccga acgctctacg aataacgatg taagacacgt ctgaactcca    60
gtcac                                                               65

<210> SEQ ID NO 219
<211> LENGTH: 79
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
aatgatacgg cgaccaccga aacgaataac gatgtaagac cccagtcagg cctaacgtac      60
acgtctgaac tccagtcac                                                  79

<210> SEQ ID NO 220
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
aatgatacgg cgaccaccga aacgatgtaa gaccccagtc aggcctaacg tacacgtctg      60
aactccagtc ac                                                         72

<210> SEQ ID NO 221
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
aatgatacgg cgaccaccga agaaaagac gatctacgct ctacgacacg tctgaactcc       60
agtcac                                                                66

<210> SEQ ID NO 222
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
aatgatacgg cgaccaccga aagaaaagac gatctacgcc cccagtcagg cctaacgtac      60
acgtctgaac tccagtcac                                                  79

<210> SEQ ID NO 223
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
aatgatacgg cgaccaccga aagaaaagac gaccccagtc aggcctaacg tacacgtctg      60
aactccagtc ac                                                         72

<210> SEQ ID NO 224
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 224
aatgatacgg cgaccaccga a                                              21

<210> SEQ ID NO 225
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 225
gtgactggag ttcagacgtg                                                20

<210> SEQ ID NO 226
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
aatgatacgg cga                                                       13

<210> SEQ ID NO 227
<211> LENGTH: 85
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 227
gtgactggag ttcagacgtg tcttacatcg tagagcttag atcgttttct tttctaaagt    60
tgcgttcggt ggtcgccgta tcatt                                          85

<210> SEQ ID NO 228
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
ccaccgaacg caactttaga aaagaaaacg atctaagctc tacgatgtaa gacacgtctg    60
aactc                                                                65

<210> SEQ ID NO 229
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"

<400> SEQUENCE: 229
aatgatacgg cgaccaccga acgcaacttt agaaaagaaa acgatctaag ctctacgatg    60
taagacacgt ctgaactc                                                  78

<210> SEQ ID NO 230
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 230
gagtctacug ctutacutcg agactcaatg                                     30
```

DNA-GLYCAN CONJUGATES AND METHODS OF USE

CROSS-REFERENCE TO RELATED APPLICATIONS

This application is the § 371 U.S. National Stage of International Application No. PCT/US2018/035629, filed Jun. 1, 2018, which claims the benefit of U.S. Provisional Application Ser. No. 62/514,419, filed Jun. 2, 2017, each of which are incorporated herein by reference.

SEQUENCE LISTING

The instant application contains a Sequence Listing which has been submitted electronically in ASCII format and is hereby incorporated by reference in its entirety. Said ASCII copy, created on May 31, 2018, is named 548_00010201_SL.txt and is 71,886 bytes in size.

BACKGROUND

Complex carbohydrates, often referred to as glycans, are one of the most abundant molecules present in living organisms, and they play important roles in biological events such as molecular recognition, adhesion, pathogenesis, and inflammation (Chevolot et al., 2007, Angewandte Chemie 46(14):2398-402). Expression patterns of complex carbohydrates are widely altered in cancer, retrovirus infection, atherosclerosis, thrombosis, diabetes, neurodegeneration, arthritis and other diseases (Fernandez-Tejada et al., 2015, Chemistry 21(30):10616-28). Polysaccharides form a major portion of antigenic structures, along with other microbe-derived molecules, to which host cells recognize and respond (Wang et al., 2002, Nature biotechnology 20(3): 275-281). The pivotal role of glycans in molecular recognition and signaling makes them of important diagnostic and therapeutic value (Fernandez-Tejada et al., 2015, Chemistry 21(30):10616-28).

At present, the most prevalent methods in the study of glycan-protein interactions include carbohydrate microarrays (Wang et al., 2002, Nature biotechnology 20(3):275-281; Song et al., 2015, Glycoconjugate J 32(7):465-473), surface plasmon resonance (Mercey et al., 2008, Analytical chemistry 80(9):3476-3482), isothermal calorimetry (Turnbull et al., 2004, Journal of the American Chemical Society 126(4):1047-1054), glycosylated conductive polymer (Zeng et al., 2016, Acc Chem Res 2016, 49 (9):1624-33), enzyme-linked lectin assay (Lambré et al., 1990, Journal of immunological methods 135(1):49-57), and crystallographic studies (Merritt et al., 1998, Journal of molecular biology 282(5):1043-1059). Carbohydrate researchers have used the microarray with a wide range of carbohydrate derivatives by various means of immobilization technology (Wang et al., 2002, Nature biotechnology 20(3):275-281; Zhang et al., 2006, Analytical chemistry 78(6):2001-2008; Ban et al., 2012, Nature chemical biology 8(9):769-773). However, all the methods listed have their limitations and depend on immobilized sugars that do not exactly mimic the biological environment of binding. In addition, the tagging of the target, the glycan modifications, or the specific antibody interactions are required for the detection. Moreover, interactions of glycans with targets are usually weak, and often it is challenging to generate a sugar library having a glycodendrimer to place on the slide with optimum distance for specific binding.

SUMMARY OF THE APPLICATION

Though the importance of glycans is well accepted, systematic study of the structures and functions of carbohydrates, also known as functional glycomics, is yet to reach the level attained by genomics and proteomics. Taking the advantage of template driven biosynthesis of DNA/RNA and proteins, eventually researchers adopted this knowledge to the synthesis and analysis of these molecules. But a similar scheme of free-flowing information is not available in carbohydrate study and this is attributed to the many unique challenges in functional glycomics. For instance, glycans are less organized without a template driven machinery, and it is necessary to have a method developed for the synthesis and analysis of each glycan. Recent advances in solid phase automated synthesis and enzymatic synthesis have eased the difficulties in obtaining a variety of glycans, but materials available for experimentation remain difficult to obtain, especially for complex glycans. Hence, the development of a highly versatile and ultra-sensitive detection technology is particularly important in the field of carbohydrate research for the characterization of glycan-protein interactions.

Provided herein is a DNA-glycan conjugate that includes a glycan. The glycan includes a glycan structure of at least two carbohydrate monomers where each carbohydrate monomer is attached to at least one other carbohydrate monomer by a glycosidic linkage. The DNA-glycan conjugate also includes a polynucleotide covalently attached to the glycan, where the polynucleotide includes a plurality of modules. Each module includes a nucleotide string, and the plurality of modules includes a monomer module and a linkage module. A monomer module corresponds to each carbohydrate monomer present in the DNA-glycan conjugate, and a linkage module corresponds to each glycosidic linkage present between each carbohydrate monomer in the DNA-glycan conjugate. The nucleotide sequence of the plurality of modules corresponds to the glycan structure.

In one embodiment, a carbohydrate monomer of the glycan identified by a monomer module is selected from Table 1. In one embodiment, each linkage module identifies a glycosidic linkage that includes an anomeric configuration and linkage position of each glycosidic linkage, and the glycosidic linkage is selected from Table 2.

The glycan of a DNA-glycan conjugate can include a sequence of at least 3 carbohydrate monomers where at least 2 of the carbohydrate monomers are joined by a branch. In such an embodiment the plurality of modules also includes a branch beginning module and a branch ending module corresponding to each branch present in the DNA-glycan conjugate, and the branch is selected from Table 2.

In one embodiment, a carbohydrate monomer includes a modification. In such an embodiment the plurality of modules also includes a modification module corresponding to each modification present in the DNA-glycan conjugate. Each modification module identifies a modification to a carbohydrate monomer, and the modification is selected from Table 3.

In one embodiment, the nucleotide string of each module is at least 3 nucleotides and no greater than 5 nucleotides. In one embodiment, the polynucleotide includes DNA nucleotides. In one embodiment, the polynucleotide further includes a nucleotide sequence corresponding to a forward primer and a nucleotide sequence corresponding to a reverse primer.

In one embodiment, the covalent attachment between the glycan and the polynucleotide includes an organic group. In one embodiment, the glycan is covalently attached to the 5' end or the 3' end of the polynucleotide. In one embodiment, the glycan is covalently attached to one or more nucleotides that are not at a terminal end of the polynucleotide. In one embodiment, the polynucleotide is covalently attached to the reducing end of the glycan. In one embodiment, the polynucleotide is covalently attached to the glycan as an alpha or a beta linkage.

Also provided herein is a library of DNA-glycan conjugates. In one embodiment, the library includes at least 3 different DNA-glycan conjugates. In one embodiment, each polynucleotide of each DNA-glycan conjugate includes a first primer and a second primer. The nucleotide sequence of first primer can be the same on each DNA-glycan conjugate, and the nucleotide sequence of second primer can be the same on each DNA-glycan conjugate.

Further provided herein is a composition. In one embodiment, composition includes the a DNA-glycan conjugate, or a library of DNA-glycan conjugates.

Also provided is a kit that includes a DNA-glycan conjugate, or a library of DNA-glycan conjugates, for using the same.

Provided herein are methods for using a DNA-glycan conjugate or a library of DNA-glycan conjugates. The method can include identifying a glycan-binding compound. In one embodiment, the method includes contacting a portion of a sample suspected of including one or more glycan-binding compounds with a DNA-glycan conjugate to result in a mixture. The sample can be one that is suspected of including a glycan-binding compound that will bind the DNA-glycan conjugate. The contacting is under conditions suitable for binding of the glycan-binding compound and the DNA-glycan conjugate to form a complex. The method further includes identifying a DNA-glycan conjugate bound to the glycan-binding compound. In one embodiment, the sample does not include a glycan-binding compound that will bind a DNA-glycan conjugate present in the mixture, and a DNA-glycan conjugate bound to the glycan-binding compound is not identified.

The method can further include contacting a second portion of the sample with a second DNA-glycan conjugate to result in a mixture, where the sample is suspected of including a second glycan-binding compound that will bind the second DNA-glycan conjugate. The contacting is under conditions suitable for binding of the second glycan-binding compound to the second DNA-glycan conjugate. The method further includes identifying whether the second DNA-glycan conjugate binds the second glycan-binding compound.

In one embodiment, the method includes contacting a sample suspected of including a plurality of glycan-binding compounds with a plurality of DNA-glycan conjugates to result in a mixture, where the sample is suspected of including at least one glycan-binding compound that will bind a DNA-glycan conjugate. The contacting is under conditions suitable for binding a glycan-binding compound of the sample to a DNA-glycan conjugate. The method further includes identifying DNA-glycan conjugates bound to glycan-binding compounds. In one embodiment, the sample does not include a glycan-binding compound that will bind a DNA-glycan conjugate present in the mixture, and a DNA-glycan conjugate bound to the glycan-binding compound is not identified.

In one embodiment, the sample includes a biological sample, such as blood. In one embodiment, the glycan-binding compound includes a protein, such as an antibody.

In one embodiment, the identifying includes amplification of the polynucleotide attached to the DNA-glycan conjugate bound to the glycan-binding compound. The amplification can include a polymerase chain reaction (PCR), such as a quantitative PCR (qPCR). In one embodiment, the identifying can include amplifying by qPCR the polynucleotide attached to the DNA-glycan conjugate bound to the glycan-binding compound and the polynucleotide attached to another DNA-glycan conjugate bound to another glycan-binding compound, determining a critical threshold (Ct) value of each amplification reaction, comparing the Ct of each amplification reaction. In one embodiment, the identifying includes determining the nucleotide sequence of the polynucleotide attached to the DNA-glycan conjugate bound to the glycan-binding compound. In one embodiment, the identifying can include reducing the number of DNA-glycan conjugates present in the composition that are not bound to a glycan-binding compound.

Also provided herein is a kit. In one embodiment, a kit is for identifying a DNA-glycan conjugate bound to a glycan-binding compound. The kit includes, in separate containers, a DNA-glycan conjugate and primers for amplification of the polynucleotide of the DNA-glycan conjugate. In one embodiment, a kit is for identifying the blood group of a sample, and includes in separate containers DNA-glycan conjugates, where separate DNA-glycan conjugates include glycans that include a blood group; and primers for amplification of the polynucleotides of the DNA-glycan conjugates. In one embodiment, the blood group is selected from A blood group, B blood group, the O group, blood group P, blood group p1, blood group Pk, blood group FORS1, blood group LKE, blood group I, and blood group I.

The present disclosure also includes a computer-implemented method for converting data from a glycan structure to a nucleotide sequence. The method can include providing a glycan structure, and generating a nucleotide sequence based on the glycan structure, where the nucleotide sequence is representative of the glycan structure. The method can further include providing one or more datasets to generate the nucleotide sequence based on the glycan structure, where generating the nucleotide sequence based on the glycan structure includes generating the nucleotide sequence based on the glycan structure and the one or more datasets. The glycan structure includes at least two carbohydrate monomers and at least one glycosidic linkage, where generating the nucleotide sequence based on the glycan structure includes generating a portion of the nucleotide sequence in response to the at least two carbohydrate monomers and the at least one glycosidic linkage of the glycan structure. In one embodiment, the glycan structure includes at least one branch, where generating the nucleotide sequence based on the glycan structure includes generating a portion of the nucleotide sequence in response to the at least one branch of the glycan structure. In one embodiment, the glycan structure includes at least one modification, where generating the nucleotide sequence based on the glycan structure includes generating a portion of the nucleotide sequence in response to the at least one modification of the glycan structure.

Also provided is a computer-implemented method for translating data from a nucleotide sequence to a glycan structure. The method includes providing a nucleotide sequence, and generating a glycan structure based on the nucleotide sequence, where the glycan structure is encoded by the nucleotide sequence. The method can further include providing one or more datasets to generate the glycan structure based on the nucleotide sequence, where generating the glycan structure based on the nucleotide sequence includes generating the glycan structure based on the nucleotide sequence and the one or more datasets. The nucleotide sequence includes oligonucleotides, where each oligonucleotide is representative of a characteristic of the glycan structure, wherein generating the glycan structure based on the nucleotide sequence includes generating the glycan structure in response to the oligonucleotides present in the nucleotide sequence and the one or more datasets. In one embodiment, the characteristic is a glycan substructure, a carbohydrate monomer, a glycosidic linkage, a modification, or a branch. In one embodiment, the nucleotide sequence includes an oligonucleotide representative of a glycan substructure, wherein generating the glycan structure based on the nucleotide sequence includes generating a portion of the glycan structure in response to the oligonucleotide representative of a glycan substructure. In one embodiment, the nucleotide sequence includes an oligonucleotide representative of a carbohydrate monomer, where generating the glycan structure based on the nucleotide sequence includes generating a portion of the glycan structure in response to the oligonucleotide representative of a carbohydrate monomer. In one embodiment, the nucleotide sequence includes an oligonucleotide representative of a glycosidic linkage, where generating the glycan structure based on the nucleotide sequence includes generating a portion of the glycan structure in response to the oligonucleotide representative of a glycosidic linkage. In one embodiment, the nucleotide sequence includes an oligonucleotide representative of a modification, where generating the glycan structure based on the nucleotide sequence includes generating a portion of the glycan structure in response to the oligonucleotide representative of a modification. In one embodiment, the nucleotide sequence includes an oligonucleotide representative of a branch, where generating the glycan structure based on the nucleotide sequence includes generating a portion of the glycan structure in response to the oligonucleotide representative of a branch.

Further provided herein is a system for converting data from a glycan structure to a nucleotide sequence. The system includes an input apparatus to enter a glycan structure, an output apparatus to output a nucleotide sequence representative of the glycan structure, and a computing apparatus including one or more processors. The computer apparatus operably coupled to the input apparatus and configured to receive the glycan structure using the input apparatus, and generate a nucleotide sequence based on the glycan structure using one or more datasets.

In one embodiment, the system further includes an output apparatus to output a nucleotide sequence representative of the glycan structure. In one embodiment, the output apparatus includes a DNA synthesizer to produce a polynucleotide based on the generated nucleotide sequence, where the computing apparatus is operably coupled to the DNA synthesizer and is further configured to direct the production of the polynucleotide based on the generated nucleotide sequence. In one embodiment, the output apparatus includes a display to depict the generated nucleotide sequence.

Also provided herein is a system for translating data from a nucleotide sequence to a glycan structure. The system includes an input apparatus to enter a nucleotide sequence, an output apparatus to output a glycan structure encoded by the nucleotide sequence, and a computing apparatus including one or more processors. The computer apparatus operably coupled to the input apparatus and configured to receive the nucleotide sequence using the input apparatus, and generate a glycan structure encoded by the glycan structure using one or more datasets. In one embodiment, the system further includes an output apparatus to output a glycan structure encoded by the nucleotide sequence. In one embodiment, the output apparatus includes a display to depict the generated glycan structure.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

While the polynucleotide sequences described herein are listed as DNA sequences, it is understood that the complements, reverse sequences, and reverse complements of the DNA sequences can be easily determined by the skilled person. It is also understood that the sequences disclosed herein as DNA sequences can be converted from a DNA sequence to an RNA sequence by replacing each thymidine nucleotide with a uridine nucleotide.

In the description herein particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The following detailed description of illustrative embodiments of the present disclosure may be best understood when read in conjunction with the following drawings.

FIG. 14a. DNA Encoded Blood Glycans. FIG. 14b qPCR limit of detection comparison of glycan DNA conjugate and pure DNA. FIG. 14c. Each G+DNA conjugate selected against the mixture of antibodies composing equal concentration of Ab A, Ab B and Ab O. FIG. 14d. G2+B DNA selected against each antibody separately.

FIG. 17 shows a standard curve plot of pure DNA (B DNA) and glycan conjugated B DNA (S+B DNA).

FIG. 23a, ELISA of glycans-biotin immobilized on avidin coated surface against VK9. FIG. 23b, ELISA of glycans-DNA codes immobilized via pierce DNA coating solution against VK9.

FIG. 31A-C show an example of fabrication of a DNA-glycan conjugate by glycan code ligation. FIG. 31A shows a schematic of the steps. FIG. 31B shows an example of the steps of FIG. 31A. FIG. 31B discloses SEQ ID NOS 226, 226, 226-227, 226-229 and 227, respectively, in order of appearance. FIG. 31C shows an example of using Gb-4 in the fabrication of a DNA-glycan conjugate by glycan code ligation and a MALDI-TOF trace of the resulting product. FIG. 31C discloses SEQ ID NOS 226, 226 and 226, respectively, in order of appearance.

FIG. 32A shows an example of a multivalent headpiece. FIG. 32A discloses SEQ ID NO: 230. FIG. 32B shows click conjugation and DNA ligation for the multivalent glycan presented DEGL.

DETAILED DESCRIPTION OF ILLUSTRATIVE EMBODIMENTS

Glycans

Figure 1:
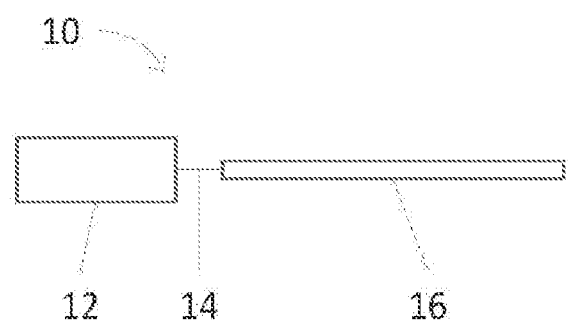
FIG. 1 is a schematic drawing of one embodiment of a DNA-glycan conjugate according to the present disclosure.

A DNA-glycan conjugate includes one or more glycans and a covalently attached polynucleotide. As used herein, the term "glycan" refers to a compound having at least one carbohydrate monomer (e.g., one, at least 2, at least 3, at least 4, etc.). A glycan can be a homopolymer or heteropolymer of carbohydrate monomers, and can be linear or branched. In one embodiment, the number of carbohydrate monomers in a glycan described herein can be as high as 50. As used herein, "carbohydrate monomer," "monomer," "monosaccharide," and "sugar" are used interchangeably. A carbohydrate monomer present in a glycan described herein is typically in a closed ring form. A carbohydrate monomer can be natural or non-natural (e.g., it is not known to exist in nature). A glycan can be obtained from a natural source, or synthesized. In those embodiments where a DNA-glycan conjugate has more than one glycan, referred to herein as a multivalent DNA-glycan conjugate, each glycan is the same.

The number of glycans can be at least 1, at least 2, at least 3, at least 4, at least 5, at least 6, at least 7, at least 8, at least 9, or at least 10. In one embodiment, the number of glycans that are part of a multivalent DNA-glycan conjugate is no greater than 15. Unless stated otherwise, reference herein to a DNA-glycan conjugate includes DNA-glycan conjugates with one or more glycans, e.g., both monovalent and multivalent DNA-glycan conjugates.

A glycan has a specific glycan structure. As used herein, a "glycan structure" refers to the individual components of a glycan, including the carbohydrate monomers, the way they are connected, any modifications of the carbohydrate monomers, and the location of any branches in the glycan. A glycan structure can be represented in any format that indicates the individual components of a glycan. Typically, the format used is the one set out by the International Union of Pure and Applied Chemistry (IUPAC) or the Consortium for Functional Glycomics (CFG). The IUPAC format includes a linear description of a glycan. Rules for using the IUPAC format to describe a glycan can be found at IUPAC-IUB Joint Commission on Biochemical Nomenclature, Polysaccharide Nomenclature, Recommendations 1980 (1982, Eur. J. Biochem. 126:439-441), and McNaught (1996, Pure and Applied Chemistry 68(10): 1919-2008). The CFG format includes a symbol nomenclature to describe a glycan. Rules for using the CFG format to describe a glycan can be found at Varki, et al. (2009, Proteomics 9(24): 5398-5399), Harvey et al. (2011, Proteomics 11(22): 4291-4295), and on the world wide web at functionalglycomics.org/static/consortium/Nomenclature.shtml.

Any type of carbohydrate monomer can be part of a glycan present in a DNA-glycan conjugate described herein. The number of carbons in a carbohydrate monomer can be 2, 3, 4, 5, 6, 7, 8, or 9. Non-limiting examples of carbohydrate monomers include those listed in Table 1. Unless noted otherwise, carbohydrate monomers are in the D-configuration.

TABLE 1

Monosaccharides and their codes (library A).

| S.No | Sugar Monomer | Sugar Name | DNA Code (as in dictionary) |
|---|---|---|---|
| 1 | All | Allose | AAAA |
| 2 | AllNAc | N-Acetyl-Allosamine | AAAC |
| 3 | AllN | Allosamine | AAAG |
| 4 | AllA | Alluronic Acid | AAAT |
| 5 | Alt | Altrose | AACA |
| 6 | AltNAc | N-Acetyl-Altrosamine | AACC |
| 7 | AltN | Alltrosamine | AACG |
| 8 | AltA | Alturonic Acid | AACT |
| 9 | Gl | Glucose | AAGA |
| 10 | GlcNAc | N-Acetyl-Glucosamine | AAGC |
| 11 | GlcN | Glucosamine | AAGG |
| 12 | GlcA | Glucoronic Acid | AAGT |
| 13 | Man | Mannose | AATA |
| 14 | ManNAc | N-Acetyl-Mannosamine | AATC |
| 15 | ManN | Mannosamine | AATG |
| 16 | ManA | Mannuronic Acid | AATT |
| 17 | Gul[GuL]] | Gulose | ACAA |
| 18 | GulNAc | N-Acetyl-Gulosamine | ACAC |
| 19 | GulN | Gulosamine | ACAG |
| 20 | GulA | Guluronic Acid | ACAT |
| 21 | Ido | Idose | ACCA |
| 22 | IdoNAc | N-Acetyl-Idosamine | ACCC |
| 23 | IdoN | Idosamine | ACCG |
| 24 | IdoA | Idouronic Acid | ACCT |
| 25 | Gal | Galactose | ACGA |
| 26 | GalNAc | N-Acetyl-Galactosamine | ACGC |
| 27 | GalN | Galactosamine | ACGG |
| 28 | GalA | Galacturonic Acid | ACGT |
| 29 | Tal | Talose | ACTA |
| 30 | TalNAc | N-Acetyl-Talosamine | ACTC |
| 31 | TalN | Talosamine | ACTG |
| 32 | TalA | Taluronic Acid | ACTT |
| 33 | Tag | Tagatose | ATCG |
| 34 | TagA | Tagaturonic Acid | ATCT |
| 35 | Hep | Heptose | ATCG |
| 36 | DDManHep | D-Glycero-DMannoHeptose | ATGG |
| 37 | Dha | 3-deoxy-D-lyxo-heptulosaric | ATGT |
| 38 | LDManHep | L-glycero-D-mannoheptose | ATTA |
| 39 | Fuc | Fucose | AGAA |
| 40 | FucNAc | N-acetyl-L-fucosamine | AGAC |
| 41 | FucN | Fucosamine | AGAG |
| 42 | Qui | Quinovose | AGAT |
| 43 | QuiNAc | N-acetyl-D-quinovosamine | ATAA |
| 44 | QuiN | Quinovosamine | ATAC |
| 45 | Rha | Rhamnose | ATAG |
| 46 | RhaNAc | N-acetyl-L-rhamnosamine | ATAT |
| 47 | RhaN | Rhamnosamine | ATCA |
| 48 | Tyv | Tyvelose | ATTC |
| 49 | Oli | Olivose | ATTG |
| 50 | Par | Paratose | ATTT |
| 51 | Dig | Digitoxose | CAAA |

TABLE 1-continued

Monosaccharides and their codes (library A).

| S.No | Sugar Monomer | Sugar Name | DNA Code (as in dictionary) |
|---|---|---|---|
| 52 | 6dAlt | 6-deoxy-L-altrose | CAAC |
| 53 | 6dTal | 6-deoxy-D-talose | CAAG |
| 54 | Abe | Abequose | CAAT |
| 55 | Api | Apiose | CACA |
| 56 | Co | Colitose | CACC |
| 57 | Neu5Ac | N-acetylneuraminic | AGGC |
| 58 | Neu5GC | N-glycolylneuraminic acid | AGGG |
| 60 | Kdo | 3-Deoxy-D-manno-octulosonic | ATCC |
| 61 | Mur | Muramic acid | CACG |
| 62 | MurNAc | N-acetylmuramic acid | CACT |
| 63 | MurNGc | N-glycolylmuramic acid | CCAA |
| 64 | Sia | Sialic Acid | CCAG |
| 65 | Neu | Neuraminic acid | CCAC |
| 66 | Fru | Fructose | ATGA |
| 67 | Sor | Sorbose | ATGC |
| 68 | Psi | Psicose | ATAA |
| 69 | Rib | Ribose | GGGG |
| 70 | Ara | Arabinose | ATAT |
| 71 | Xyl | Xylose | ATCA |
| 72 | Lyx | Lyxose | ATCT |
| 73 | Bae | Bacillosamine | CCAT |
| 74 | R | For extending a short nucleotide | CCCCAGTCAGGCCTAACGTA (SEQ ID NO: 1) |

Each monomer is attached to at least one other monomer by a glycosidic linkage. As used herein, a "glycosidic linkage" refers to two characteristics, (i) the position or configuration of the anomeric carbon of a monomer and (ii) the linkage position between the anomeric carbon of the monomer and the carbon bearing the connecting oxygen of the following monomer. The position or configuration of the anomeric carbon is designated alpha (α) or beta ((β).

In the α anomer, the —OH substituent on the anomeric carbon rests on the opposite side (trans) of the ring from the $CH_2OH$ side branch. In the β anomer, the —OH substituent on the anomeric carbon rests on the same side (cis) of the plane of the ring as the —$CH_2OH$ side branch. In the notation sometimes used herein, the letter "a" is used to designate an alpha bond and the letter "b" is used to designate a beta bond. The anomeric carbon of a carbohydrate monomer can be either carbon C-1 or carbon C-2.

The linkage position refers to the anomeric carbon of a first carbohydrate monomer and the number of the carbon bearing the connecting oxygen of the following carbohydrate monomer to which a first carbohydrate monomer is attached. If the anomeric carbon is in the alpha position, then the glycosidic linkage is referred to as a1 or a2, where the 1 and 2 refer to carbon C-1 and carbon C-2, respectively. If the anomeric carbon is in the beta position, then only glycosidic linkages with C-1 are observed, and are referred to as b1. The carbon of the second carbohydrate monomer bearing the connecting oxygen to which a first carbohydrate monomer is attached depends upon the number of carbons present, and can be carbon C-1, C-2, C-3, C-4, C-5, C-6, C-7, or C-8, and typically is C-2, C-3, C-4, or C-6. Non-limiting examples of glycosidic linkages include those listed in Table 2.

TABLE 2

Glycosidic linkage dictionary. Linkages/branching and their codes (library B).

| S. No | Linkage | DNA Code (as in dictionary) |
|---|---|---|
| 1. | a1-1 | AAT |
| 2. | a1-2 | AAG |
| 3. | a1-3 | AAC |
| 4. | a1-4 | ATA |
| 5. | a1-5 | AGA |
| 6. | a1-6 | ACA |
| 7. | a1-7 | ATT |
| 8. | a1-8 | ATC |
| 9. | a2-1 | GTA |
| 10. | a2-2 | GTC |
| 11. | a2-3 | GGT |
| 12. | a2-4 | GGC |
| 13. | a2-5 | GGA |
| 14. | a2-6 | GTT |
| 15. | a2-7 | GAC |
| 16. | a2-8 | GAT |
| 17. | b1-1 | ATG |
| 18. | b1-2 | TCA |
| 19. | b1-3 | TCT |
| 20. | b1-4 | TGT |
| 21. | b1-5 | TCC |
| 22. | b1-6 | TTA |
| 23. | b1-7 | TTC |
| 24. | b1-8 | GAA |
| 25. | a? | GCC |
| 26. | b? | CAA |
| 27. | ?1 | CAC |
| 28. | ?2 | CTC |
| 29. | ?3 | CCA |
| 30. | ?4 | GGG |
| 31. | ?5 | CCT |
| 32. | ?6 | AGG |
| 33. | ?7 | CCG |
| 34. | ?8 | CGC |
| 35. | ?? | AGT |

TABLE 2-continued

Glycosidic linkage dictionary. Linkages/branching and their codes (library B).

| S. No | Linkage | DNA Code (as in dictionary) |
|---|---|---|
| 36. | ) | AAA |
| 37. | ( | TTT |

Question mark ("?") means i) the position or configuration of the anomeric carbon of a monomer is not characterized or (ii) the linkage position between the anomeric carbon of the monomer and the carbon bearing the connecting oxygen of the following monomer isnot characterized.

In a glycan made up of a linear chain of monomers, each monomer will be linked to two other monomers except for the first and the last monomers of the glycan. In one embodiment, a glycan includes at least one monomer that is attached by glycosidic bonds to two or more other monomers, resulting in an extension or branch of a linear chain of monomers. One or more monomers can be present in the branch, and a monomer in a branch can also serve as the beginning of another branch. Thus, a glycan described herein can be a multi-antennary structure, including, but not limited to, bi-, tri-, tetra-, and penta-antennary.

One or more carbohydrate monomers of a glycan can include one or more modifications. For example, a monomer can have a variety of compounds in place of a hydrogen (—H), hydroxy (—OH), carboxylic acid (—COOH), or methylenehydroxy (—CH$_2$—OH) substituent, or a combination thereof. Thus, a modification can be a replacement of any of the hydrogen atoms from the hydroxy (—OH), carboxylic acid (—COOH), and methylenehydroxy (—CH$_2$—OH) substituents of a monomer in a glycan described herein with a compound. Examples of compounds that can be present with a monomer are shown in Table 3. The carbon of the monomer that is modified depends upon the type of compound. For instance, most modifications can be at carbon C-2, C-4, C-7, or C-8, while a methyl and sulphate modification can also be at C-3.

TABLE 3

Modifications and their codes (library C).

| # | Compound | Modification | DNA Code (as in Dictionary) |
|---|---|---|---|
| 1. | Anhydrous | [2Y] | AGCA |
| 2. |  | [4Y] | AGCC |
| 3. |  | [7Y] | AGCG |
| 4. |  | [8Y] | AGCT |
| 5. |  | [?Y] | CCCA |
| 6. | Hydroxyl | [2OH] | AGTA |
| 7. |  | [4OH] | AGTC |
| 8. |  | [7OH] | AGTG |
| 9. |  | [8OH] | AGTT |
| 10. |  | [?OH] | CAGA |
| 11. | Pyruvate | [2V] | CAGC |
| 12. |  | [4V] | CAGG |
| 13. |  | [7V] | CAGT |
| 14. |  | [8V] | CATA |
| 15. |  | [?V] | CATC |
| 16. | Sulphate | [2S] | CATG |
| 17. |  | [4S] | CT'TT |
| 18. |  | [7S] | CGAA |
| 19. |  | [8S] | CGAC |
| 20. |  | [?S] | CGAG |
| 21. | Phosphate | [2P] | CGAT |
| 22. |  | [4P] | CGGA |
| 23. |  | [7P] | CGGC |
| 24. |  | [8P] | CGGG |
| 25. |  | [?P] | CGGT |
| 26. | n-glycolyl | [2J] | CGTA |
| 27. |  | [4J] | CGTC |
| 28. |  | [7J] | CGTG |
| 29. |  | [8J] | CGTT |
| 30. |  | [?J] | CTAA |
| 31. | n-acetyl | [2NAc] | CTAC |
| 32. |  | [4NAc] | CTAG |
| 33. |  | [7NAc] | CTAT |
| 34. |  | [8NAc] | CTGA |
| 35. |  | [?NAc] | CTGC |
| 36. | o-acetyl | [2Ac] | CTGG |
| 37. |  | [4Ac] | CTGT |
| 38. |  | [7Ac] | CTTA |
| 39. |  | [8Ac] | CTTC |
| 40. |  | [?Ac] | CTTG |
| 41. | Carboxylate | [2COOH] | CTTT |
| 42. |  | [4COOH] | GAGA |
| 43. |  | [7COOH] | GAGC |
| 44. |  | [8COOH] | GAGG |
| 45. |  | [?COOH] | GAGT |
| 46. | Inositol | [2IN] | GCAA |
| 47. |  | [4IN] | GCAC |
| 48. |  | [7IN] | GCAG |
| 49. |  | [8IN] | GCAT |
| 50. |  | [?IN] | GCGA |
| 51. | pentyl | [2EE] | GCGC |
| 52. |  | [4EE] | GCGG |
| 53. |  | [7EE] | GCGT |
| 54. |  | [8EE] | GCTA |
| 55. |  | [?EE] | GCTC |
| 56. | octyl | [2EH] | GCTG |
| 57. |  | [4EH] | GCTT |
| 58. |  | [7EH] | GTGA |
| 59. |  | [8EH] | GTGC |
| 60. |  | [?EH] | GTGG |
| 61. | deactylated-n-actyl | [2Q] | GTGT |
| 62. |  | [4Q] | TAAA |
| 63. |  | [7Q] | TAAC |
| 64. |  | [8Q] | TAAG |
| 65. |  | [?Q] | TAAT |
| 66. | N-Sulfate | [2QS] | TACA |
| 67. |  | [4QS] | TACC |
| 68. |  | [7QS] | TACG |
| 69. |  | [8QS] | TACT |
| 70. |  | [?QS] | TAGA |
| 71. | Pyruvate Acetal | [2PYR] | TAGC |
| 72. |  | [4PYR] | TAGG |
| 73. |  | [7PYR] | TAGT |
| 74. |  | [8PYR] | TATA |
| 75. |  | [?PYR] | TATC |
| 76. | N-methylcarbomoyl | [2ECO] | TATG |
| 77. |  | [4ECO] | TATT |
| 78. |  | [7ECO] | TCGA |
| 79. |  | [8ECO] | TCGC |
| 80. |  | [?ECO] | TCGG |
| 81. | Phosphocholine | [2PC] | TCGT |
| 82. |  | [4PC] | TGAA |
| 83. |  | [7PC] | TGAC |
| 84. |  | [8PC] | TGAG |
| 85. |  | [?PC] | TGAT |
| 86. | Phosphoethnlamine | [2PE] | TGCA |
| 87. |  | [4PE] | TGCC |
| 88. |  | [7PE] | TGCG |
| 89. |  | [8PE] | TGCT |
| 90. |  | [?PE] | TGGA |
| 91. | Methyl | [2ME] | TGGC |
| 92. |  | [3ME] | TGGG |
| 93. |  | [4ME] | TGGT |
| 94. |  | [7ME] | TTGA |
| 95. |  | [8ME] | TTGC |
| 96. |  | [?ME] | TTGG |
| 97. | Sulphate | [3S] | TTGT |

Question mark ("?") means the position of a modification is not characterized.

Polynucleotides

The glycan of a DNA-glycan conjugate is covalently attached to a polynucleotide. As used herein, the term "polynucleotide" refers to a polymeric form of nucleotides of any length, typically deoxynucleotides, and includes both double- and single-stranded DNA and RNA. A polynucleotide may include nucleotide sequences having different roles, including for instance one or more primer binding sites, a sequence to which one or more spacer groups are attached for use in making a multivalent DNA-glycan conjugate, or region that corresponds to (e.g., is representative of) the sequence of the glycan to which it is attached. A polynucleotide can be prepared with the aid of recombinant, enzymatic, or chemical techniques.

A polynucleotide includes a plurality of modules that, when taken together, describe the complete structure of the glycan to which the polynucleotide is attached. Thus, the nucleotide sequence of a polynucleotide is not a random string of nucleotides, instead, it is a string of nucleotides that can be translated to a glycan. Each module is a discrete nucleotide string, also referred to herein as an oligonucleotide. In one embodiment, a discrete nucleotide string is at least 2 or at least 3 consecutive nucleotides and no greater than 6, no greater than 5, or no greater than 4 nucleotides. Each module corresponds to one or more characteristics of the attached glycan.

One module is a "monomer module," and in one embodiment the polynucleotide includes one monomer module corresponding to each carbohydrate monomer present in the glycan of the DNA-glycan conjugate. Each carbohydrate monomer is associated with or described by a unique nucleotide sequence that distinguishes it from other carbohydrate monomers. Any nucleotide sequence can be used to describe a carbohydrate monomer, and one non-limiting set of examples of nucleotide sequences for individual carbohydrate monomers is shown in Table 1. For instance, using the code set out in Table 1, a monomer module having the sequence AAGC corresponds to the carbohydrate monomer N-Acetyl-Glucosamine (GlcNAc).

One module is a "linkage module," and in one embodiment the polynucleotide includes one linkage module corresponding to each glycosidic bond between each carbohydrate monomer present in the glycan of the DNA-glycan conjugate. Each linkage monomer has a unique nucleotide sequence that sets out the characteristics of the glycosidic bond including the configuration of the anomeric carbon and the number of the carbon bearing the connecting oxygen. This unique nucleotide sequence distinguishes it from other types of glycosidic bonds that could be present between two carbohydrate monomers. Any nucleotide sequence can be used to describe a glycosidic bond, and one non-limiting set of examples of nucleotide sequences for individual glycosidic bonds is shown in Table 2. For instance, using the code set out in Table 2, a linkage module having the sequence ATA corresponds to the α1-4 glycosidic linkage between two monomers. The anomeric carbon of the first monomer is carbon C-1 and in the alpha position, and carbon C-4 of the second monomer is the carbon bearing the connecting oxygen.

One module is a "modification module," and in one embodiment the polynucleotide includes one modification module corresponding to each modification that is present in the glycan of the DNA-glycan conjugate. Each modification module has a unique nucleotide sequence that sets out the characteristics of the modification, including the type of modification and the location of the modification on a carbohydrate monomer present in the DNA-glycan conjugate. In one embodiment, a modification module can also include the identity of the carbohydrate monomer that has the modification. Any nucleotide sequence can be used to describe a modification, and one non-limiting set of examples of nucleotide sequences for individual modifications and the location of the modification on a carbohydrate monomer is shown in Table 3. For instance, using the code set out in Table 3, a modification having the sequence AGTA corresponds to the modification of a hydroxyl group at carbon C-2 of a carbohydrate monomer.

As discussed herein, in one embodiment a glycan includes at least one monomer that is attached by glycosidic bonds to at least two other monomers to form a branch in a linear sequence of monomers. The modules that describe the one or more monomers present in the branch are a "branch beginning module" and a "branch ending module." A branch beginning module and a branch ending module each have a unique nucleotide sequence that sets out which monomer(s) is present in the branch. In one embodiment, the identity of a monomer in a branch (i.e., a monomer module), the glycosidic bond between the monomer of the branch and the monomer that is part of the linear chain (i.e., a linkage module), and any modifications to the monomer in the branch (i.e., a modification module) are described between a branch beginning module and a branch ending module. Any nucleotide sequence can be used to describe a branch beginning module and a branch ending module, and one non-limiting set of examples of nucleotide sequences for a branch beginning module and a branch ending module are shown at lines 36 and 37 of Table 2. For instance, using the code set out in Table 2, the beginning of a branch is shown by the sequence AAA and the end of a branch is shown by the sequence TTT.

One module is a "core module." A core module describes a specific glycan structure that is observed as part of more than one glycan. The specific glycan structure is 2, 3, 4, or more monomers having specific glycosidic bonds between the monomers. Each core module has a specific nucleotide sequence that sets out the specific glycan structure, including the identity of each monomer, the order of the monomers, and the glycosidic bonds between the monomers. Any nucleotide sequence can be used to describe a specific glycan structure, and one non-limiting set of examples of specific glycan structures and nucleotide sequences for each structure is shown in Table 4. For instance, using the code set out in Table 4, the specific glycan structure Man b1-4 GlcNAc b1-4(Fuc a1-6) GlcNAc has the sequence GTACA. The use of a core module in a polynucleotide is optional because the other modules described herein can be used to describe the specific glycan structure; however, in some embodiments the use of a core module instead of the other modules can be helpful in reducing the total number of nucleotides present in the polynucleotide.

TABLE 4

Core structures and their codes (library D).

| S. No | Sugar blocks for Secondary naming | CFG 2D structure | Long Nucleotide | Length | Assigned short DNA code |
|---|---|---|---|---|---|
| 1. | Man b1-4 GlcNAc b1-4(Fuc a1-6) GlcNAc | | AATATGTAAGCTGTTTTAGAAACAAAAAGC (SEQ ID NO: 2) | 31 | GTACA |
| 2. | Man a1-6Man b1-4 GlcNAc b1-4 GlcNAc | | AATAACAAATATGTAAGCTGTAAGC (SEQ ID NO: 3) | 25 | GTACT |
| 3. | Gal b1-4 GlcNAc b1-4 | | ACGATGTAAGCTGT (SEQ ID NO: 4) | 14 | GTCCT |
| 4. | Gal a1-3 Gal b1-4 GlcNAc b1-2 | | ACGAAACACGATGTAAGCTCA (SEQ ID NO: 5) | 21 | GTACC |
| 5. | Gal a1-3 Gal b1-4 GlcNAc b1-3 | | ACGAAACACGATGTAAGCTCT (SEQ ID NO: 6) | 21 | GTTAT |
| 6. | Gal b1-3 GlcNAc b1-4 | | ACGATCTAAGCTGT (SEQ ID NO: 7) | 14 | GTTCA |
| 7. | Man a1-3 Man a1-6 | | AATAAACAATAACA (SEQ ID NO: 8) | 14 | GTTTG |
| 8. | GalNAc b1-4 GlcNAc b1-2 | | ACGCTGTAAGCTCA (SEQ ID NO: 9) | 14 | GTTTC |
| 9. | Fuc a1-3 GlcNAc b1-2 | | AGAAAACAAGCTCA (SEQ ID NO: 10) | 14 | GTTGT |
| 10. | Fuc a1-2 Gal b1-4(Fuc a1-3) GlcNAc b1-2 | | AGAAAAGACGATGTTTTAGAAAACAAAAGCTCA (SEQ ID NO: 11) | 34 | GGATT |
| 11. | Fuc a1-2 Gal b1-4 GlcNAc b1-2 | | AGAAAAGACGATGTAAGCTCA (SEQ ID NO: 12) | 21 | GTTGC |
| 12. | Gal b1-4(Fuc a1-3) GlcNAc b1-4 | | ACGATGTTTTAGAAAACAAAAAGCTGT (SEQ ID NO: 13) | 27 | GTGAG |
| 13. | GalNAc b1-4 GlcNAc b1-6 | | ACGCTGTAAGCTTA (SEQ ID NO: 14) | 14 | GTGTC |
| 14. | Gal b1-4 GlcNAc b1-6 | | ACGATGTAAGCTTA (SEQ ID NO: 15) | 14 | GTGCG |

TABLE 4-continued

Core structures and their codes (library D).

| S. No | Sugar blocks for Secondary naming | CFG 2D structure | Long Nucleotide | Length | Assigned short DNA code |
|---|---|---|---|---|---|
| 15. | NeuAc a2-3 Gal b1-4 GlcNAc b1-4 | | AGGCGGTACGATGTAAGCTGT (SEQ ID NO: 16) | 21 | GTGGA |
| 16. | NeuAc a2-3 Gal b1-4 GlcNAc b1-6 | | AGGCGGTACGATGTAAGCTTA (SEQ ID NO: 17) | 21 | GTGGT |

The length of a polynucleotide attached to a glycan is not intended to be limiting. In one embodiment, a polynucleotide is a length that is useful for amplification by a PCR-based method. Polynucleotide lengths that are useful for amplification include, but are not limited to, at least 20, at least 40, or at least 50 to no greater than 200, no greater than 300, or no greater than 400. A core module can be used to describe a specific glycan structure when use of the other modules results in a polynucleotide that is longer than desired. In one embodiment, a polynucleotide includes an "extension module." An extension module is a nucleotide sequence that can be added to a polynucleotide when the glycan sequence described by the polynucleotide is shorter than desired. Any nucleotide sequence can be used as an extension module, and one non-limiting example is CCCCAGTCAGGCCTAACGTA (SEQ ID NO:1) as shown at line 74 of Table 1.

In one embodiment, a polynucleotide also includes additional nucleotide sequences that can be used as primer binding sites for use in, for instance, amplification and/or sequencing.

The skilled person will recognize that any order of modules in the polynucleotide is possible. In one embodiment, the order of the nucleotides can follow the naming convention set forth by the IUPAC for the linear description for glycans.

Covalent Attachment

A spacer group, also referred to as a linker, attaches the glycan and the polynucleotide of a DNA-glycan conjugate. A spacer group includes a stable (e.g., substantially chemically inert) molecule. In one embodiment, a spacer group can be an alkylene or an alkenylene. The term "alkylene" refers to a saturated linear or hydrocarbon group —$(CH_2)n$-, where n is an integer from 1 to 20. The term "alkenylene" refers to an unsaturated, linear hydrocarbon group —$(CH_m)n$-, where n is an integer from 1 to 20 and m is 1 or 2, with one or more carbon-carbon double bonds. In another embodiment, a spacer group can be an amino acid sequence. A protein spacer group can be at least 3, at least 4, at least 5, or at least 6 amino acids in length. A spacer group can be attached to the glycan either as an alpha or beta linkage of one of the carbohydrate monomers, or attached to another carbon of one of the carbohydrate monomers. In one embodiment, a spacer group is attached to the reducing end of the glycan. A spacer group can be attached to the polynucleotide at either the 5' or the 3' end. Generally, the spacer group is one that does not interfere with either the binding of a DNA-glycan conjugate to a glycan-binding compound or the amplification of the attached polynucleotide.

Referring now to FIG. 1, a schematic drawing is shown of one embodiment of a DNA-glycan conjugate 10 that can be used with various embodiments described herein. The depicted DNA-glycan conjugate 10 includes a glycan 12, a spacer group 14, and a polynucleotide 16.

Figure 2:
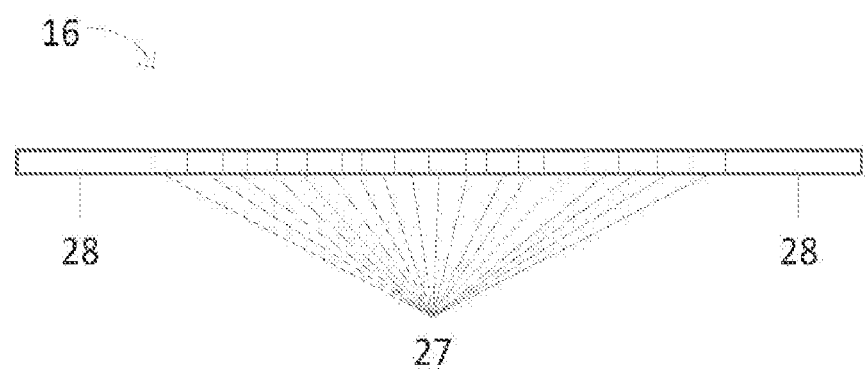
FIG. 2 is a schematic drawing of one embodiment of a polynucleotide of a DNA-glycan conjugate according to the present disclosure.

Referring now to FIG. 2, a schematic drawing of one embodiment of a polynucleotide 16 of a DNA-glycan conjugate 10 that can be used with various embodiments described herein. The depicted polynucleotide 16 includes multiple modules 27, and also includes optional primers 28.

Also provided are compositions. In one embodiment, a composition includes a DNA-glycan conjugate, e.g., a population of a DNA-glycan conjugate where each DNA-glycan conjugate is the same. In one embodiment, a composition includes more than one DNA-glycan conjugate, e.g., it is a collection of two or more populations of DNA-glycan conjugates where each DNA-glycan conjugate is different. A composition having more than one DNA-glycan conjugate is also referred to as a library. In one embodiment, each polynucleotide of the DNA-glycan conjugates of a library include a first primer and a second primer. The primers can be situated to allow amplification of the nucleotides that identify the structure of the attached glycan. In one embodiment, the nucleotide sequence of a first primer is the same on each DNA-glycan conjugate, and the nucleotide sequence of a second primer is the same on each DNA-glycan conjugate. In another embodiment, the nucleotide sequence of first and second primers are unique to each DNA-glycan of the library, permitting detection of the presence or absence of a specific DNA-glycan conjugate.

In one embodiment, a composition includes a DNA-glycan conjugate specifically bound to a glycan-binding compound.

Methods of Making

Methods for producing glycans and polynucleotides are known to the skilled person and are routine. For instance, methods that can be used to produce glycans are described by Li et al. (2015, Chem Sci 6(10): 5652-5661), Xiao et al. (2016, J Org Chem 81(14): 5851-5865), and Su et al. (2008, Org Lett 10(5): 1009-1012). Synthetic glycans and reagents for in vitro synthesis of glycans are commercially available. Methods for producing polynucleotides having a specific sequence include in vitro synthesis such as chemical synthesis with a conventional DNA synthesizer. Synthetic polynucleotides and reagents for in vitro synthesis are commercially available.

Methods for attaching a glycan and a polynucleotide are also known to the skilled person and are routine. The method by which a glycan and polynucleotide are attached is not intended to be limiting. In one embodiment, tagging or click chemistry methods can be used to attach the two components of a DNA-glycan conjugate. Many click chemistry methods are known, and non-limiting examples include, but are not limited to, copper(I)-catalyzed azide-alkyne cycloaddition (CuAAC) reactions, strain-promoted azide-alkyne cycloaddition (SPAAC) reactions, and strain-promoted alkyne-nitrone cycloaddition (SPANC). In general, a glycan can be modified to include one reactive group and the polynucleotide modified to include the other reactive group. For instance, when CuAAC chemistry is used, one component of a DNA-glycan conjugate includes an azido group, and the other component includes an alkyne group. Methods for modifying a glycan and a polynucleotide to include a reactive group, such as an azido group or an alkyne group are known and routine. In one embodiment, the polynucleotide can be modified to include multiple reactive groups to produce a multivalent DNA-glycan conjugate (Example 2).

Methods of Use

Provided herein are methods for using DNA-glycan conjugates. In one embodiment, a method determines whether a DNA-glycan conjugate and a glycan-binding compound interact to form a complex. Thus, methods described herein include, but at not limited to, determining whether a single DNA-glycan conjugate can bind a single glycan-binding compound, whether a DNA-glycan conjugate can identify a glycan-binding compound in a sample that includes multiple glycan-binding compounds, whether a composition of multiple DNA-glycan conjugates can identify individual glycan-binding compounds in a sample that includes multiple glycan-binding compounds, and whether a composition of multiple DNA-glycan conjugates can identify an individual glycan-binding compound in a sample that one glycan-binding compound.

As used herein, the term "glycan-binding compound" refers to a compound that specifically binds a glycan. A glycan-binding compound that can specifically bind a glycan is one that interacts only with a specific structure present on a glycan. A glycan-binding compound that specifically binds a glycan will, under the appropriate conditions, interact with the glycan even in the presence of a diversity of potential binding targets. For instance, if the glycan-binding compound is an antibody, an antibody that can specifically bind a glycan is one that interacts only with the glycan that induced the synthesis of the antibody, or interacts with a structurally related epitope. An antibody that specifically binds to an epitope will, under the appropriate conditions, interact with the epitope even in the presence of a diversity of potential binding targets. In one embodiment, a glycan-binding compound can bind more than one DNA-glycan conjugate. For instance, a glycan-binding compound can include different structures, each of which can bind a different DNA-glycan conjugate. Likewise, in one embodiment, a DNA-glycan conjugate can bind more than one glycan-binding compound.

The make-up of a glycan-binding compound is not intended to be limiting, and includes, for instance, a protein. Examples of a protein glycan-binding compound includes, but is not limited to, an antibody (including a polyclonal and a monoclonal antibody), a phytohemagglutinin, and a protein encoded by a microbe (e.g., encoded by a virus, a prokaryotic microbe, or a eukaryotic microbe). A glycan-binding compound is often referred to in the art as a lectin. A glycan-binding compound can be from any source, such as from an animal (including a human) or a plant. A glycan-binding compound can be natural or non-natural (e.g., it is not known to exist in nature). Examples of glycan-binding compounds are commercially available. For instance, phytohemagglutinins such as concanavalin A, wheat germ agglutinin, and ricin are commercially available. Antibody to some glycans are also commercially available.

In one embodiment, a glycan-binding compound is present in a sample, such as a biological sample. As used herein, the term "biological sample" refers to a sample of tissue or fluid isolated from a subject. In one embodiment, the subject is an animal, such as a human. A biological sample from an animal includes, but is not limited to, for example, blood, plasma, serum, urine, bone marrow, bile, spinal fluid, lymph tissue and lymph fluid, fecal matter, samples of the skin, external secretions of the skin, respiratory, intestinal, and genitourinary tracts, tears, saliva, milk, blood cells, organs, biopsies (including biopsy of diseased tissue, such as a tumor) and also samples of in vitro cell culture constituents including but not limited to conditioned media resulting from the growth of cells and tissues in culture medium, e.g., recombinant cells, and cell components. In one embodiment, the subject is a plant.

A method can include a mixture such as a single DNA-glycan conjugate and a single glycan-binding compound, a complex mixture such as a plurality of DNA-glycan conjugates and a plurality of glycan-binding compounds, and variations thereof. Variations include, but are not limited to, a single DNA-glycan conjugate combined with a plurality of glycan-binding compounds, and a plurality of DNA-glycan conjugates combined with a single glycan-binding compound. A plurality of DNA-glycan conjugates includes at least 2, at least 5, at least 10, or at least 20 different DNA-glycan conjugates. It is expected that there is no upper limit of the number of different DNA-glycan conjugates that can be present in a plurality of different DNA-glycan conjugates; however, in one embodiment, a plurality of different DNA-glycan conjugates includes no greater than 100, no greater than 1000, or no greater than 10,000. A plurality of glycan-binding compounds includes at least 2, at least 5, at least 10, or at least 20 different glycan-binding conjugates. It is expected that there is no upper limit of the number of different glycan-binding compounds that can be present in a plurality of different glycan-binding compounds; however, in one embodiment, a plurality of different DNA-glycan conjugates includes no greater than 100, no greater than 1000, or no greater than 10,000. In some embodiments, such as when a biological sample is used, it is expected that the number of glycan-binding compounds will be unknown.

In one embodiment, a method includes identifying a glycan-binding compound, e.g., identifying whether a glycan-binding compound is present or undetectable, e.g., absent. The method can include contacting one or more DNA-glycan conjugates with a sample, such as a biological sample, to result in a mixture. The sample can be one that is suspected of including a glycan-binding compound, or known to include a glycan-binding compound. In one embodiment, the DNA-glycan conjugate is in solution, and in another embodiment the DNA-glycan conjugate is bound to a surface. In one embodiment, a glycan-binding compound is in solution, and in another embodiment a glycan-binding compound is bound to a surface. For instance, a glycan-binding compound can be bound to an artificial surface such as a well of a multi-well plate. In one embodiment, when a glycan-binding compound is in solution it can be tagged with a detectable marker, such as a fluorescent marker. In one embodiment, the sample is suspected of including a glycan-binding compound that will bind the DNA-glycan conjugate. In another embodiment that can be useful as a control, the DNA-glycan conjugate used is one that is expected to not bind a glycan-binding compound present in the sample. The contacting is under conditions suitable for binding of the glycan-binding compound and the DNA-glycan conjugate to from a complex. Conditions suitable for binding of a glycan-binding compound and a DNA-glycan conjugate are typically physiological conditions, e.g., pH of 7 to 7.8, such as 7.4. The temperature can vary from 4° C. to 40° C., such as 37° C.

In one embodiment, the sample can include more than one glycan-binding compound. For instance, Example 1 includes contacting a DNA-glycan conjugate with a sample that includes three antibodies that are glycan-binding compounds (antibody to blood group A, antibody to blood group B, and antibody to blood group O, see FIG. 14C of Example 1). In another embodiment, the sample can include a plurality of glycan-binding compounds, and the sample is contacted with a plurality of DNA-glycan conjugates.

In one embodiment, a method can include reducing in a mixture the amounts of DNA-glycan conjugates that are not bound to a glycan-binding compound. The reducing can be to a level where unbound DNA-glycan conjugates are not detectable. Removal of unbound DNA-glycan conjugates can be accomplished using routine methods, such as filtration. Filtration methods can include the use of a filter with a molecular weight cut-off that retains a complex but allows unbound DNA-glycan conjugates and unbound glycan-binding compounds to pass through. Examples of useful molecular weight cut-offs includes greater than 50 kiloDaltons (kDa) such as 100 kDa. In another embodiment, immunoprecipitation methods can be used when the glycan-binding compound is an antibody. Immunoprecipitation methods are routine and include, for instance, antibody-binding reagents such as protein A, protein G, and the like, to reduce the amounts of unbound DNA-glycan conjugates.

A method also includes identifying a DNA-glycan conjugate bound to a glycan-binding compound. In one embodiment, the identification of a bound DNA-glycan conjugate includes amplification of the polynucleotide attached to the DNA-glycan conjugate. Amplification typically includes a method based on the polymerase chain reaction (PCR). In one embodiment, the amplification is by quantitative PCR (qPCR), also referred to as real-time PCR (rtPCR). qPCR allows amplification of a nucleotide sequence in such a way that the relative amount of a template polynucleotide in a mixture before amplification can be determined and compared to other template polynucleotides present in the mixture before amplification. In one embodiment, routine methods are used to obtain a critical threshold (Ct) value, which can be used to compare the concentration of different template polynucleotides. For instance, Example 1 describes an evaluation of the specificity of a DNA-glycan conjugate for three different antibodies. The DNA-glycan conjugate was the human blood group B antigen, which was identified by anti-human blood group B antibody. Three separate mixtures were made (the DNA-glycan conjugate having the human blood group B antigen and a glycan-binding compound that was either anti-human blood group A antibody, anti-human blood group B antibody, or anti-human blood group O antibody), incubated under conditions suitable for binding to occur, and then the nucleotide sequence of the polynucleotide attached to the bound DNA-glycan conjugate of each separate mixture was amplified using qPCR. Comparison of the Ct values show that the DNA-glycan conjugate specifically bound to anti-human blood group B antibody as expected and did not specifically bind anti-human blood group A antibody or anti-human blood group O antibody (see FIG. 14D).

In another embodiment, the identification of a bound DNA-glycan conjugate includes determining the nucleotide sequence of the polynucleotide attached to the DNA-glycan conjugate. While any nucleotide sequencing method can be used, high-throughput methods are useful with embodiments where a mixture is expected to include multiple DNA-glycan conjugates bound to glycan-binding compounds. Methods for high throughput sequencing, also known as next generation sequencing, are known in the art and are routine. Multiplex sequencing is also possible. Examples include, but are not limited to, sequencing by synthesis, single-molecule real-time sequencing, and pyrosequencing.

In one embodiment, a method provided herein can be used to determine whether a specific glycan is present in a subject.

In one embodiment, the glycan can be one associated with a blood group. Accordingly, in one embodiment a method provided herein can be used to determine the blood type of an individual. The glycan structure of blood group antigens, for instance, A, B, and O, as well as other rarer blood group antigens, are known. DNA-glycan conjugates having a glycan that has the structure of the A, B, O, or other groups, can be used in a method described herein to determine the blood group of an individual by identifying the presence of a glycan-binding compound, such as an antibody, in a biological sample from the individual. The glycan structure of other rarer blood group antigens, for instance, P, p1, Pk, FORS1, LKE, I, and i, are also known and can be determined using methods described herein.

In another embodiment, the glycan can be one associated with a pathological condition. Expression of glycans is widely altered in many pathological conditions including cancer (including, but not limited to, epithelial cancer, ovarian cancer, fallopian tube cancer, peritoneal cancer, breast cancer, colon cancer, pancreatic cancer, brain cancer, prostate cancer, skin cancer, lung cancer, and blood cancer), retrovirus infection, atherosclerosis, thrombosis, diabetes, neurodegeneration, arthritis and other diseases (Fernandez-Tejada et al., 2015, Chemistry, 21(30):10616-28), and typically an individual will produce anti-glycan antibody that binds to new glycans associated with a pathological condition. For instance, members of the globo series glycans are overexpressed in certain cancers and are known to be biomarkers for the early detection of breast cancer and ovarian cancer (Huang et al., 2006, PNAS USA, 103(1):15-20; Pochechueva et al., 2017, J. Ovarian Res., 10(1):8; Cheng et al., 2016, J. Surgical Oncology, 114(7):853-858; and Wang et al., 2008, PNAS USA, 105(33):11661-6). Recent developments in Globo-H based immunotherapy is aided by methods to quantitatively detect the anti-Globo-H antibodies for monitoring the therapy and in clinical trials (Danishefsky et al., 2015, Accounts of Chemical Research, 48(3):643-652; Zhou et al., 2015, Chemical Science, 6(12): 7112-7121; O'Cearbhaill et al., 2016, Cancers, 8(4)). Changes in glycans in cancers is also disclosed by Dube and Bertozzi (Nature reviews. Drug discovery 4.6 (2005): 477), and Pinho and Reis (Nature reviews. Cancer 15.9 (2015): 540). Malignant tissue can be characterized by a distinct set of changes in glycan expression (Dube and Bertozzi, Nature reviews. Drug discovery 4.6: 477, 2005; Zhang et al., Int. J. Cancer, 73:42-49, 1997; and Zhang et al., Int. J. Cancer, 73:50-56, 1997). The glycan $sLe^x$ is associated with pancreas, breast, colon, and lung cancers; the glycan sLea is associated with pancreas, breast, colon, and lung cancers; the glycan sTn is associated with ovary, pancreas, breast, colon, prostate, and lung cancers; the glycan TF is associated with ovary, breast, colon, prostate, and lung cancers; the glycan $Le^y$ is associated with ovary, pancreas, breast, colon, prostate, and lung cancers; the glycan Globo H is associated with ovary, pancreas, breast, colon, prostate, and lung cancers; the glycan PSA is associated with pancreas, blood, breast, brain, and lung cancers; the glycan GD2 is associated with blood, brain, and skin cancers; the glycan GD3 is associated with brain and skin cancers; the glycan Fucosyl GM1 is associated with lung cancers; and the glycan GM2 is associated with ovary, pancreas, blood, breast, colon, brain, prostate, skin, and lung cancers.

Kits

Also provided herein is a kit. In one embodiment, a kit is for identifying a DNA-glycan conjugate bound to a glycan-binding compound. In another embodiment, a kit is for identifying a plurality of DNA-glycan conjugates bound to glycan-binding compounds. For instance, a kit can be for determining the blood group of a subject. In another embodiment, a kit can be for determining if a subject expresses glycan-binding compounds associated with a pathological condition.

A kit includes at least one DNA-glycan conjugate described herein (e.g., one, at least two, at least three, etc.). In one embodiment, a kit includes primers that can be used to amplify a polynucleotide attached to the one or more DNA-glycan conjugates. Optionally, other reagents such as buffers and solutions needed to use the components of the kit are also included. The components of a kit, for instance, each DNA-glycan conjugate and optional primers, can be in separate containers. Instructions for use of the packaged components are also typically included. As used herein, the phrase "packaging material" refers to one or more physical structures used to house the contents of the kit. The packaging material is constructed by routine methods, generally to provide a sterile, contaminant-free environment. The packaging material may have a label which indicates that the components can be used for identifying a DNA-glycan conjugate bound to a glycan-binding compound. In addition, the packaging material contains instructions indicating how the components within the kit are employed. As used herein, the term "package" refers to a container such as glass, plastic, paper, foil, and the like, capable of holding within fixed limits the proteins, and other reagents, for instance a DNA-glycan conjugate. "Instructions for use" typically include a tangible expression describing the components or at least one assay method parameter, such as the relative amounts of DNA-glycan conjugate and sample to be admixed, maintenance time periods for reagent/sample admixtures, temperature, buffer conditions, and the like.

Algorithm

Also provided is an algorithm. In one embodiment, an algorithm converts a glycan structure into a nucleotide sequence that is representative of the glycan structure. The glycan structure includes a description of individual components of a glycan including the carbohydrate monomers, how they are linked, any modifications that are present, and any branches that are present. The nucleotide sequence is present in the polynucleotide described herein. The nucleotide sequence includes a plurality of modules that, when taken together, describe the glycan structure.

In another embodiment, an algorithm translates a nucleotide sequence of a polynucleotide, such as a polynucleotide attached to a glycan (e.g., part of a DNA-glycan conjugate), into a glycan structure.

Figure 3:
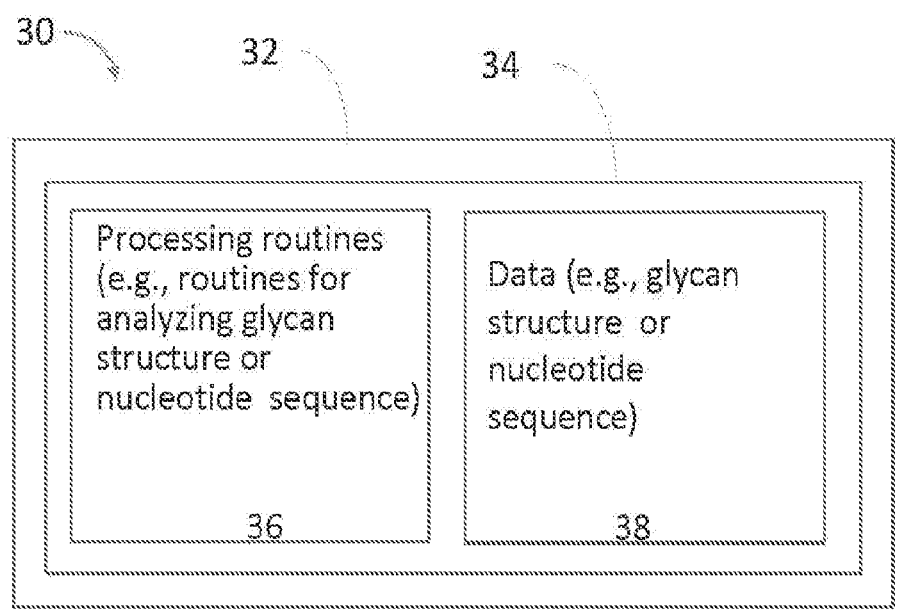
FIG. 3 shows a general block diagram of a general illustrative data processing system for use in the analysis of data according to the present disclosure.

FIG. 3 shows a system 30 including processing apparatus (block 32) and data storage (block 34). Data storage (block 34) allows for access to processing programs or routines (block 36) and one or more other types of data (block 38) that may be employed to carry out the illustrative methods (e.g., two of which are shown generally in the block diagram of, for instance, FIGS. 4 and 7).

For example, processing programs or routines (block 36) may include programs or routines for performing standardization algorithms, logic algorithms, or any other processing required to implement one or more embodiments as described herein. Data (block 38) may include, for example, glycan structure, nucleotide sequence, etc., results from one or more processing programs or routines employed according to the present disclosure, or any other data that may be necessary for carrying out the one or more processes described herein.

In one or more embodiments, the system 30 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and to generate desired output information. The output information may be applied as input to one or more other devices and/or processes as described herein or as would be applied in a known fashion.

The program used to implement the processes described herein may be provided using any programmable language, e.g., a high level procedural and/or object orientated programming language that is suitable for communicating with a computer system. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the system 30 may be implemented using a non-transitory computer readable storage medium, configured with a computer program, where the non-transitory storage medium so configured causes the computer to operate in a specific and predefined manner to perform functions described herein.

Likewise, the system 30 may be configured at a remote site (e.g., an application server) that allows access by one or more users via a remote computer apparatus (e.g., via a web browser), and allows a user to employ the functionality according to the present disclosure (e.g., user accesses a graphical user interface associated with one or more programs to process data).

The processing apparatus (block 32), may be, for example, any fixed or mobile computer system (e.g., a personal computer or mini-computer). The exact configuration of the computing apparatus is not limiting and essentially any device capable of providing suitable computing capabilities and control capabilities may be used. Further, various peripheral devices, such as a computer display, mouse, keyboard, memory, printer, scanner, are contemplated to be used in combination with processing apparatus (block 32) of the data storage (block 34).

Figure 4:
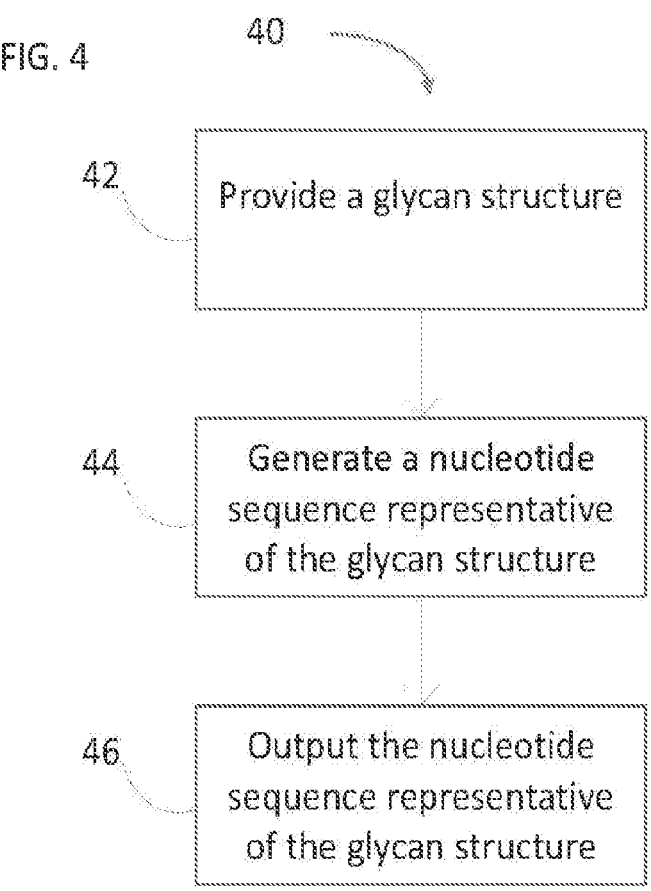
FIG. 4 shows a general block diagram of a general illustrative data processing method for analyzing a glycan structure according to the present disclosure.

FIG. 4 shows a general block diagram of an illustrative method 40 for use in analysis of data, such as data related to glycan structure. One will recognize that one or more of the blocks of functionality described herein may be carried out using one or more programs or routines, and/or any other components of an exemplary system.

Generally, the exemplary method 40 includes providing a glycan structure 42, generating a nucleotide sequence based on the glycan structure 44, and outputting the nucleotide sequence based on the glycan structure 46. The glycan structure can be any kind of data that may be effectively analyzed using the exemplary methods and programs described herein. The glycan structure can be a linear description of a glycan, including, but not limited to, a linear description in the IUPAC format, or a description in the symbol nomenclature of the CFG format.

Figure 5:
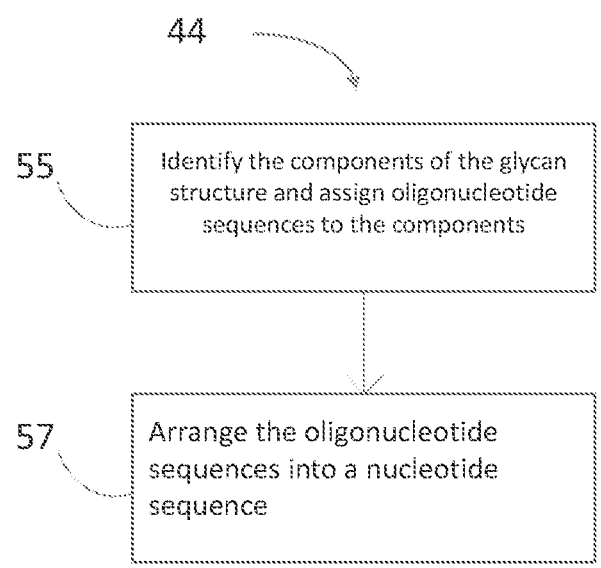
FIG. 5 shows a more detailed block diagram of one illustrative embodiment of a method for analyzing a glycan structure as generally illustrated in the method of FIG. 4.

FIG. 5 shows a general block diagram of an illustrative method for use in generating a nucleotide sequence based on the glycan structure 44. The generating can include identifying the components of the glycan structure and assigning an oligonucleotide sequence to each component 55, and arranging the oligonucleotides, also referred to as modules, into a nucleotide sequence 57. Generally, the nucleotide sequence of each oligonucleotide is obtained by reference to one or more datasets. A dataset can include information identifying different components of a glycan structure, such as carbohydrate monomers, glycosidic linkages, and modifications, and link a unique oligonucleotide identifier to each component. In one embodiment, the method includes providing one or more datasets to generate the nucleotide sequence based on the glycan structure, wherein generating the nucleotide sequence based on the glycan structure includes generating the nucleotide sequence based on the glycan structure and the one or more datasets.

Figure 6:
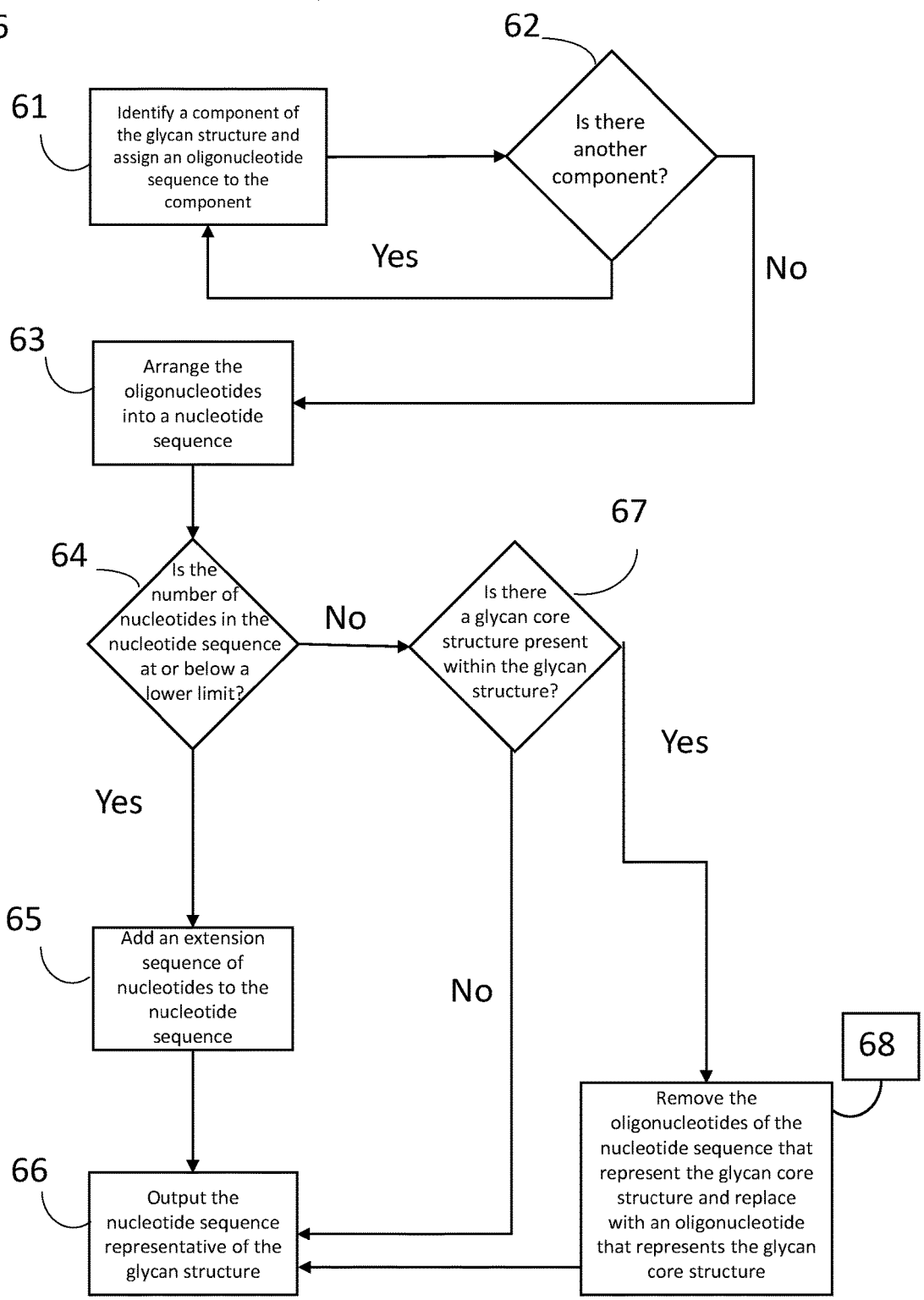
FIG. 6 shows a more detailed block diagram of one illustrative embodiment of a method for analyzing a glycan structure as generally illustrated in the method of FIG. 4.

FIG. 6 shows a general block diagram of one embodiment of generating a nucleotide sequence based on the glycan structure 44. The generating can include identifying one component of the glycan structure and assigning an oligonucleotide sequence to the component 61, where the identifying continues 62 until each component is identified and assigned an oligonucleotide sequence. Generally, the nucleotide sequence of each oligonucleotide is obtained by reference to a dataset. A dataset can include information identifying different components of a glycan structure, such as carbohydrate monomers, glycosidic linkages, and modifications, and assigning a unique oligonucleotide identifier for each component. The oligonucleotides are arranged into a nucleotide sequence 63. The arranging can occur after each component is identified, or can occur during the iterative process of 61 and 62 is completed. The number of nucleotides in the nucleotide sequence is determined 64. If the number of nucleotides is at or below a lower limit, such as 20 nucleotides, an extension sequence of nucleotides is added to the nucleotide sequence 65, and the nucleotide sequence based on the glycan structure is produced 66. If the number of nucleotides in the nucleotide sequence is greater than the lower limit 64, the presence of a glycan core structure in the glycan structure is determined 67. If there is a glycan core structure in the glycan structure, then the oligonucleotides of the nucleotide sequence that represent the glycan core structure are removed from the nucleotide sequence and replaced with an oligonucleotide that represents the glycan core structure 68, and the nucleotide sequence based on the glycan structure is produced 66. If there is not a glycan core structure in the glycan structure, then the nucleotide sequence based on the glycan structure is produced 66.

Figure 7:
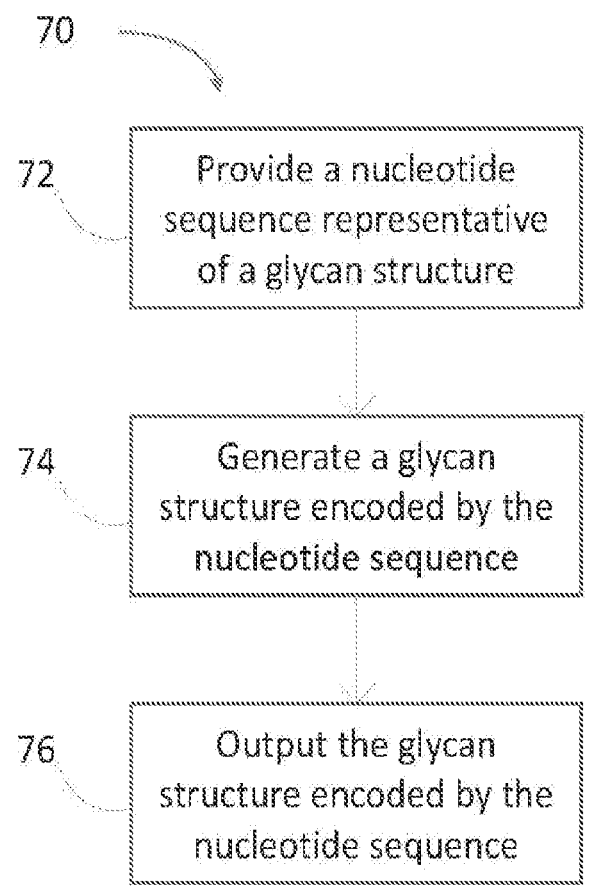
FIG. 7 shows a general block diagram of a general illustrative data processing method for analyzing a nucleotide sequence according to the present disclosure.

FIG. 7 shows a general block diagram of an illustrative method 70 for use in analysis of data, such as data related to nucleotide sequence. One will recognize that one or more of the blocks of functionality described herein may be carried out using one or more programs or routines, and/or any other components of an exemplary system.

Generally, the exemplary method 70 includes providing a nucleotide sequence representative of a glycan structure 72, generating a glycan structure based on the nucleotide sequence 74, and outputting the glycan structure based on the nucleotide sequence 76. The nucleotide sequence can be any kind of data that may be effectively analyzed using the exemplary methods and programs described herein. The outputted glycan structure can be a linear description of a glycan, including, but not limited to, a linear description in the IUPAC format or a description in the symbol nomenclature of the CFG format.

Figure 8:
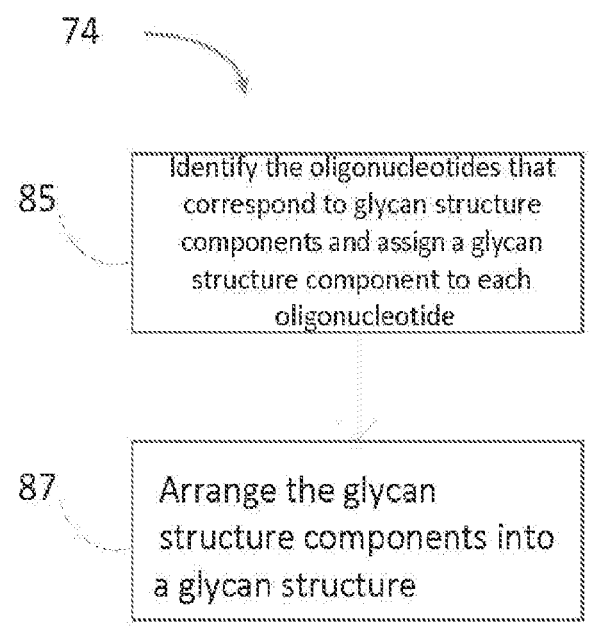
FIG. 8 shows a more detailed block diagram of one illustrative embodiment of a method for analyzing a nucleotide sequence as generally illustrated in the method of FIG. 7.

FIG. 8 shows a general block diagram of generating a glycan structure based on the nucleotide sequence 74. The generating can include identifying the oligonucleotides in the nucleotide sequence that correspond to the components of the glycan structure and assigning a glycan structure component to each oligonucleotide 85, and arranging the glycan structure components into a glycan structure 87. Generally, the glycan structure component encoded by each oligonucleotide is obtained by reference to one or more datasets. A dataset can include information identifying different components of a glycan structure, such as carbohydrate monomers, glycosidic linkages, and modifications, and link a unique oligonucleotide identifier to each component. In one embodiment, the method includes providing one or more datasets to generate the glycan structure based on the nucleotide sequence, wherein generating the glycan structure based on the nucleotide sequence includes generating the glycan structure based on the nucleotide sequence and the one or more datasets.

Figure 9:
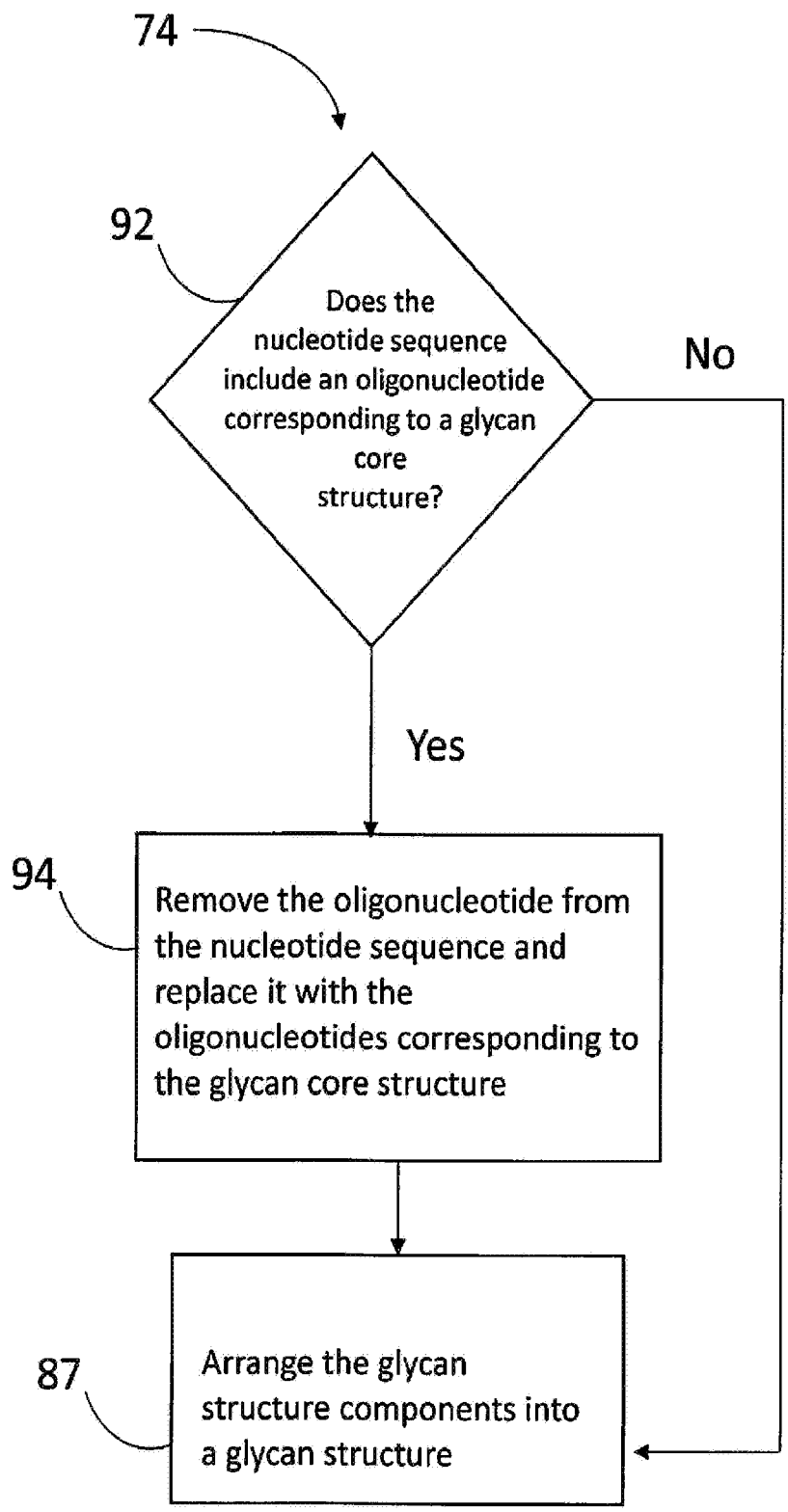
FIG. 9 shows a more detailed block diagram of one illustrative embodiment of a method for analyzing a nucleotide sequence as generally illustrated in the method of FIG. 7.

FIG. 9 shows a general block diagram of an embodiment for generating a glycan structure based on the nucleotide sequence 74. The generating can include determining whether a nucleotide sequence includes an oligonucleotide corresponding to a glycan core structure 92. If the nucleotide sequence includes an oligonucleotide corresponding to a glycan core structure, then the oligonucleotide is removed from the nucleotide sequence and replaced with the oligonucleotides that correspond to the glycan core structure 94. The glycan structure components are arranged into a glycan structure 87.

Figure 10:
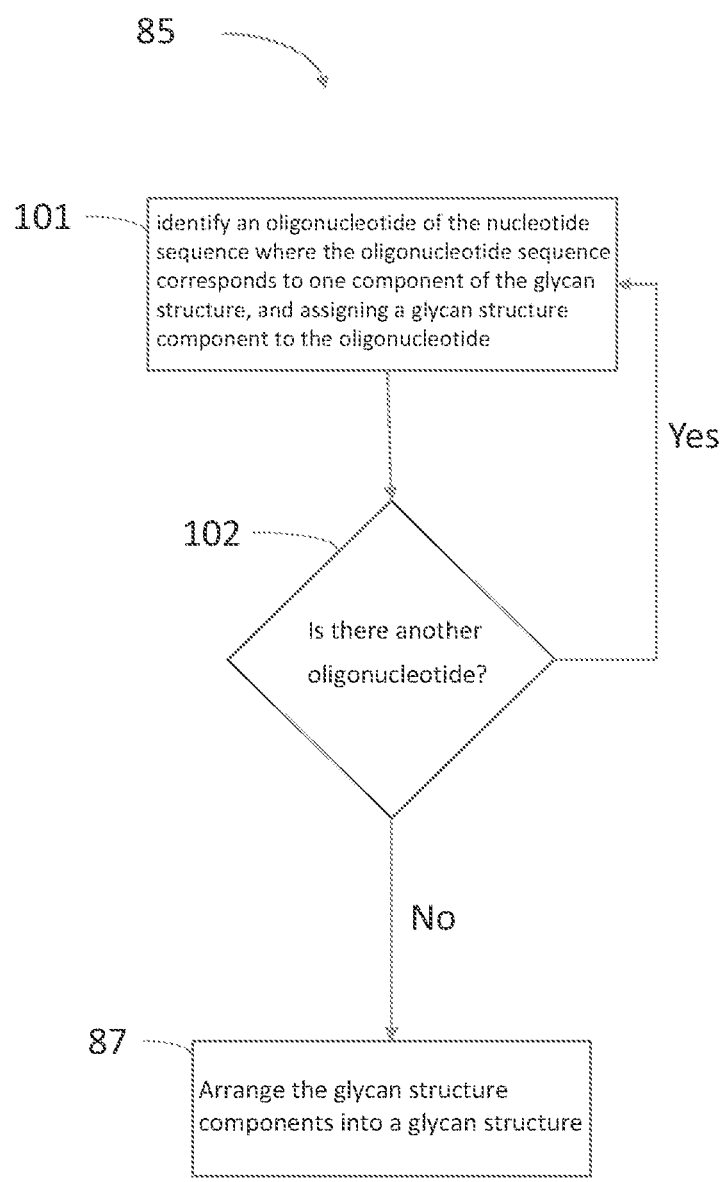
FIG. 10 shows a more detailed block diagram of one illustrative embodiment of a method for analyzing a nucleotide sequence as generally illustrated in the method of FIG. 8.

FIG. 10 shows a general block diagram of one embodiment of identifying the oligonucleotides within a nucleotide sequence that is based on a glycan structure 85. The identifying can include identifying one oligonucleotide of the nucleotide sequence where the oligonucleotide sequence corresponds to one component of the glycan structure, and assigning a glycan structure component to the oligonucleotide 101, where the identifying continues 102 until each component is identified. Generally, the glycan structure component that corresponds to an oligonucleotide is obtained by reference to a dataset. A dataset can include information identifying different components of a glycan structure, such as carbohydrate monomers, glycosidic linkages, and modifications, and linking a component to a unique oligonucleotide identifier. The glycan structure components are arranged into a glycan structure 87. The arranging can occur after each oligonucleotide is identified and assigned a glycan structure component, or can occur during the iterative process of 101 and 102 is completed.

After generating a nucleotide sequence based on the glycan structure 44, the method can further include outputting the nucleotide sequence based on the glycan structure 46. Further, after generating a glycan structure based on a nucleotide structure 74, the method can further include outputting the glycan structure based on the nucleotide structure 76. In one or more embodiments, the output (e.g., an image, image data, an image data file, video file, plurality of images frames, a digital file, a file in user-readable format, etc.) may be analyzed by a user, used by another machine that provides output based thereon (e.g., an outputted nucleotide sequence can be used by a DNA synthesizer), etc.

As described herein, a digital file may be any non-transitory medium (e.g., volatile or non-volatile memory, a CD-ROM, a punch card, magnetic recordable tape, etc.) containing digital bits (e.g., encoded in binary, trinary, etc.) that may be readable and/or writeable by processing apparatus (block 34) described herein.

Also, as described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user.

Generally, the methods and systems as described herein may utilize algorithms implementing computational mathematics (e.g., matrix inversions, substitutions, Fourier transform techniques, etc.) to reconstruct enhanced data described herein.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

One will recognize that a graphical user interface may be used in conjunction with the embodiments described herein. The user interface may provide various features allowing for user input thereto, change of input, importation or exportation of files, or any other features that may be generally suitable for use with the processes described herein. For example, the user interface may allow default oligonucleotide sequences to be used or may require entry of certain values, limits, threshold values, or other pertinent information.

More specific description regarding the algorithms used by the exemplary methods and systems described herein will be described within an exemplary framework for the generation of a nucleotide sequence based on the glycan structure and the generation of a glycan structure based on a nucleotide structure.

Exemplary Framework

Figure 11:
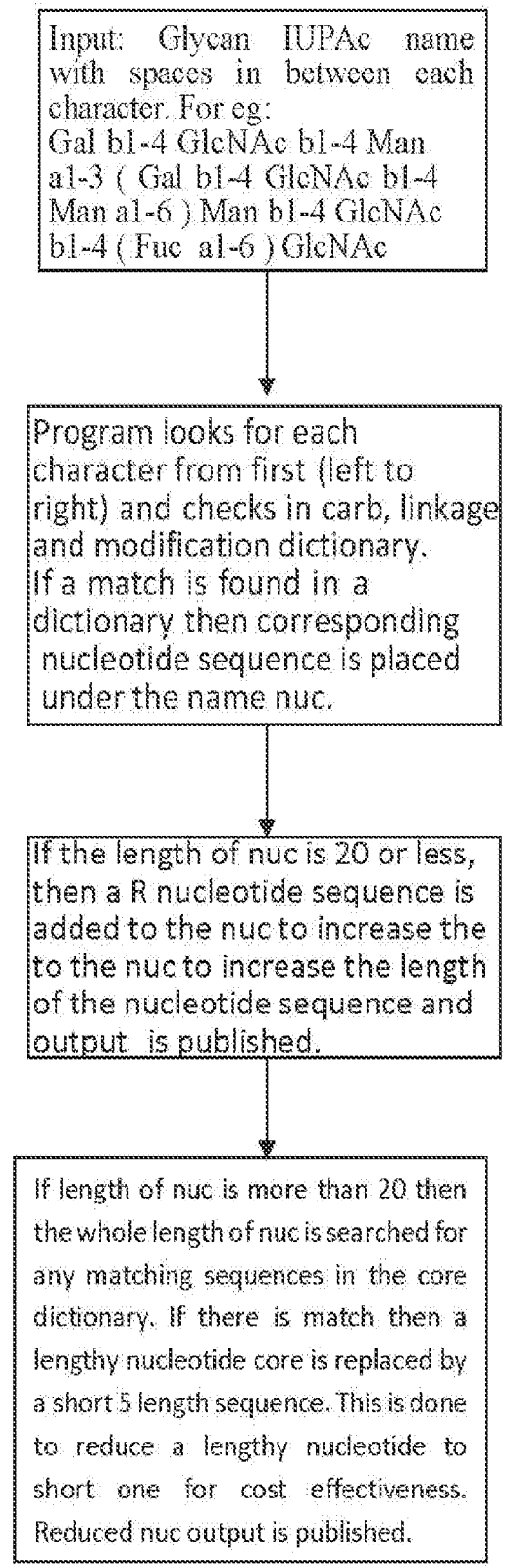
FIG. 11 shows an exemplary embodiment of a method for analyzing a glycan structure according to the present disclosure.

FIG. 11 shows one non-limited embodiment of generating a nucleotide sequence. It includes providing a glycan structure including an input glycan structure, such as an IUPAC name of a glycan with spaces in between each character (e.g., each component). An example of a glycan in IUPAC format with spaces between each component is Gal b1-4 GlcNAc b1-4 Man a1-3 (Gal b1-4 GlcNAc b1-4 Man a1-6) Man b1-4 GlcNAc b1-4 (Fuc a1-6) GlcNAc. The algorithm identifies each component beginning at the left and checks in the datasets for carbohydrate monomers (Table 2), glycosidic linkages (Table 3), and modifications (Table 4). If a match is found in a dataset, then the corresponding oligonucleotide sequence is placed a nucleotide sequence, in the same order of the components in the glycan structure. This is repeated until all components have been assigned an oligonucleotide sequence.

Optionally, if the length of the nucleotide sequence is less than 20, then an extension sequence is added to the nucleotide sequence to increase the length of the nucleotide sequence. If the length of the nucleotide sequence is 20 or greater, then the nucleotide sequence is searched to determine if there is one or more nucleotide sequence that matching the nucleotide sequence of a glycan substructure present in the dataset of Table 4. If there is match, then the nucleotide sequence corresponding to the components of the glycan substructure is replaced by a shorter oligonucleotide for the glycan substructure.

After all components have been assigned an oligonucleotide sequence and the optional extension sequence is added, the nucleotide sequence is generated, where the nucleotide sequence is representative of the entire glycan structure.

Figure 12A:
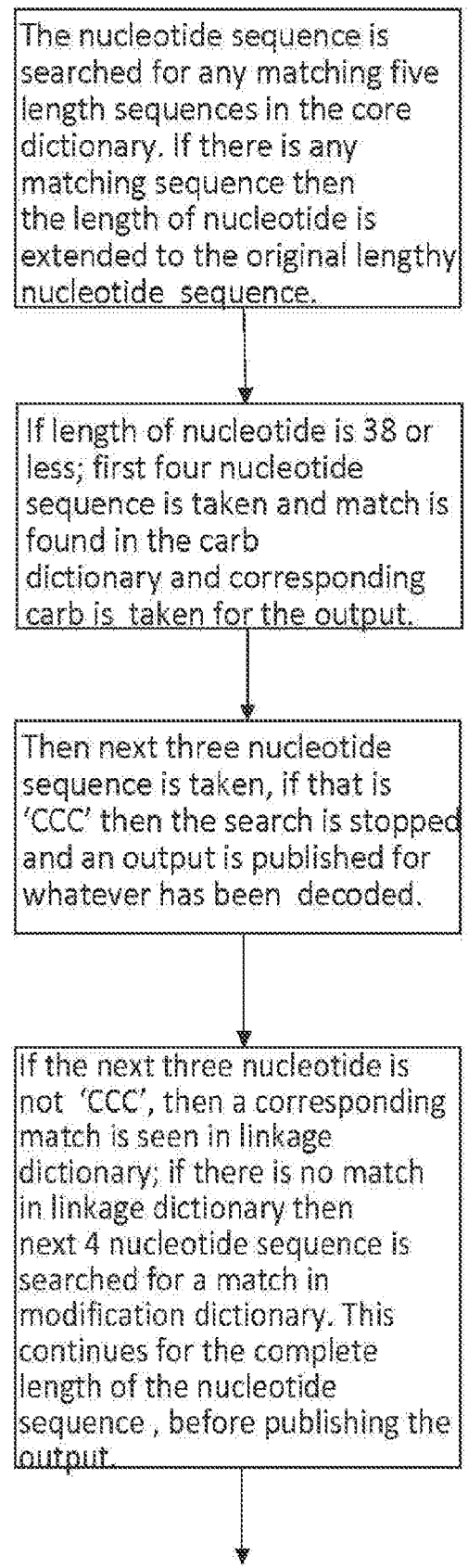
FIG. 12 shows an exemplary embodiment of a method for analyzing a nucleotide sequence according to the present disclosure.
Figure 12B:
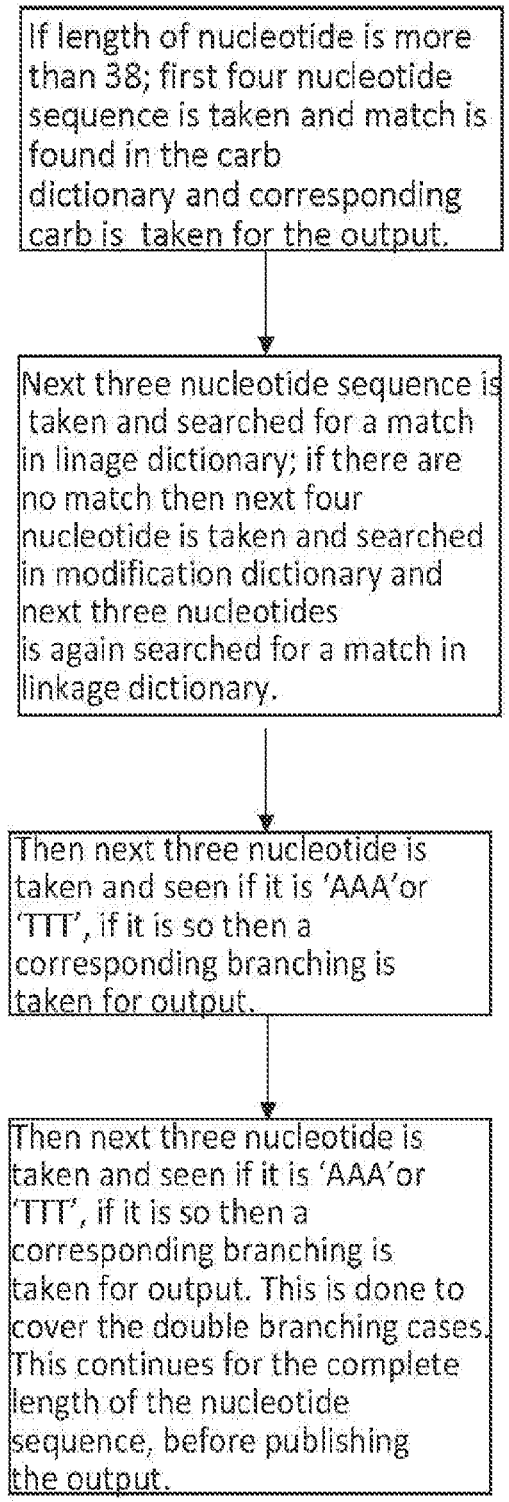

FIG. 12 shows one non-limited embodiment of generating a glycan structure by translating a nucleotide sequence. It includes providing a nucleotide sequence including an input nucleotide sequence, where the nucleotide sequence is representative of a glycan structure. The nucleotide sequence is searched for any oligonucleotides that match an oligonucleotide present in Table 4. If there is any matching oligonucleotide sequence, then the oligonucleotide sequence is removed and replaced by the longer nucleotide sequence corresponding to the components of the glycan substructure.

If length of the nucleotide sequence is no greater than 38, then the first four nucleotides of the nucleotide sequence is compared to the oligonucleotide present in Table 1, and the carbohydrate monomer corresponding to the oligonucleotide is identified. The following oligonucleotides of the nucleotide sequence are compared with the oligonucleotides in Tables 2 and 3. Typically, Table 2 is searched first for a match regarding the glycosidic linkage, and if no match is found then Table 3 is searched for a match regarding a modification present in the most recently identified carbohydrate monomer. If length of the nucleotide sequence is greater than 38, the presence of oligonucleotides corresponding to a branch. This process continues until each oligonucleotide in the nucleotide sequence is linked to a component of the glycan structure, and the complete length of the nucleotide sequence is translated.

EXAMPLES

The present invention is illustrated by the following examples. It is to be understood that the particular examples, materials, amounts, and procedures are to be interpreted broadly in accordance with the scope and spirit of the invention as set forth herein.

Example 1

Design and Synthesis of DNA Encoded Glycan Library

Abstract

DNA encoded libraries (DEL) are used with immense success in screening small molecules for drug discovery. The concept of DEL is even more beneficial for glycans since these complex molecules are extremely difficult to detect itself and often require secondary methods. However, the split and pool method used in DEL is not adaptable in glycans because of the synthetic challenges. Alternatively, we propose here a single step encoding of glycans by click chemistry using predefined structure-based DNA code specific to each glycan. DNA-Glycan conjugates then pooled to get DNA encoded glycan library (DEGL) and used in multiplex detection of glycan binding proteins. As a proof of principle study, we synthesized blood glycans and globo glycans and demonstrated glycan specific DNA encoding, conjugation chemistry, selection and detection using PCR, qPCR and Next Generation Sequencing. Selectivity, specificity and sensitivity of the method were also evaluated and compared with the conventional methods. Overall, DEGL provide a highly sensitive solution phase assay, use of femtomoles of sample, and unprecedented throughput and sample capacity when Next Generation Sequencing platforms are used.

Introduction

Glycans and glycoconjugates are one of the most abundant biomolecules, playing important roles in several biological events such as molecular recognition, adhesion, pathogenesis, and inflammation.[1] Expression patterns of complex carbohydrates are widely altered in cancer, retrovirus infection, atherosclerosis, thrombosis, diabetes, neurodegeneration, arthritis and other diseases. [2] Glycan structures also play a critical role in host defense mechanism as they form a major portion of the antigenic structures, along with other microbe-derived molecules, which are recognized by host immune cells and mount an immune response.[3] With the higher magnitude of significance of glycans in biology, the structural consequences of the interactions of oligosaccharides with receptors of interest are one of the major interests in pharmaceutical research recently. [2, 4]

Nature has provided a systematic, template driven, coded system that has greatly facilitated scientific understanding of nucleic acids and proteins. Similar natural organizing principles do not exist for the incredibly complex myriad carbohydrates (glycans), which also lack UV/fluorescent properties; hence our understanding of glycans is not as advanced. Recent advances in solid phase automated synthesis and enzymatic synthesis have eased the difficulties in obtaining a variety of glycans, but materials available for experimentation remain extremely precious, especially for complex glycans. [5-8] Hence, the development of a highly versatile and ultra-sensitive detection technology is particularly important in the field of carbohydrate research for the characterization of glycan-protein interactions.

Glycan microarrays and ELISA are the most used methods in glycomics for the study of glycan binding proteins. Through glycan arrays, many glycans can be analyzed simultaneously but sample throughput is often limited. Meanwhile, ELISA can handle many samples simultaneously but the number of glycans analyzed is limited because often one glycan per well is analyzed in a single run. Also, these two methods are not suitable in clinical settings since microarray has the disadvantage of requiring specific instrumentations while ELISA is not suitable for high throughput sample analysis.[3, 9-11] In another pioneering work called multiplex glycan bead array (MGBA) the use of colored Luminex™ beads for the multiplex detection of glycan binding proteins was reported,[12] which is certainly improved in magnitude and throughput, but still require instrumentation specifically for this use. Alternatively, we propose here DNA-encoded glycan libraries (DEGLs), which has enormous potential in terms of sample and glycan throughput, assay sensitivity and amenable to quick adjustments for specific assay requirement. Moreover, the method can be easily applied in wide spread research community as well as in clinical labs, since there is no requirement of any additional instrumentation other than the routine molecular biology instrumentation.

Encoding a small molecule with a piece of DNA enhances the detection limit of the small molecule many-fold by polymerase chain reaction (PCR).[13] Although the concept of DNA encoding was introduced in 1992, it has gained momentum recently with the advancement in DNA next generation sequencing (NGS) technologies and involved in many of the discovery of new lead molecules recently.[14-16] The technology, also referred as DEL, generally adopt split and pool library synthesis, which is practically suited for the construction of libraries spanning millions to billions of small molecules.[17] But, the split and pool synthesis is not suitable in the highly complicated glycan synthesis. In this work, we introduce a structure-based representation of glycans using DNA codes, specifically for adopting DEL technologies in glycomics.

Kwon and coworkers showed the feasibility of using DNA tag in glycomics; their work coined Glyco-PCR, successfully demonstrated detection glycan-binding proteins (GBP) using DNA conjugated glycans with high sensitivity.[18, 19] Although, the method asserted the ultra-sensitive detection by DNA amplification, it hasn't addressed how a large pool of glycans can be analyzed with an affordable cost. More recently, DNA encoded library involving glycans were synthesized by bio catalysis and split and pool,[20] again with very limited synthetic utility. With the extremely complex nature of glycan synthesis, split and pool is not suitable for the synthesis of DNA Encoded Glycan Library (DEGL) spanning to the entire glycans. Hence, we choose to incorporate all known glycan structures to the DEGL using single step coding of pre-synthesized glycans with the corresponding DNA sequence. Though custom synthesis of such DNA sequences is possible and pragmatic for small DEGLs, it would be a cost-prohibitive option when dealing with hundreds of sugars, and hence compromising on the enormous potential of high throughput analysis. These challenges are certainly inevitable but assuming the bigger prospect of DEGLs prompted us to think about different options to alleviate this problem. Unlike small molecules or proteins, number of biologically relevant glycans are relatively small and most of the known glycan structures are deposited in different glycan databases. [21] In effect, we only need that many of DNA sequences to cover the whole DEGL and it is certainly practical to synthesize and store 20000 or 50000 of DNA sequences for future use in DEGL technologies. To achieve this and retain a library of DEGL and extend the scope of library many fold with the contributions from many research groups, similar to the consortium of functional glycomics (CFG) glycan microarray depositories, a broadly acceptable protocol exclusively for glycans, from the synthesis of DEGL to final data analysis, would be helpful.[22, 23] It is worthy to note here that, cataloging DNA codes for glycans can also achieved by selecting random DNA codes, but we wanted to use the full potential of what DNA manipulation has to offer in functional glycomics; which is only possible when DNA code feature the structural information of glycan in question. For instance, structurally defined DNA code will help the design of qPCR probes based on the glycan sequences in the library, which is not possible in random DNA coding. qPCR probes specific to the glycan epitopes ensure another dimension of DEGL which will be particularly suited in diagnostics and clinical applications.

To achieve the ubiquitous use of DNA codes, we require systematic selection of DNA codes, highly feasible DNA-glycan conjugation chemistry, and detection procedures. Here, we address all three issues, firstly, an in-house software program (available on the world wide web at 131.96.145.142:8000/cgi-bin/form.py) was developed for generating a DNA code specifically for each glycan. Next, the DNA code amended with primers and 5' hexynyl modification was 'click' conjugated with the corresponding azido-glycan, and finally, selection and detection methods were evaluated. As a proof of principle study, we synthesized blood glycans and globo glycans and demonstrated glycan specific DNA encoding, conjugation chemistry, selection and detection using PCR, qPCR and Next Generation Sequencing. Selectivity, specificity and sensitivity of the method were also evaluated and compared with the conventional methods.

Results and Discussion

Systematic Coding of Glycans

The first aim was to develop a unique DNA coding method that would be consistent with the existing representation of glycans, so that any glycans known or yet to be characterized can get a unique DNA sequence. Unlike peptides, proteins, and genetic materials, representation of carbohydrates brings many challenges. A detailed and accurate depiction of glycans should feature composition, sequence, branching position, possible modifications, and anomeric configuration. Kornfeld et al. first proposed the use of symbols to depict carbohydrates,[24] and this approach has since replaced the IUPAC naming,[25] with modifications adapted time to time to fit the entire glycome.[26, 27] All these approaches are based on different shapes and color codes to represent the building blocks (FIG. 13), which gave us the idea of using nucleotide bases to represent the building blocks. The number of shapes and colors we could use for the representation are infinite, but only four nucleotide bases A, T, G, and C available for DNA coding. Hence, we depended on permutation and combination approach to cover the whole glycome. The number of sugar monomers are more than one hundred, and they can be incorporated into the oligosaccharide in multiple ways, making glycan structural information more complex. These inherent difficulties prompted us to develop a dedicated computer program that could sort the structural information to coding vocabulary and transform IUPAC names to single-stranded DNA code. For natural adaptation of the codes into functional glycomics, the codes should be of minimum length but still code all the information and enabling PCR amplification.

Figure 13:
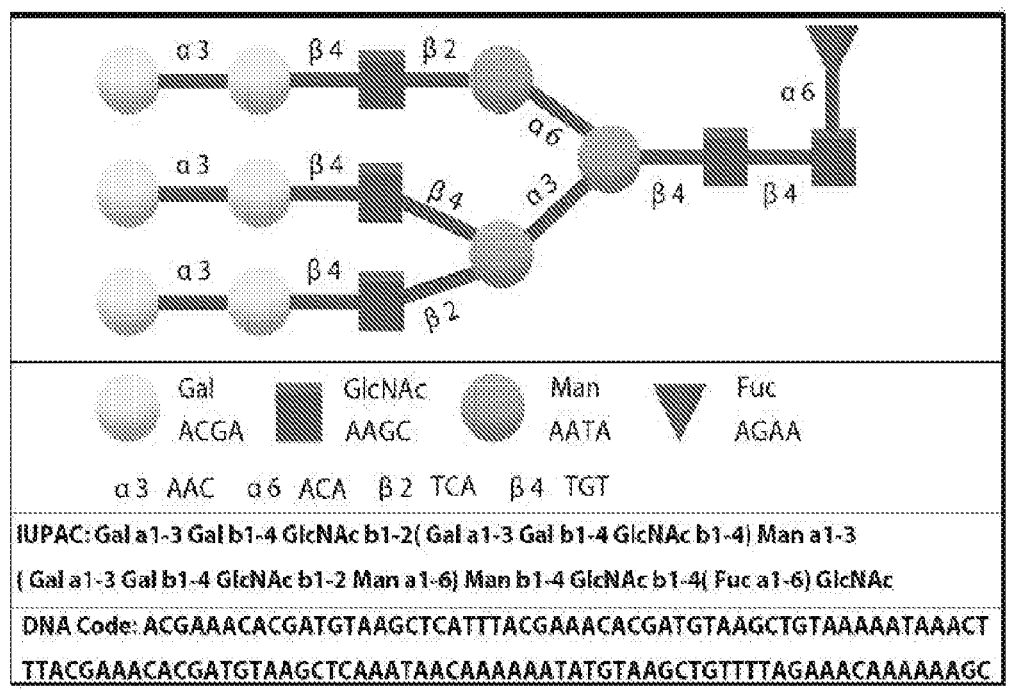
FIG. 13 shows different representations of a glycan. DNA code is SEQ ID NO:22.

Structure-based coding must have a controlled vocabulary of the structural components. For attaining this goal, similar to the CFG representations, we split the structural information of the carbohydrate into the monosaccharide building blocks and the linkages (FIG. 13). Then we created two libraries, and gathered all monomers into library A and different linkages to library B. Next, the monomers in the library A assigned with a unique four-letter code. There are 256 possible combinations with the four letters A, T, G, and C. More than 70 monomers were added to this library (Table 1), effectively using about 70 randomly-generated codes. Similarly, all possible linkages generally present in the glycans were organized in library B and coded with 3 letters. Thirty-six linkages are currently in this library with further space for future additions (Table 2). Many glycans feature functional group modifications as part of the structure, and to add this information we added a third library (library C, Table 3). More than 100 modifications were identified and added to the library and assigned four letter codes which were not used in the library A. Any special characters like '(' used in the IUPAC input were also incorporated with specific codes. Finally, we consolidated these libraries into a Python-based program, and several rounds of evaluations performed with the input of diverse glycan structures. A sample library of 100 glycans was tested, and the program successfully delivered codes for all the glycans tested (Table 5). A sequence length between 25 to 100 bases ideally fit the PCR applications and, among the 100 glycans randomly selected most of them fell in this limit, but few glycans had sequence length smaller or higher than the range specified. Through the careful observation of the sample pool, we identified many of the repeating fragments in the glycans (e.g., six sugar core structure of N-glycans). Hence, we assumed taking this as a single block would reduce the overall length of the codes of long glycans, and a fourth library (library D, Table 4) was added to the program featuring many of the most common building blocks found in the glycans. For the glycans possessing a code smaller than the 25 bases, a random sequence of 20-base DNA was added to the code with a special mention in the program to avoid misinterpretation. These two modifications allowed us to keep the sequence length within the desired limits.

TABLE 5

Examples of DNA encoding of glycans.

| Structure | Long Nucleotide | Length | Short Nucleotide | Length |
|---|---|---|---|---|
| | acgctgtttagaaagaaaagctgtaataaactttacgct gtttagaaagaaaagctgtaataacaaaaatatgtaa gctgttttagaaacaaaaagc (SEQ ID NO: 18) | 105 | acgctgtttagaaagaaaa agctgtaataaacttacgctg tttagaaaagaaaagctgt aataacaaagtaca (SEQ ID NO: 121) | 79 |
| | Acgatgtaagctgtaataaactttacgatgtaagctgtaat aacaaaaatatgtaagctgttttagaaacaaaaagc (SEQ ID NO: 19) | 79 | gtacgaataaactttacgatgt aagctgtaataacaaagtac a (SEQ ID NO: 122) | 44 |
| | Acgatgtaagctgtaataaactttaagctgtaataacaaaa aatatgtaagctgttttagaaacaaaaagc (SEQ ID NO: 20) | 72 | gtacgaataaacttaagctgt aataacaaagtaca (SEQ ID NO: 123) | 37 |

TABLE 5-continued

Examples of DNA encoding of glycans.

| Structure | Long Nucleotide | Length | Short Nucleotide | Length |
|---|---|---|---|---|
| | acgatggtctctttacgatgggttaaaaagctgtaagctca aataaactttacgatgggttaacgatgggtctctttacgatgg gtaaaaagctgtaagctcaaataacaaattatcatcaa aaaatatgtaagctgttttagaaacaaaaagc (SEQ ID NO: 21) | 159 | acgatggtctctttacgatggg ttaaaaagctgtaagctcaa ataaactttacgatgggttaac gatggtctctttacgatggtt aaaaagctgtaagctcaaat aacaaattatcatcaaagt ca (SEQ ID NO: 124) | 133 |
| | acgaaacacgatgtaagctcatttacgaaacacgatgtaa gctgtaaaataaacttacgaaacacgatgtaagctgaaaa taacaaaaatatgtaagctgttttagaaacaaaaagc (SEQ ID NO: 22) | 120 | acgaaacacgatgtaagctc atttacgaaacgtacgaaaaa taaacttgtaccaataacaaa agtaca (SEQ ID NO: 125) | 69 |

TABLE 5-continued

Examples of DNA encoding of glycans.

| Structure | Long Nucleotide | Length | Short Nucleotide | Length |
|---|---|---|---|---|
| | acgaaacacgatgtaagctcatttacgatgtaagctgtaaa aataaactttacgaaacacgatgtaagctcaaataacaaa aatatgtaagctgttttagaaacaaaaagc (SEQ ID NO: 23) | 113 | acgaaacacgatgtaagctc atttgtacgaaaataaacttt gtaccaataacaaagtaca (SEQ ID NO: 126) | 62 |
| | acgaaacacgatgtaagctcaaataaactttacgaaacac gatgtaagctccaaataacaaaatatgtaagctgttttaga aacaaaaagc (SEQ ID NO: 24) | 93 | gtaccaataaactttacgaaa cacgatgtaagctccaaataac aaagtaca (SEQ ID NO: 127) | 51 |
| | acgaaacacgatgtaagctcaaataaactttacgatgtaag ctcaaataacaaaatatgtaagctgttttagaaacaaaa aagc (SEQ ID NO: 25) | 86 | gtaccaataaactttacgatgt aagctcaataacaaagta ca (SEQ ID NO: 128) | 44 |
| | acgaaacacgatgtaagctcaaataaactttaagctcaaat aacaaaaatatgtaagctgttttagaaacaaaaagc (SEQ ID NO: 26) | 79 | gtaccaataaactttaagctca aataacaaagtaca (SEQ ID NO: 129) | 37 |

TABLE 5-continued

Examples of DNA encoding of glycans.

| Structure | Long Nucleotide | Length | Short Nucleotide | Length |
|---|---|---|---|---|
| | acgaaacacgatgtaagctcaaataaacttaataacaaaa aatatgtaagctgttttagaaacaaaaaagc (SEQ ID NO: 27) | 72 | gtaccaataaacttaataaca aagtaca (SEQ ID NO: 130) | 30 |
| | acgaaacacgatgtaagctcttttacgaaacacgatgtaa gcttaaaaacgatgtaagctcaaataaacttacgaaacac gatgtaagctcaaataacaaaaaatatgtaagctgttttaga aacaaaaagc (SEQ ID NO: 28) | 134 | gtatttttacgaaacacgatgt aagcttaaaaacgatgtaag ctcaataaacttgtaccaat aacaaaagtaca (SEQ ID NO: 131) | 76 |
| | acgatgtaagctcattacgatctaagctgtaaaataaact ttacgatgtaagctcattacgatgtaagcttaaataac aaaaatatgtaagctgttttagaaacaaaaaagc (SEQ ID NO: 29) | 119 | acgatgtaagctcattgttca aaaataaacttacgatgta agctcattacgatgtaagctt aacaaataacaaaagtaca (SEQ ID NO: 132) | 84 |

TABLE 5-continued

Examples of DNA encoding of glycans.

| Structure | Long Nucleotide | Length | Short Nucleotide | Length |
|---|---|---|---|---|
| | acgatgtaagctcatttacgatgtttagaaacaaaaagctgtaaaaataaactttacgatgtaagctgatgtaagctcaaataacaaaaatatgtaagctgttttagaaacaaaaagc (SEQ ID NO: 30) | 112 | acgatgtaagctcatttgtagaaaataaactttacgatgtaagctcaaataacaaaagtaca (SEQ ID NO: 133) | 64 |
| | acgatgtaagctcatttacgatgtaagctgtaaaataaactaacttacgaaacacgatgtaagctcaataacaaaaatatgtaagctgttttagaaacaaaaagc (SEQ ID NO: 31) | 106 | acgatgtaagctcatttgtacgaaaataaactttgtaccaataacaaagtaca (SEQ ID NO: 134) | 55 |
| | acgatgtaagctcatttacgatgtaagctgtaaaataaactttacgatgtaagctcatttacgatgtaagcttaaaataacaaaaatatgtaagctgtttagaaacaaaaagc (SEQ ID NO: 32) | 119 | acgatgtaagctcatttgtacgaaaataaactttacgatgtaagctcatttacgatgtaagcttaaaataacaaaagtaca (SEQ ID NO: 135) | 84 |

TABLE 5-continued

Examples of DNA encoding of glycans.

| Structure | Long Nucleotide | Length | Short Nucleotide | Length |
|---|---|---|---|---|
| | acgatgttttagaaacaaaagctcaataaactttaataa actttaataacaaaaaataacaaaatatgtaagctgtttta gaaacaaaaagc (SEQ ID NO: 33) | 98 | acgatgttttagaaacaaaa agctcaaataaactttaataa ctttaataacaaaaaataaca aaagtaca (SEQ ID NO: 136) | 72 |
| | acgatgttttagaaacaaaagctcaaataaactttacgat gtaagctcaaataaactttacgat gtaagctgttttagaaa caaaaaagc (SEQ ID NO: 34) | 92 | acgatgttttagaaacaaaa agctcaaataaactttacgat gtaagctcaaataacaaaagt aca (SEQ ID NO: 137) | 66 |
| | acgatgttttagaaacaaaagctcaaataaactttaataa caaaaatatgtaagctgttttagaaacaaaaagc (SEQ ID NO: 35) | 78 | acgatgttttagaaacaaaa agctcaaataaactttaataac aaagtaca (SEQ ID NO: 138) | 52 |

TABLE 5-continued

Examples of DNA encoding of glycans.

| Structure | Long Nucleotide | Length | Short Nucleotide | Length |
|---|---|---|---|---|
| | acgatctaagctgtaagcagtttaagcagtaaaaataaac ttaataagtaataacaaacaaaaatatgtaagctgttttagaaac aaaaagc (SEQ ID NO: 36) | 92 | gtcaaagcagtttaagcag taaaataacttaataagta ataacaaagtaca (SEQ ID NO: 139) | 57 |
| | acgatgttttagaaaacaaaaagctcattacgatgtaagct gtaaaataacttacgatgtaagctcaaataacaaaaaa tatgtaagctgtttagaacaaaaaagc (SEQ ID NO: 37) | 112 | acgatgttttagaaacaaaa agtcattgtacgaaaaata aacttacgatgtaagctcaa ataacaaaagtaca (SEQ ID NO: 140) | 77 |

TABLE 5-continued

Examples of DNA encoding of glycans.

| Structure | Long Nucleotide | Length | Short Nucleotide | Length |
|---|---|---|---|---|
| | acgatgtttagaaacaaaacaaaaagctcattacgatgttttag aaaacaaaaagctaaaataaacttacgatgttttagaa aacaaaaagctcaaataacaaaatgtaagctgttta gaaacaaaaagc (SEQ ID NO: 38) | 138 | acgatgtttagaaacaaaa agctcatttgtgaaaaata aacttacgatgttttagaaa caaaagctcaaataacaa agtaca (SEQ ID NO: 141) | 90 |
| | acgatgtttagaaacaaaaagctcaaataaacttacgat gtttagaaacaaaacaaaaagctcaaataacaaaaatatgtaa gctgtttagaaacaaaaagc (SEQ ID NO: 39) | 105 | acgatgtttagaaacaaaa agctcaaataaacttacgat gtttagaaacaaaagctc aataacaaagtaca (SEQ ID NO: 142) | 79 |
| | acgatgtaagctcaaataacttacgatgtaagctcattta cgctgtcaagctaaaataacaaaaatatgtaagctgttt tagaaacaaaaagc (SEQ ID NO: 40) | 99 | acgatgtaagctcaaataac tttacgatgtaagctcattgtg tcaaaataacaaaagtaca (SEQ ID NO: 143) | 64 |

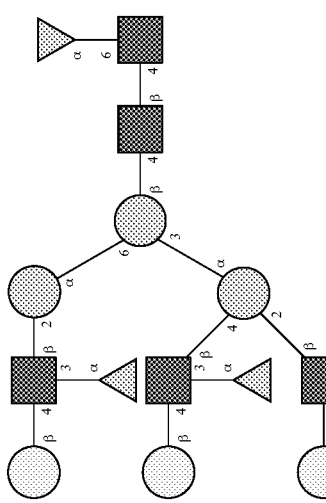
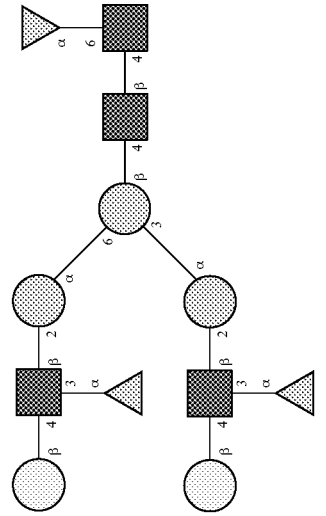
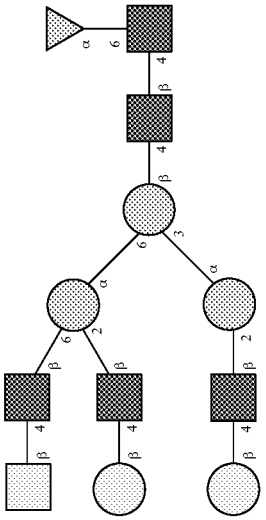

TABLE 5-continued

Examples of DNA encoding of glycans.

| Structure | Long Nucleotide | Length | Short Nucleotide | Length |
|---|---|---|---|---|
| | acgatgtaagctcaaataacattacgatgtaagctcatta cgctgtaagcttaaaaataacaaaaatatgtaagctgttt tagaaacaaaaagc (SEQ ID NO: 41) | 99 | acgatgtaagctcaaataaca tttacgatgtaagctcattgtg tcaaaataaacaaagtaca (SEQ ID NO: 144) | 64 |
| | acgatgtaagctcaaataacttacgctgtaagctcatta cgatgtaagcttaaaaataacaaaaatatgtaagctgttt tagaaacaaaaagc (SEQ ID NO: 42) | 99 | acgatgtaagctcaaataaac tttgtttcttacgatgtaag cttaaaaataacaaaagtaca (SEQ ID NO: 145) | 64 |
| | acgatgtaagctcaaataaaatttaggggttacgatgtaag ctcaataacaaaaatatgtaagctgttttagaaacaaaa aagc (SEQ ID NO: 43) | 86 | acgatgtaagctcaaataaac ttagggtttacgatgtaagct caataacaaagtaca (SEQ ID NO: 146) | 60 |
| | acgatgtaagctcaaataaacttaataagaataacaat aacaaaaatatgtaagctgttttagaaacaaaagc (SEQ ID NO: 44) | 79 | acgatgtaagctcaaataaac tttaataagaataaacaataa caaagtaca (SEQ ID NO: 147) | 53 |

TABLE 5-continued

Examples of DNA encoding of glycans.

| Structure | Long Nucleotide | Length | Short Nucleotide | Length |
|---|---|---|---|---|
| | acgatgtaagctcaaataaacttaataacttaatacaa aaaataacaaaaatatgtaagctgtttagaaacaaaa gc (SEQ ID NO: 45) | 85 | acgatgtaagctcaaataaac tttaataaactttaataacaa aatacaaagtaa (SEQ ID NO: 148) | 59 |
| | acgatgtaagctcaaataaacttacgctgtaagctcaaat aacaaaaatatgtaagctgtttagaaacaaaaaagc (SEQ ID NO: 46) | 79 | acgatgtaagctcaaataaac ttgtttcaataacaaagtac a (SEQ ID NO: 149) | 44 |
| | acgatgtaagctcaaataaacttaagctcaaataacaaa aatatgtaagctgtttagaaacaaaaaagc (SEQ ID NO: 47) | 72 | acgatgtaagctcaaataaac tttaagctcaaataacaaag taca (SEQ ID NO: 150) | 46 |
| | acgatgtaagctcaaataaacttacgatgtaagctcaaat aacaaaaatatgtaagctgtttagaaacaaaaaagc (SEQ ID NO: 48) | 79 | acgatgtaagctcaaataaac tttacgatgtaagctcaataa caaagtaca (SEQ ID NO: 151) | 53 |

TABLE 5-continued

Examples of DNA encoding of glycans.

| Structure | Long Nucleotide | Length | Short Nucleotide | Length |
|---|---|---|---|---|
| | acgatgtaagctcaaataaactttacgatgtaagctcatta cgatgtaagcttaaaataacaaaatatgtaagctgttt tagaaacaaaaagc (SEQ ID NO: 49) | 99 | acgatgtaagctcaaataaac tttacgatgtaagctcattgtg cgaaaataacaaaagtaca (SEQ ID NO: 152) | 64 |
| | acgatgtaagctcaaataaactttacgatgtaagctcatta cgaacacgatgtaagcttaaaataacaaaatatgt aagctgtttagaaacaaaaagc (SEQ ID NO: 50) | 106 | acgatgtaagctcaaataaac tttacgatgtaagctcatttac gaacgtgcgaaaataaca aagtaca (SEQ ID NO: 153) | 71 |
| | acgatgtaagctcaaataaactttacgaacacgatgtaag ctcatttacgatgtaagcttaaaataacaaaatatgta agctgtttagaaacaaaaagc (SEQ ID NO: 51) | 106 | acgatgtaagctcaaataaac tttacgaacacgatgtaagc tcatttgtgcgaaaataaca aagtaca (SEQ ID NO: 154) | 71 |

TABLE 5-continued

Examples of DNA encoding of glycans.

| Structure | Long Nucleotide | Length | Short Nucleotide | Length |
|---|---|---|---|---|
| | acgatgtaagctcatttaggcggtacgatgtaagctgtaaa<br>aataaactttaggcgtacgatgtaagctcatttaggcggt<br>acgatgtaagcttaaaaataacaaaaatatgtaagctgt<br>tttagaaacaaaaagc (SEQ ID NO: 52) | 140 | acgatgtaagctcatttaggc<br>ggtacgatgtaagctgtaaa<br>ataacttaggcggtacgat<br>gtaagctcatttggtgtaaa<br>ataacaaagtaca (SEQ<br>ID NO: 155) | 98 |
| | acgatgtaagctcatttaggcggtacgatgtaagctgtaaa<br>aataaactttaggcggtacgatgtaagctcatttacgatgta<br>agcttaaaaataacaaaaatatgtaagctgttttagaaac<br>aaaaagc (SEQ ID NO: 53) | 133 | acgatgtaagctcatttgg<br>aaaaataaactttaggcggt<br>acgatgtaagctcatttgtgc<br>gaaaataacaaagtaca<br>(SEQ ID NO: 156) | 82 |
| | acgatgtaagctcatttaggcggtacgatgtaagctgtaaa<br>aataaactttaggcggtacgatgtaagctcatttacgatgta<br>agcttaaaaataacaaaaatatgtaagctgttttagaaac<br>aaaaagc (SEQ ID NO: 53) | 133 | acgatgtaagctcatttgg<br>aaaaataaactttaggcggt<br>acgatgtaagctcatttgtgc<br>gaaaataacaaagtaca<br>(SEQ ID NO: 156) | 82 |

TABLE 5-continued

Examples of DNA encoding of glycans.

| Structure | Long Nucleotide | Length | Short Nucleotide | Length |
|---|---|---|---|---|
| | acgatgtaagctcatttacgatgtaagctgtaaaataaact ttaggcggtaagctaagctcattaggcggtacgatgta agcttaaaaataacaaaaatatgtaagcgtgttttagaaac aaaaagc (SEQ ID NO: 54) | 133 | acgatgtaagctcattacgat gtaagctgtaaaataaacttt aggcggtacgatgtaagctc atttgtgtaaaataacaaa agtaca (SEQ ID NO: 157) | 91 |
| | acgatgtaagctcatttacgatgtaagctgtaaaataaact ttaagctcaaataacaaaaatatgtaagctgttttagaaac aaaaagc (SEQ ID NO: 55) | 92 | acgatgtaagctcatttgtac gaaaataaactttaagctca aataacaaagtaca (SEQ ID NO: 158) | 57 |
| | acgatgtaagctcatttacgatgtaagctgtaaaataaact ttacgatgtaagctcaaataacaaaaatatgtaagctgtttt agaacaaaaagc (SEQ ID NO: 56) | 99 | acgatgtaagctcatttgtac gaaaataaactttacgatgt aagctcaaataacaaagta ca (SEQ ID NO: 159) | 64 |

TABLE 5-continued

Examples of DNA encoding of glycans.

| Structure | Long Nucleotide | Length | Short Nucleotide | Length |
|---|---|---|---|---|
| | acgatgtaagctgtaataacttaataacaaaaatgta agctgttttagaaacaaaaagc (SEQ ID NO: 57) | 65 | gtacgaataaacttaataac aaagtaca (SEQ ID NO: 160) | 30 |
| | acgatgtaagctctacgatgtaagctcaataaactttacg atgtaagctcaaataacaaaaatatgtaagctgttttagaa acaaaaagc (SEQ ID NO: 58) | 93 | acgatgtaagctctacgatgt aagctcaaataaactttacga tgtaagctcaaataacaaaag taca (SEQ ID NO: 161) | 67 |
| | acgatgtaagctctacgatgtaagctcattacgatgtaag ctgtaaaataaactttacgatctacgatgtccgatgtaagc tcattacgatgtaagctctacgatgtaagcttaaaaataa caaaaatatgtaagctgttttagaaacaaaaagc (SEQ ID NO: 59) | 161 | acgatgtaagctctacgatgt aagctcattacgatgtaagct gtaaaataaactttacgatgt aagctctacgatgtaagctca tttacgatgtaagctctgtgcg aaaaataacaaagtaca (SEQ ID NO: 162) | 126 |

TABLE 5-continued

Examples of DNA encoding of glycans.

| Structure | Long Nucleotide | Length | Short Nucleotide | Length |
|---|---|---|---|---|
| | acgctgttttagaaacaaaaagctcaaataaacttaggc ggtacgctgtaagctgtcaaataacaaaaatatgtaagctgt tttagaaacaaaaagc (SEQ ID NO: 60) | 99 | acgctgttttagaaacaaaa agctcaaataaacttaggcg gtgtttcaataacaaaagtac a (SEQ ID NO: 163) | 64 |
| | acgctgttttagaaacaaaacaaaagctcaaataaacttaataa caaaaatatgtaagctgttttagaaacaaaaagc (SEQ ID NO: 61) | 78 | acgctgttttagaaacaaaa agctcaaataaacttaataac aaaagtaca (SEQ ID NO: 164) | 52 |
| | acgctgttttagaaacaaaacaaaagctcaaataaacttaataa caaaaatatgtaagctgttttagaaacaaaaagc (SEQ ID NO: 61) | 78 | acgctgttttagaaacaaaa agctcaaataaacttaataac aaaagtaca (SEQ ID NO: 164) | 52 |

TABLE 5-continued

Examples of DNA encoding of glycans.

| Structure | Long Nucleotide | Length | Short Nucleotide | Length |
|---|---|---|---|---|
| | acgctgtttagaaacaaacaaaaagctcaaataaacttacgct gtaagctcaaataacaaaaaatatgtaagctgtttagaaa caaaaagc (SEQ ID NO: 62) | 92 | acgctgtttagaaacaaaa agctcaaataaacttgtttca ataacaaaagtaca (SEQ ID NO: 165) | 57 |
| | acgctgtttagaaacaaacaaaaagctccaaataaacttacga aacacgatgtaagctcaataacaaaaaatatgtaagctgt tttagaaacaaaaagc (SEQ ID NO: 63) | 99 | acgctgtttagaaacaaaa agctccaaataaacttgtacc aataacaaagtaca (SEQ ID NO: 166) | 57 |
| | acgccatttgtaagctcaaataacttaataacaataaca aaaatatgtaagctgtttagaaacaaaaagc (SEQ ID NO: 64) | 76 | acgccatttgtaagctcaaat aactttaataacaataaca aaagtaca (SEQ ID NO: 167) | 50 |
| | acgccatttgtaagctcaaataaacttacgctgtaagctca aataacaaaaaatatgtaagctgtttagaaacaaaaaga (SEQ ID NO: 65) | 83 | acgccatttgtaagctcaaat aacttgtttcaataacaaaa gtaca (SEQ ID NO: 168) | 48 |

TABLE 5-continued

Examples of DNA encoding of glycans.

| Structure | Long Nucleotide | Length | Short Nucleotide | Length |
|---|---|---|---|---|
| | acgccatttgtaagctcaaataaacttaggcggtacgatgtaagctcaaataacaaaaatatgtaagctgttttagaaacaaaaagc (SEQ ID NO: 66) | 90 | acgccatttgtaagctcaaataacttaggcggtacgatgtaagctcaaataacaaaagtaca (SEQ ID NO: 169) | 64 |
| | acgccatttgtaagctcaaataaacttaggcgttacgatgtaagctcaaataacaaaaatatgtaagctgttttagaaaca (SEQ ID NO: 67) | 90 | acgccatttgtaagctcaaataacttaggcgttacgatgtaagctcaaataacaaaagtaca (SEQ ID NO: 170) | 64 |
| | acgctgtaagctcaaataacttaagctcatttacgctgtaagctcaaataaatatgtaagctgttttagaaacaaaaagc (SEQ ID NO: 68) | 92 | acgctgtaagctcaaataaactttaagctcatttgtcaaaataacaaagtaca (SEQ ID NO: 171) | 57 |
| | acgctgtaagctcaaataacttaagctcatttaagcttaaaataacaaaaatatgtaagctgttttagaaacaaaaagc (SEQ ID NO: 69) | 85 | gtttcaataaacttaagctcattaagcttaaaaaataacaaagtaca (SEQ ID NO: 172) | 50 |

TABLE 5-continued

Examples of DNA encoding of glycans.

| Structure | Long Nucleotide | Length | Short Nucleotide | Length |
|---|---|---|---|---|
| | acgctgtaagctcaaataaactttaataacaaaaatatgta agctgtttttagaaaacaaaaagc (SEQ ID NO: 70) | 65 | gtttcaataaactttaataaca aaagtaca (SEQ ID NO: 173) | 30 |
| | acgctgtaagctcaaataaactttaggcgttacgatgtaag ctcaaataacaaaaatatgtaagctgtttttagaaaacaaaa aagc (SEQ ID NO: 71) | 86 | gtttcaataaactttaggcgtt acgatgtaagctcaaataaca aagtaca (SEQ ID NO: 174) | 51 |
| | acgctgtaagctcaaataaactttaataacaaaaatatgta agctgtttttagaaaacaaaaagc (SEQ ID NO: 70) | 65 | gtttcaataaactttaataaca aaagtaca (SEQ ID NO: 173) | 30 |
| | acgctgtaagctcaaataaactttacgccattgtaagctca ataacaaaaatatgtaagctgtttttagaacaaaaagc (SEQ ID NO: 72) | 83 | gtttcaataaactttacgccatt tgtaagctcaaataacaaaag taca (SEQ ID NO: 175) | 48 |

TABLE 5-continued

Examples of DNA encoding of glycans.

| Structure | Long Nucleotide | Length | Short Nucleotide | Length |
|---|---|---|---|---|
| | acgctgtaagctcaaataaactttacgatgtaagctcatta cgatgtaagcttaaaaataacaaaaatatgtaagctgttt tagaaacaaaaagc (SEQ ID NO: 73) | 99 | gtttcaataaactttacgatgt aagctcatttgtgcgaaaat aacaaagtaca (SEQ ID NO: 176) | 55 |
| | acgctgtaagctcaaataaactttacgatgtaagctcaaat aacaaaaatatgtaagctgttttagaaacaaaaagc (SEQ ID NO: 74) | 79 | gtttcaataaactttacgatgt aagctcaataacaaaagta ca (SEQ ID NO: 177) | 44 |
| | acgctgtaagctcattacgatgtaagctcgatgtaagctaaaaataaact ttacgtgtaagctcattacgatgtaagctaagcttaaaaataac aaaaatatgtaagctgttttagaaacaaaaagc (SEQ ID NO: 75) | 119 | gtttcttacgatgtaagctgta aaataaactttacgctgtaa gctcatttgtgcgaaaataa caaagtaca (SEQ ID NO: 178) | 75 |

TABLE 5-continued

Examples of DNA encoding of glycans.

| Structure | Long Nucleotide | Length | Short Nucleotide | Length |
|---|---|---|---|---|
| (glycan structure 1) | acgctgtaagctcattacgatgtaagctgtaaaataaact ttacgatgtaagctcaaataacaaaaatatgtaagctgtttt agaacaaaaagc (SEQ ID NO: 76) | 99 | gtttcttgtcctaaaataaac tttacgatgtaagctcaaata caaagtaca (SEQ ID NO: 179) | 55 |
| (glycan structure 2) | acgctgtaagctcattacgatgtaagctgtaaaataaact ttacgctgtaagctcattacgctgtaagcttaaaataac aaaaatatgtaagctgttttagaacaaaaagc (SEQ ID NO: 77) | 119 | acgctgtaagctcattacgat gtaagctgtaaaataacttt acgctgtaagctcattgtc aaaaataacaaaagtaca (SEQ ID NO: 180) | 84 |
| (glycan structure 3) | acgctgtaagctcatttaagctgtaaaataaacttaagct catttaagcttaaaataacaaaaatatgtaagctgtttta gaacaaaaagc (SEQ ID NO: 78) | 98 | gttgaaataaacttaagctca tttaagcttaaaataacaaa agtaca (SEQ ID NO: 181) | 50 |

TABLE 5-continued

Examples of DNA encoding of glycans.

| Structure | Long Nucleotide | Length | Short Nucleotide | Length |
|---|---|---|---|---|
| | acgctgtaagctcattaagctgtaaaataaacttacgct gtaagctcatttaagcttaagcttaaaaataacaaaaatatgtaag ctgttttagaaacaaaaaagc (SEQ ID NO: 79) | 105 | gtttcttaagctgtaaaata aacttagctgtaagctcatt taagcttaaaaataacaaaa gtaca (SEQ ID NO: 182) | 70 |
| | acgctgtaagctcaataaactttaagctgtaaaataaacttaagct caataacaaaaatatgtaagctgttttagaaacaaaaa gc (SEQ ID NO: 80) | 85 | gtttcttaagctgtaaaata aactttaagctccaataacaa aagtaca (SEQ ID NO: 183) | 50 |
| | acgctgtaagctcaataaactttacgatgtaagctcattta cgatgtaagctcaaaaataacaaaaatatgtaagctgttt tagaaacaaaaaagc (SEQ ID NO: 73) | 99 | gtttcaataacttttacgatgt aagctcatttgtgcgaaaat aacaaaagtaca (SEQ ID NO: 176) | 55 |

TABLE 5-continued

Examples of DNA encoding of glycans.

| Structure | Long Nucleotide | Length | Short Nucleotide | Length |
|---|---|---|---|---|
| 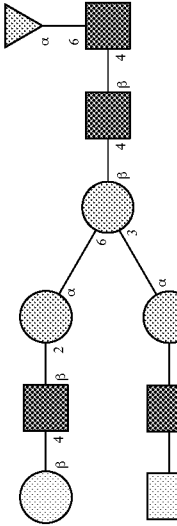 | acgctgtaagctcaaataaactttacgatgtaagtcaaat aacaaaaatatgtaagctgtttagaaacaaaaagc (SEQ ID NO: 74) | 79 | gtttcaataaactttacgatgt aagtcaaataacaaaagta ca (SEQ ID NO: 177) | 44 |
| 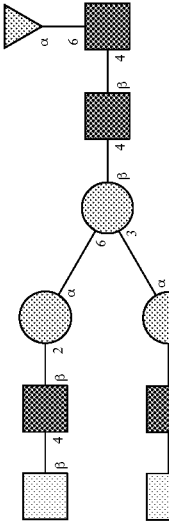 | acgctgtaagctcaaataaactttacgctgtaagtcaaat aacaaaaatatgtaagctgtttagaaacaaaaagc (SEQ ID NO: 81) | 79 | gtttcaataaactttacgctgt aagtcaaataacaaaagta ca (SEQ ID NO: 184) | 44 |
| 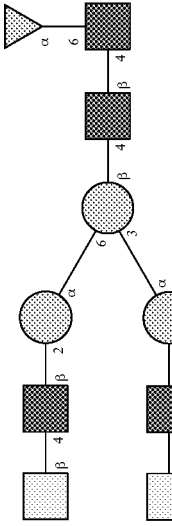 | acgctgtaagctcaaataaactttacgctgtaagtcaaat aacaaaaatatgtaagctgtttagaaacaaaaagc (SEQ ID NO: 81) | 79 | gtttcaataaactttacgctgt aagtcaaataacaaaagta ca (SEQ ID NO: 184) | 44 |
| 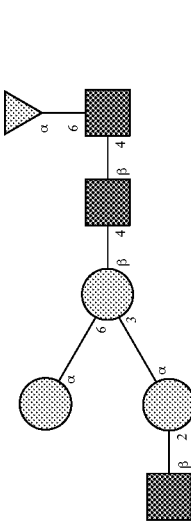 | agaaaacaagctcaaataaactttaataacaaaaatatgt aagctgtttagaaacaaaaagc (SEQ ID NO: 82) | 65 | gttgtaataaactttaataaca aagtaca (SEQ ID NO: 185) | 30 |

TABLE 5-continued

Examples of DNA encoding of glycans.

| Structure | Long Nucleotide | Length | Short Nucleotide | Length |
|---|---|---|---|---|
| | agaaaagacgatgtttagaaaacaaaagctcaaataaa ctttagaaaagacgatgtaagctgtttagaaacaaaatg taagctgttttagaaacaaaaagc (SEQ ID NO: 83) | 106 | gttggaataaactttgtgtcaa taacaaaagtaca (SEQ ID NO: 186) | 35 |
| | agaaaagacgatgtttagaaaacaaaagctcaaataaa ctttagaaaagacgatgtttagaaaacaaaagctcaaat aacaaaaatatgtaagctgttttagaaacaaaaagc (SEQ ID NO: 84) | 119 | gttggaataaactttagaaaa gacgatgttttagaaaacaaa aagctcaaataacaaaagta ca (SEQ ID NO: 187) | 64 |
| | agaaaagacgatgtttagaaaacaaaagctcaaataaa ctttaataaactttaataacaaaaataacaaaatatgta agctgtttagaaacaaaaagc (SEQ ID NO: 85) | 105 | gttggaataaactttaataaac tttaataacaaaataacaa aagtaca (SEQ ID NO: 188) | 50 |

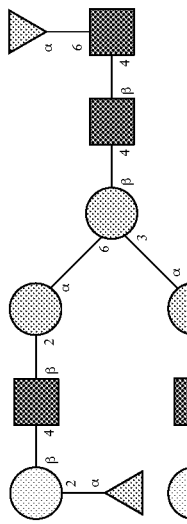
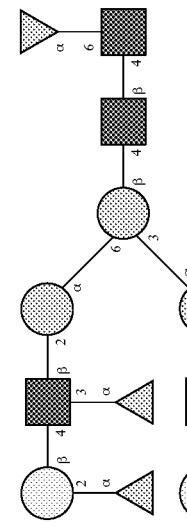
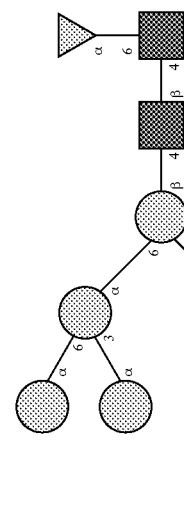
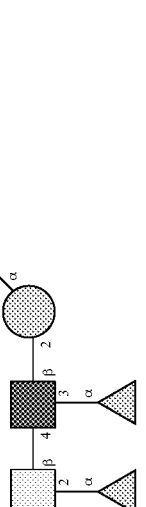

TABLE 5-continued

Examples of DNA encoding of glycans.

| Structure | Long Nucleotide | Length | Short Nucleotide | Length |
|---|---|---|---|---|
| | agaaaagacgatgtttagaaaacaaaagctcaaataaa ctttaatagccaataacaaaaatatgtaagctgttttagaa acaaaaagc (SEQ ID NO: 86) | 92 | gttggaataaactttaatagcc aataacaaagtaca (SEQ ID NO: 189) | 37 |
| | agaaaagacgatgtttagaaaacaaaagctcaaataaa ctttacgatgtttagaaaacaaaagctcaaataacaaaa aatatgtaagctgtttagaaaacaaaaagc (SEQ ID NO: 87) | 112 | gttggaataaacttacgatgt tttagaaaacaaaagctcaa ataacaaagtaca (SEQ ID NO: 190) | 57 |
| | agaaaagacgatgtttagaaaacaaaagctcatttagaa aagacgatgtttagaaaacaaaagctgtaaaataaact ttagaaaagacgatgtttagaaaacaaaagctcaaataa caaaaatatgtaagctgtttagaaaacaaaaagc (SEQ ID NO: 88) | 159 | gttggtttagaaaaggtgaga aaataaactttagaaaagac gatgttttagaaaacaaaaag ctcaataacaaaagtaca (SEQ ID NO: 191) | 82 |

TABLE 5-continued

Examples of DNA encoding of glycans.

| Structure | Long Nucleotide | Length | Short Nucleotide | Length |
|---|---|---|---|---|
| | agaaaagacgatgtaagctcaaataaactttagaaagac gatgtaagctcaaataacaaaaatatgtaagctgtttaga aacaaaaaagc (SEQ ID NO: 89) | 93 | gttgcaataaactttagaaaa gacgatgtaagctcaaataa caaagtaca (SEQ ID NO: 192) | 51 |
| | agaaaagacgatgtaagctcaaataaactttaatagccaat aacaaaaatatgtaagctgtttagaaacaaaaagc (SEQ ID NO: 90) | 79 | gttgcaataaactttaatagcc aataacaaagtaca (SEQ ID NO: 193) | 37 |
| | agaaaagacgatgtgtttagaaaacaaataaagctcaaataaa ctttaataacaaaaatatgtaagctgtttagaaaacaaaa agc (SEQ ID NO: 91) | 85 | gttggaataaactttaataaca aagtaca (SEQ ID NO: 194) | 30 |

TABLE 5-continued

Examples of DNA encoding of glycans.

| Structure | Long Nucleotide | Length | Short Nucleotide | Length |
|---|---|---|---|---|
| | agaaagacgatgtaagctcaaataaacttacgatgtaa gctcaaataacaaaaatatgtaagctgttttagaaacaaa aaagc (SEQ ID NO: 92) | 86 | gttgcaataaacttacgatgt aagctcaaataacaaaagta ca (SEQ ID NO: 195) | 44 |
| | aagctgttttacgatgtttagaaacaaataagctcaaataa acaaattacgatgtaagctcaaataacaaaaatatgtaa gctgttttagaaacaaaaaagc (SEQ ID NO: 93) | 105 | aagctgtttacgatgttttaga aacaaaaagctcaaataa caaattacgatgtaagctca aataacaaagtaca (SEQ ID NO: 196) | 79 |
| | aagctgttttacgatgtttagaaacaaataagctcaaataa acaaattacgatgtaagctcaaataacaaaaatatgtaa gctgttttagaaacaaaaaagc (SEQ ID NO: 93) | 105 | aagctgtttacgatgttttaga aacaaaaagctcaaataa caaattacgatgtaagctca aataacaaagtaca (SEQ ID NO: 196) | 79 |

TABLE 5-continued

Examples of DNA encoding of glycans.

| Structure | Long Nucleotide | Length | Short Nucleotide | Length |
|---|---|---|---|---|
| | aagctgttttacgatgtaagctgtaagctcaataacaaatttaataaactttaataacaaaaatatgtaagctgttttagaaacaaaaagc (SEQ ID NO: 94) | 98 | aagctgtttacgatgtaagctcaataacaaatttaataacttaataacaaaaataacaaagtaca (SEQ ID NO: 197) | 72 |
| | aagctgttttacgatgtaagctcaataacaaatttacgatgttttagaaacaaaagctcaataacaaaaagc (SEQ ID NO: 95) | 105 | aagctgtttacgatgtaagctcaataacaaatttacgatgttttagaaacaaaagctcaaataacaaagtaca (SEQ ID NO: 198) | 79 |
| | aagctgttttaggtaacacgatgtaagctcaataacaaatttaggtaacacgatgtaagctcaataacaaaaatatgtaagctgttttagaaacaaaaagc (SEQ ID NO: 96) | 106 | aagctgtttaggtaacacgatgtaagctcaataacaaatttaggtaacacgatgtaagctcaataacaaagtaca (SEQ ID NO: 199) | 80 |
| | aagctgttttaataacaaatttaagctcaataacaaaaaatatgtaagctgttttagaacaaacaaaaagc (SEQ ID NO: 97) | 71 | aagctgtttaataacaaatttaagctcaataacaaagtaca (SEQ ID NO: 200) | 45 |

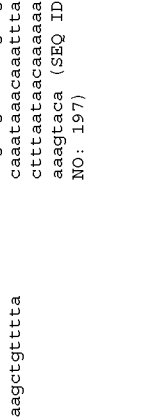
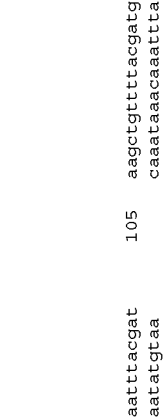
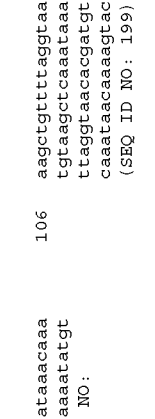
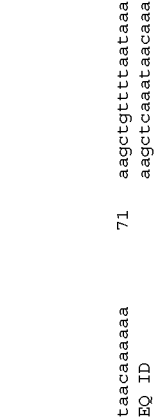

TABLE 5-continued

Examples of DNA encoding of glycans.

| Structure | Long Nucleotide | Length | Short Nucleotide | Length |
|---|---|---|---|---|
| | aagctgtttaataacaaatttaataacaaaaatatgtaa gctgttttagaaaacaaaaagc (SEQ ID NO: 98) | 64 | aagctgtttaataacaaattt aataacaaagtaca (SEQ ID NO: 201) | 38 |
| | aagctgtttaagctcaaataaacaaatttacgatgtttaga aacaaaaagctcaaataacaaaaatatgtaagctgtttt agaaacaaaaagc (SEQ ID NO: 99) | 98 | aagctgtttaagctcaaataa acaaatttacgatgtttagaa aacaaaagctcaaataaca aagtaca (SEQ ID NO: 202) | 72 |
| | aagctgtttacgctgtaagctcaaataacaaatttacgcc atttgtaagctcaaataacaaaaatatgtaagctgtttaga aacaaaaagc (SEQ ID NO: 100) | 96 | aagctgtttgttcaataaac aaatttacgccattgtaagct caataacaaaagtaca (SEQ ID NO: 203) | 61 |
| | aagctgtttaagctcaaataacaaatttaataacaaaaa tatgtaagctgtttagaaacaaaaagc (SEQ ID NO: 101) | 71 | aagctgtttaagctcaaataa acaaatttaataacaaagta ca (SEQ ID NO: 204) | 45 |

TABLE 5-continued

Examples of DNA encoding of glycans.

| Structure | Long Nucleotide | Length | Short Nucleotide | Length |
|---|---|---|---|---|
| | aagctcaaataaacttaagctcaaataacaaaaatatgt aagcttttagaaacaaaaagc (SEQ ID NO: 102) | 65 | aagctcaaataaacttaagc tcaaataacaaagtaca (SEQ ID NO: 205) | 39 |
| | aagctcaaataaacttaataaacaataacaaaaatatgta agctgtttagaaacaaaaagc (SEQ ID NO: 103) | 65 | aagctcaaataaacttaataa acaataacaaagtaca (SEQ ID NO: 206) | 39 |
| | aagcacaacgatgtaagctcaaataacttaagcacaac gatgtaagctcaaataacaaaaatatgtaagctgttttaga aacaaaaagc (SEQ ID NO: 104) | 93 | aagcacaacgatgtaagctc aaataacttaagcacaacg atgtaagctcaaataacaaaa gtaca (SEQ ID NO: 207) | 67 |
| | aagctcatttaagctgtaaaataaacttaagctcaaataa caaaaatatgtaagctgtttagaaacaaaaagc (SEQ ID NO: 105) | 78 | aagctcatttaagctgtaaaa ataaacttaagctcaaataac aaagtaca (SEQ ID NO: 208) | 52 |

TABLE 5-continued

Examples of DNA encoding of glycans.

| Structure | Long Nucleotide | Length | Short Nucleotide | Length |
|---|---|---|---|---|
| | aagctcatttaagctgtaaaataaacttaagctcattaagcttaaaaataacaaaaaatatgtaagctgttttagaaacaaaaaagc (SEQ ID NO: 106) | 91 | aagctcatttaagctgtaaaataaacttaagctcattaagcttaaaaataacaaaagtaca (SEQ ID NO: 209) | 65 |
| | aagctcaaataaacttacgaaacgatgtaagctcaataacaaaaaatatgtaagctgttttagaaacaaaagc (SEQ ID NO: 107) | 79 | aagctcaaaataaacttgtaccaataacaaagtaca (SEQ ID NO: 210) | 37 |
| | aagctcaaataaacttaataacaaaaaatatgtaagctgttttagaaacaaaaagc (SEQ ID NO: 108) | 58 | aagctcaaataaacttaataacaaagtaca (SEQ ID NO: 211) | 32 |
| | aagctcaaataaacttaataacaaaaaatatgtaagctgttttagaaacaaaaagc (SEQ ID NO: 108) | 58 | aagctcaaataaacttaataacaaagtaca (SEQ ID NO: 211) | 32 |

TABLE 5-continued

Examples of DNA encoding of glycans.

| Structure | Long Nucleotide | Length | Short Nucleotide | Length |
|---|---|---|---|---|
| S | aagctcaaataaacttacgccatttgtaagctcaaataaca aaaatatgtaagctgtttagaacaaaaaagc (SEQ ID NO: 109) | 76 | aagctcaaataaacttacgc catttgtaagctcaaataaca aagtaca (SEQ ID NO: 212) | 50 |
| | agaaaagacgatctaagctctacgatgtaaga (SEQ ID NO: 110) | 32 | | |
| | acgcaacttagaaagaaacgatctaagctctacgatgt aaga (SEQ ID NO: 111) | 45 | | |
| | acgaaacttagaaagaaacgatctaagctctacgatgt aaga (SEQ ID NO: 112) | 45 | | |
| | agaaagacgatctacgctctacgataacgatgtaaga (SEQ ID NO: 113) | 39 | | |
| | acgatctacgctctacgataacgatgtaaga (SEQ ID NO: 114) | 32 | | |
| | acgctctacgataacgatgtaaga (SEQ ID NO: 115) | 25 | | |

TABLE 5-continued
Examples of DNA encoding of glycans.
| Structure | Long Nucleotide | Length Short Nucleotide | Length |
|---|---|---|---|
| 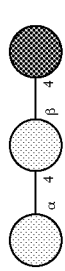 | acgaataacgatgtaagacccagtcaggcctaacgta (SEQ ID NO: 116) | 38 | |
|  | acgatgtaagacccagtcaggcctaacgta (SEQ ID NO: 117) | 31 | |
| 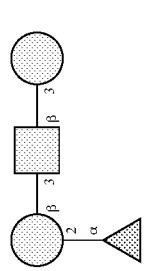 | agaaaagacgatctacgcttacga (SEQ ID NO: 118) | 25 | |
| 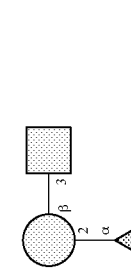 | agaaaagacgatctacgccccagtcaggcctaacgta (SEQ ID NO: 119) | 38 | |
|  | agaaaagacgacccagtcaggcctaacgta (SEQ ID NO: 120) | 31 | |

Glycan Codes to Functional Glycomics

Figure 14:
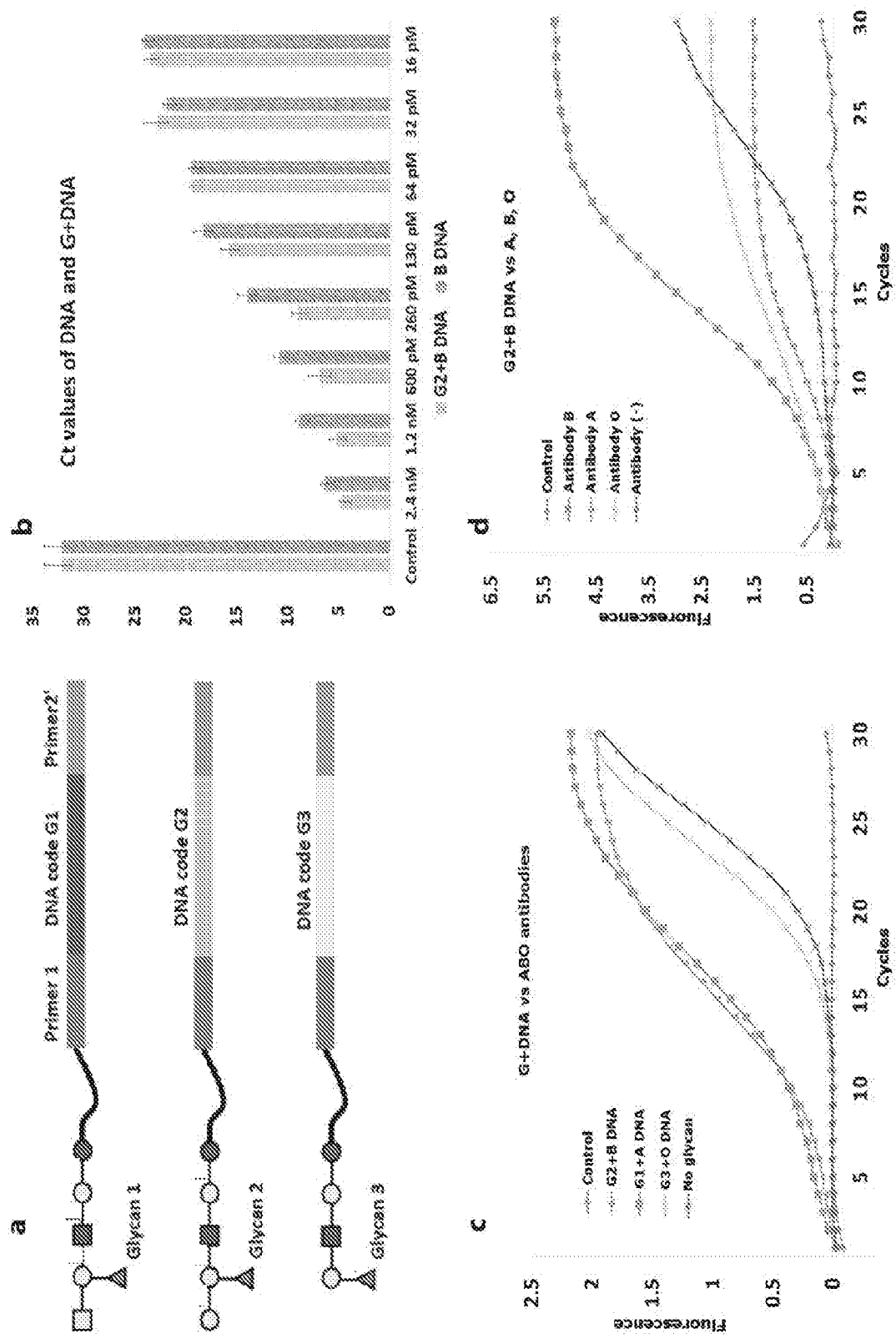
FIGS. 14a-d show DNA encoded blood glycans and their detection by qPCR.
Figure 15:
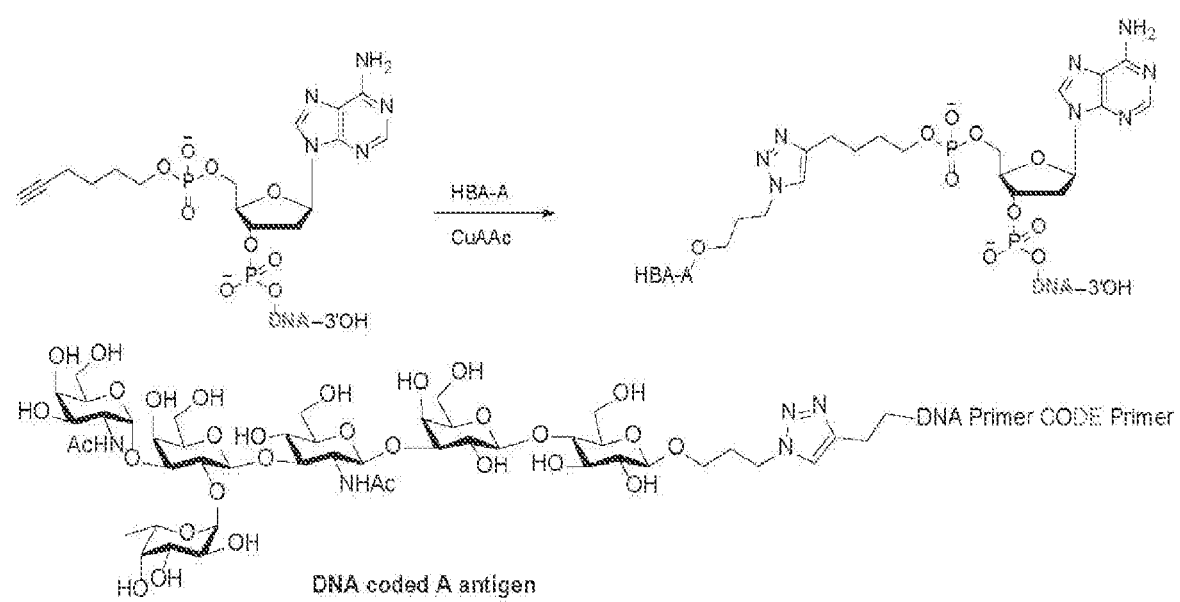
FIG. 15 shows an example of click conjugation of 5'-hexynyl DNA and azido modified glycans.

Once a reliable DNA code was established, we synthesized the blood group antigens A, B and O with an azide linker by adopting chemo-enzymatic strategies (synthesis details are provided in supporting information). These glycans then conjugated to the 5'-hexyne modified DNA codes corresponding to the antigens via click chemistry to get the glycan-DNA conjugates for the initial studies (FIG. 14a, FIG. 15). Blood group antigens were chosen because of two reasons, the abundant antibody presence, and any specificity and selectivity studies could be achieved easily with these structurally similar glycans.

Figure 16:
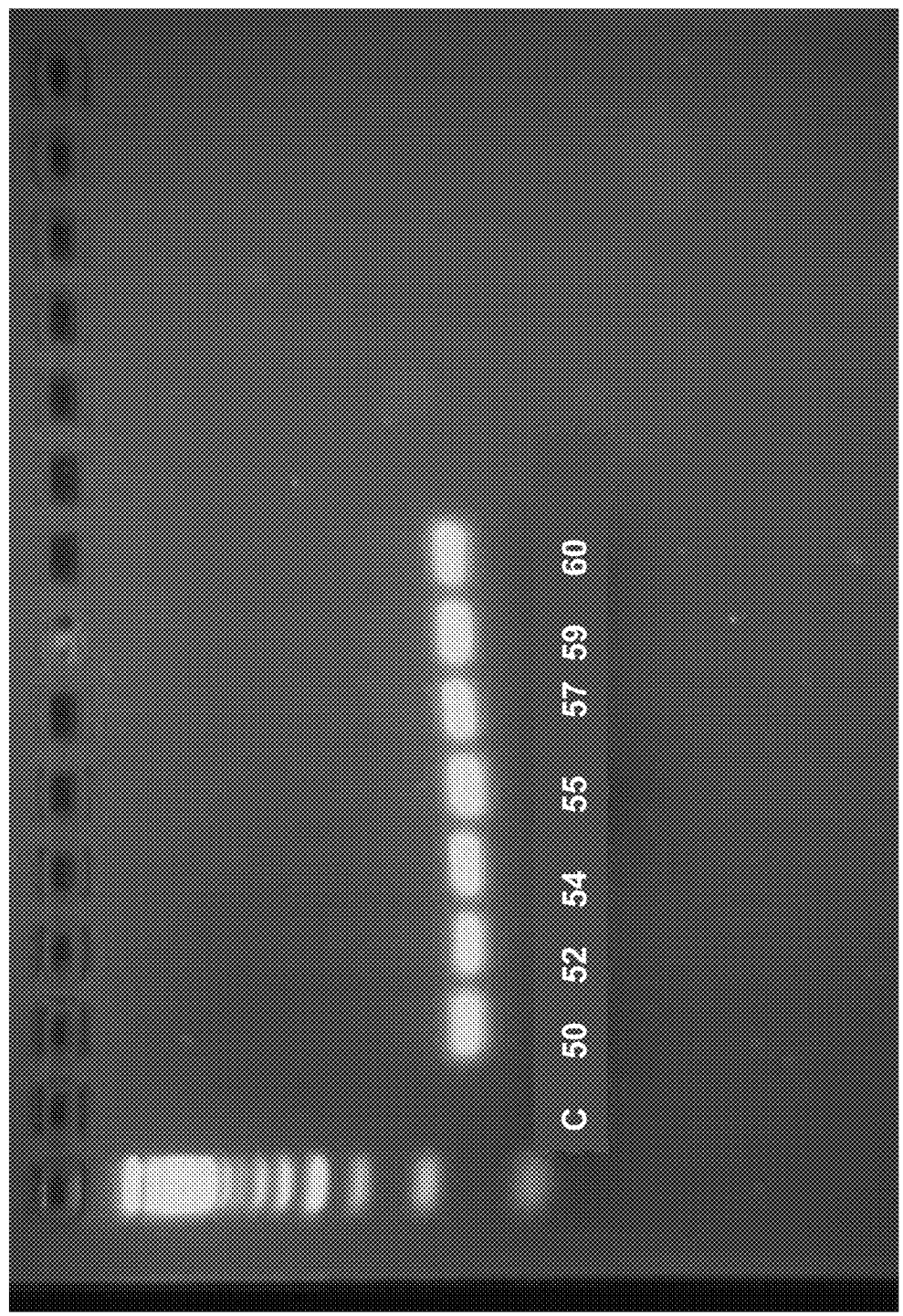
FIG. 16 shows a gradient PCR for Tm determination. Lanes are marked with the temperature gradient from 50° C. to 60° C.
Figure 18:
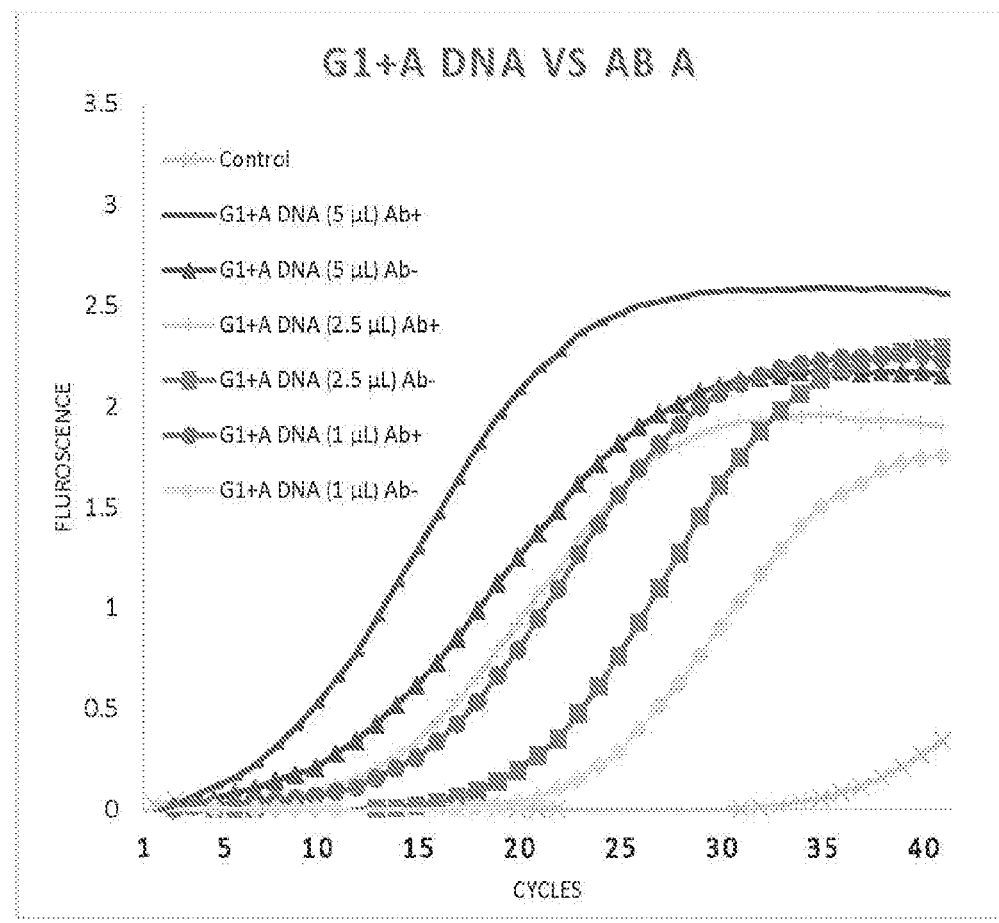
FIG. 18 shows use of G1+A DNA for the detection of A antibodies. 10 µL of three different concentration (5 µM, 2.5 µM and 1 µM) were incubated with 2 µL of Blood Group A Antigen Antibody RE-193 (MA1-19693).
Figure 19:
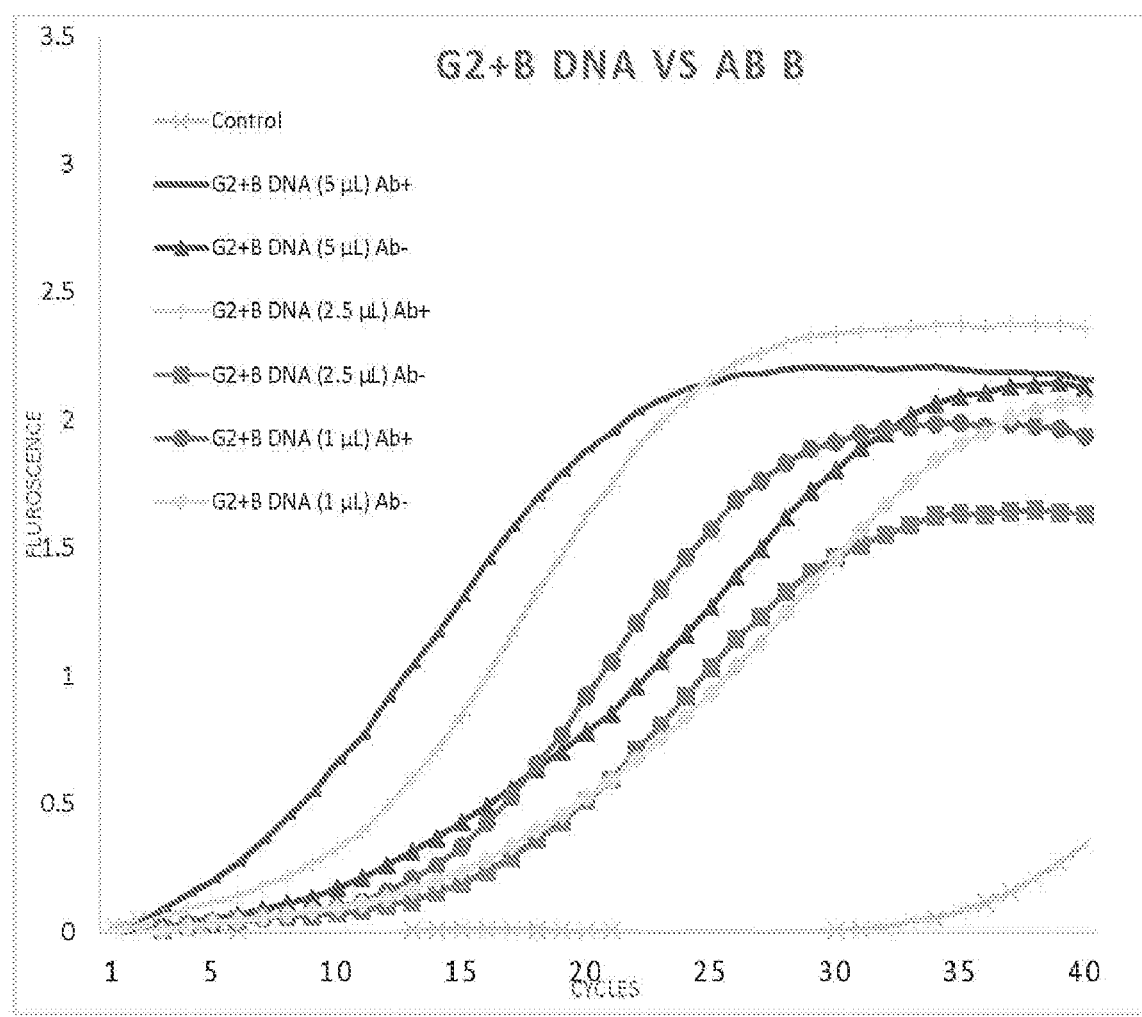
FIG. 19 shows use of G2+A DNA for the detection of B antibodies. 10 µL of three different concentration (5 µM, 2.5 µM and 1 µM) were incubated with 2 µL of Blood Group B Antigen Antibody HEB-29 (MA1-19691).
Figure 20:
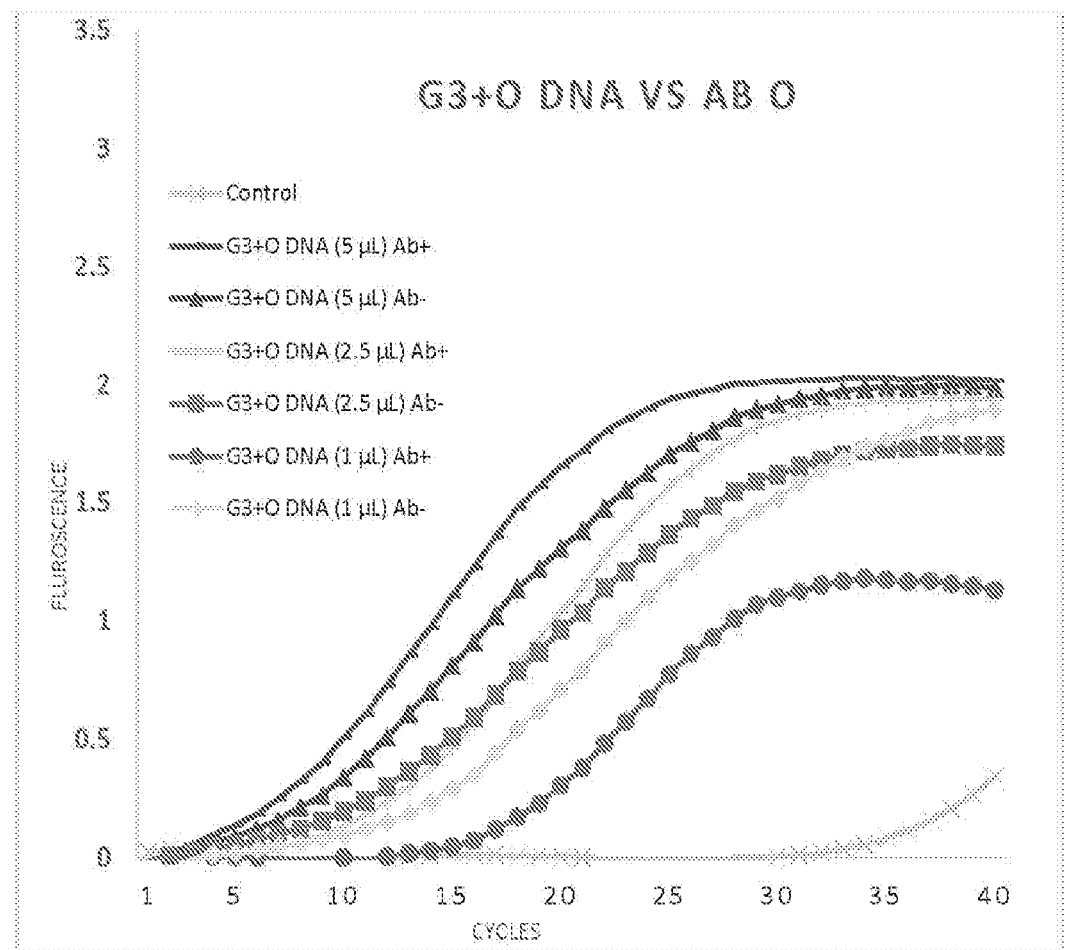
FIG. 20. G3+O DNA for the detection of O antibodies. 10 µL of three different concentration (5 µM, 2.5 µM and 1 µM) were incubated with 2 µL of Blood Group ABH Antigen Antibody RE-10 (MA1-19694).
Figure 21:
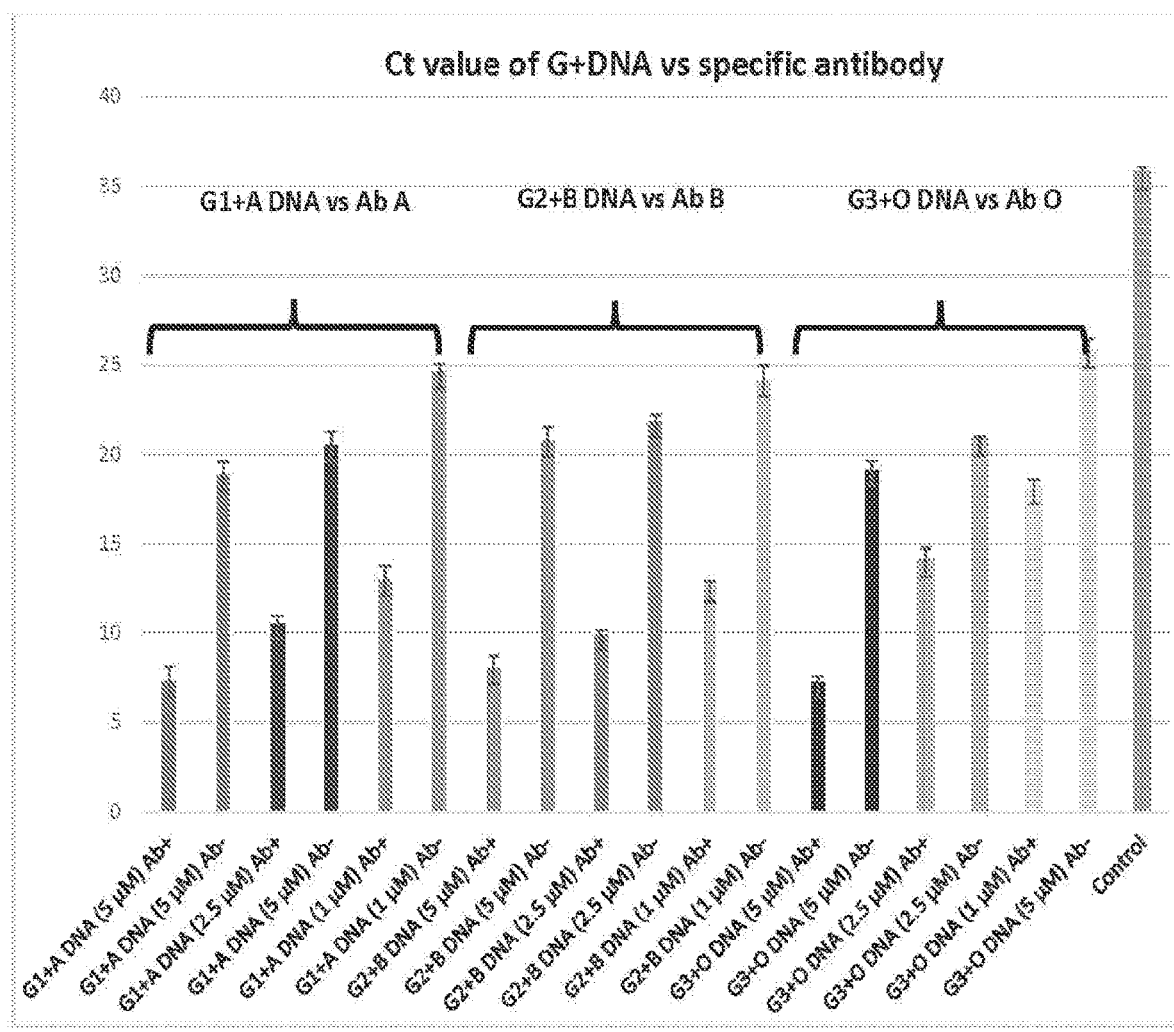
FIG. 21 shows the Ct value of different concentrations of G+DNA when incubated with the specific antibody, based on results shown in FIGS. 18-20.

The success of the DEGL lies in the utility of applying the DNA codes to the standard PCR and qPCR protocols. It is crucial to have the glycan-coupled DNA (G+DNA) achieve similar PCR efficiency to the native DNA, so we compared the G+DNA conjugates with the corresponding native DNA strands to verify the efficiency of amplification in both PCR and qPCR. PCR was performed on DNA and G+DNA templates using standard thermal cycles with varying annealing temperatures. Gel electrophoresis analysis implied both DNA and G+DNA amplified well in the range of 52-60° C. (FIG. 16). Next, we examined the qPCR detection limit of the G+DNA conjugates; both DNA and G+DNA conjugates were serially diluted to provide different concentrations of templates, with final concentrations ranging from 2.4 nM to 16 pM. Standard curve qPCR was carried out to obtain the corresponding critical threshold value (Ct), which is used to compare the concentration of the templates in the qPCR reaction mixture, with a low Ct indicating high template concentration. Ct values of the conjugates from 2.4 nM to 16 pM concentrations were observed in the range of 5-25, while the negative control (no template control, NTC) gave a Ct value above 30 (FIG. 14b). A standard plot of the Ct value vs log concentration of the DNA and G+DNA conjugate fit well within a linear relationship indicating the successful application of G+DNA for quantitative detection up to the pico molar level (FIG. 17).

Encouraged by the result suggesting the detection of glycans from even a picomolar level, we proceeded to the final goal, screening of glycans against glycan binding proteins. DEGs can be used either as a screening tool against the known concentration of proteins or a detection tool to identify glycan-binding molecules. We did two sets of experiments for validating these two aspects of DEGs; initially, we demonstrated the detection of specific glycan binding proteins by using the familiar blood glycan-antibody interactions. All three G+DNA conjugates (G1+A DNA, G2+B DNA, and G3+O DNA, where G1, G2 and G3 representing A, B, and O glycan antigens, respectively) were interrogated with the commercially-procured human blood antibodies (IgM). Concentrations of 5 µM, 2.5 µM, and 1 µM of the G+DNA were incubated with 2 µL of the antibodies; unbound DNA was eliminated either by filtration with 100 k cut off centrifuge tubes or precipitation with magnetic protein L beads. The filtrate/eluent obtained was then subjected to qPCR assay, and Ct values of the G+DNA then compared with the Ct values of negative control wherein antibody was omitted from the incubation. Ct difference of more than 10 points was observed at all three G+DNA concentrations (FIGS. 18-20 and FIG. 21), indicating the successful application of DNA encoding glycan in screening.

In another experiment, we evaluated the use of DNA encoding glycans in the detection of glycan-binding proteins, a mixture of all three antibodies (1:1:1) interrogated with each of the G+DNA conjugates (2.5 uM) separately. As seen in FIG. 14c, Ct values of 8.4 and 7.7 respectively for G1+A DNA and G2+B DNA infer the high affinity binding of A and B glycans with their corresponding antibodies Ab A and Ab B. But, a similarly tested G3+O DNA showed relatively higher Ct value but still less than that of the no antibody controls indicating weak interaction of antigens with the Ab O (FIG. 14c). This result implies that DNA encoding glycans are ideal for the selective detection even from a mixture of closely related target proteins. We also tested the specificity of the method. For this aim, we investigated a single G+DNA (G2+B DNA) against the three antibodies, and a clear amplification was visible only when both Ab B and G2+B DNA were in the mix. All the remaining tests were poorly amplified (FIG. 14d). This result proved that the amplification was indeed from the target specific binding of glycan, and there was no significant interference of nonspecific binding of DNA and target proteins.

Figure 22:
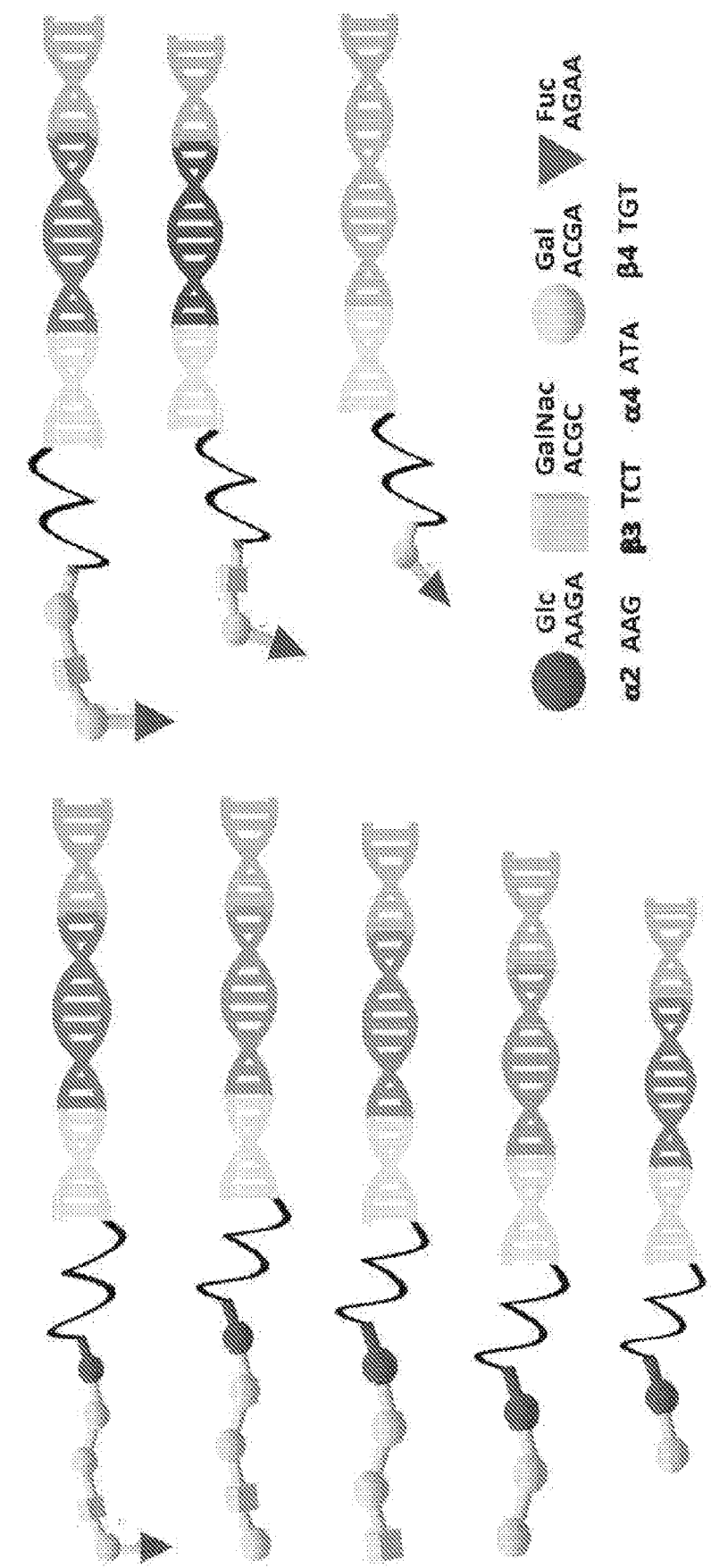
FIG. 22 shows Globo glycan structure and representation of globo-glycan conjugates.

DNA Encoded Glycan Library of Globo Series Glycans and Multiplex Analysis Using Next Generation Sequencing After successfully demonstrating blood antigen selection and amplification by PCR and qPCR, we wanted to apply the technology to the next generation sequencing platforms. We designed a DNA Encoded Glycan Library (DEGL) of globo series glycans (FIG. 22). Globo-glycans are characterized as glycosphingolipids, and their expression pattern is well correlated with cancer metastasis and progression. Certain Globo-series glycans are overexpressed in some cancers and proven as biomarkers for the early detection of breast cancer and ovarian cancer. [28-31] Recent developments in the Globo-H based immunotherapy also require highly sensitive methods to quantitatively detect the antiglobo H antibodies for monitoring therapy and in clinical trials. [32-34] Aberrant expression of immunogenic globo glycans triggers the production of the anti-glycan antibodies targeting these epitopes. These antibodies are generally observed in the sera even before cancer progresses to the late stages and effectively act as biomarkers for several types of cancer including breast, lung, prostate and ovarian cancer.[35-37] Globo-H and its truncated analogs Gb5, Gb4, Gb3, and Gb2 (FIG. 28) were synthesized from the enzymatic extension of chemically synthesized Gb-2. To test the terminal epitope specificity alone, Bb4, Bb3 and Bb2 were also synthesized via chemo-enzymatic strategy (Procedure is described in supporting info). All these glycans were then conjugated to the corresponding DNA codes via click chemistry.

Figure 23:
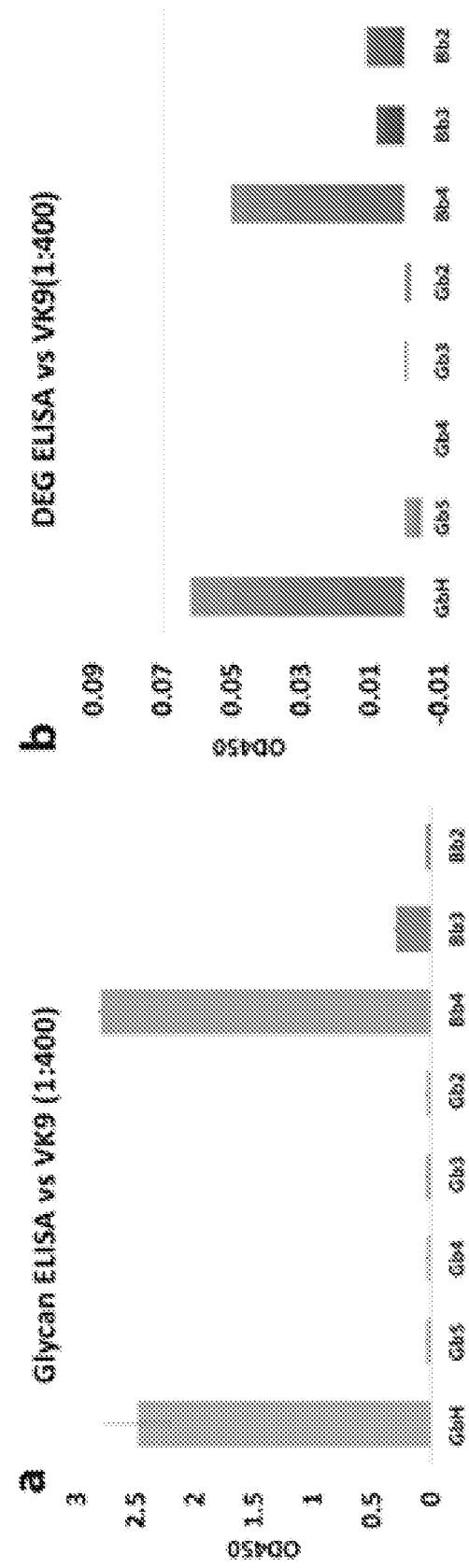
FIGS. 23a-b show ELISA detection of glycans and glycan-DNA conjugates.

ELISA of Globo Series Glycans and DNA Encoded Glycan Library of Globo Series Glycans Initially we validated the selected system with the conventional ELISA to confirm the antibody binding capacity and specificity of the glycans. Since sugars have low binding affinity for unmodified plastic surfaces, the binding protein, streptavidin, was used to capture biotinylated sugars. In another experiment we also tested DEGL using ELISA to see the effect of different presentation of glycans. For this assay, we coated the DEGL onto plastic surfaces directly. Both naked glycan and DEGL was tested against VK9, a mouse IgG anti-Globo H monoclonal antibody. In the ELISA of biotinylated sugars, VK9 has very high binding intensities to GbH and Bb4 and very low binding to Bb3 (FIG. 23a). However, DEGL ELISA also showed week binding for Bb2 along with the strong binding with GbH and Bb4 (FIG. 23b). This result bolstered our earlier observation; immobilized glycans on a surface may not provide accurate information of the binding especially when they are close to the solid surface. We rationalize this difference in pattern to the different presentation of glycan epitope, all of the four glycans have the same terminal epitope of Fuc a1-2 Gal(b1-3 GalNAc), which is recognized by VK9 antibodies, [38] but a long DNA tag on the DEGL will give more space to the glycan antigens binding with the antibody, while normal ELISA would block the binding of the short glycans of Bb3 and Bb2. This kind of interference will be further negligible when a DNA encoded glycan library is used, because the antigen-antibody interaction takes place in a more biologically significant solution phase.

Multiplex Detection GbH Antibody

Figure 24:
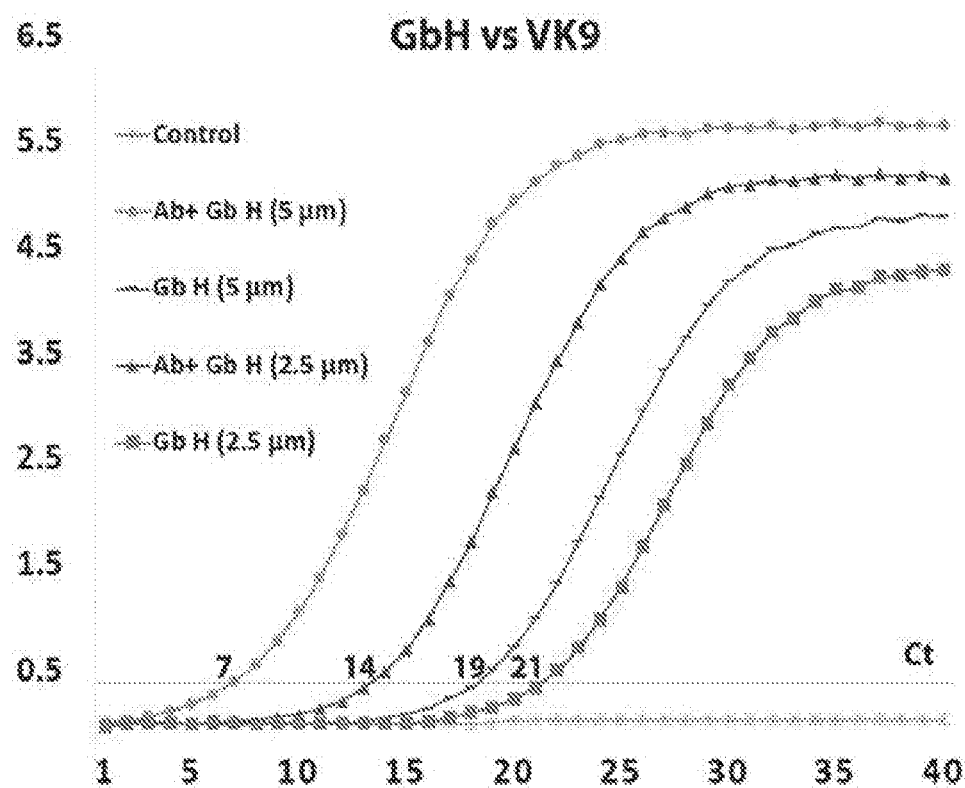
FIG. 24 shows qPCR detection GbH against VK9 antibody.

Seeing ELISA of DEGL and Glycan biotin against VK9 were consistent with the reported methods, [36] we tested the GbH+DNA with the monoclonal anti globo-H antibody VK9 using the protein A/G protocol, and the qPCR results for two different concentrations (2.5 µM and 5 µM of GbH+DNA incubated with 2 µL of VK9 antibody) are given in the FIG. 24. As expected, a concentration dependent binding was observed as indicated by the Ct values (7 and 19 for 5 µM and 14 and 21 for 2.5 µM).

Figure 25:
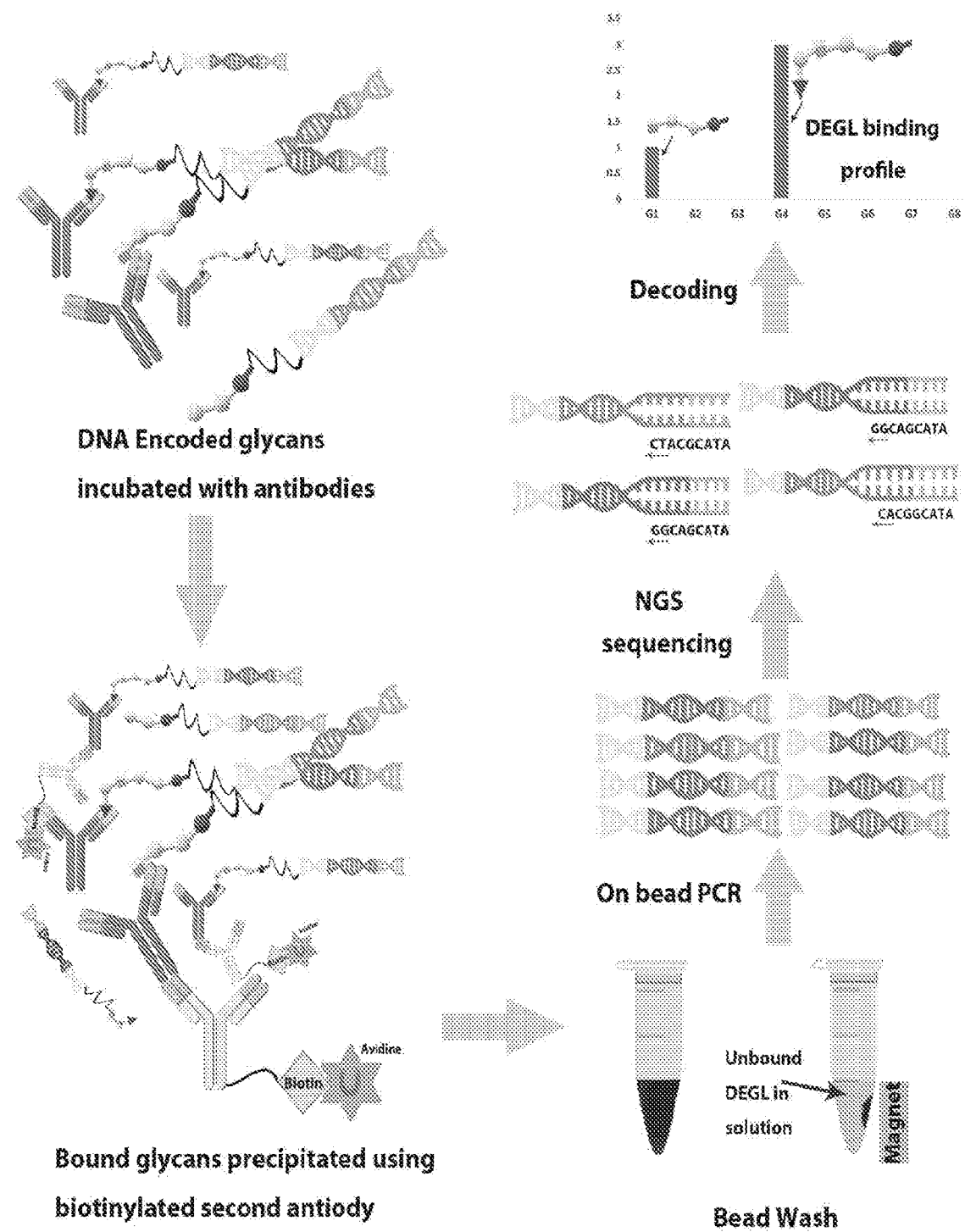
FIG. 25 shows a protocol for multiplex detection of glycan binding to a target.
Figure 26:
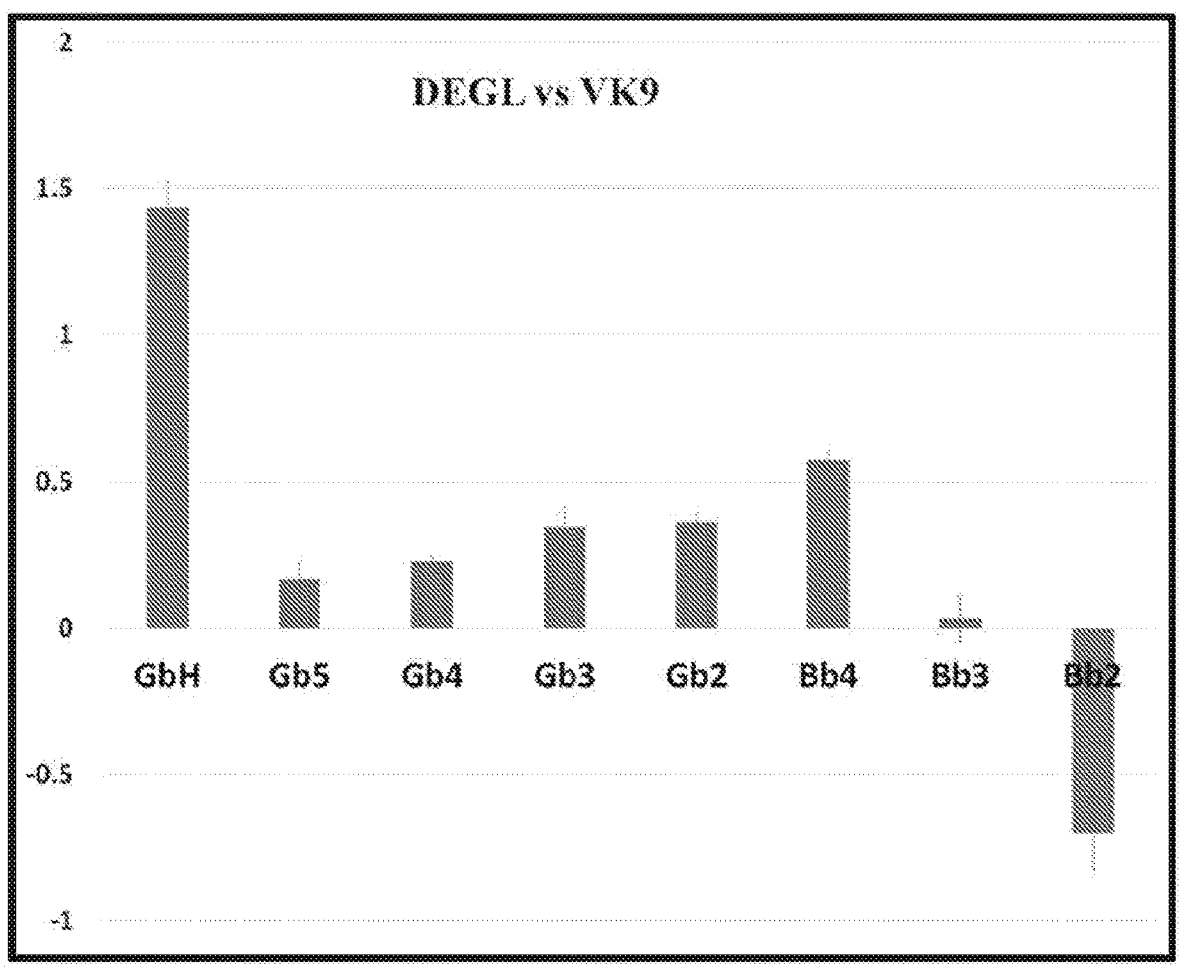
FIG. 26 shows multiplex detection of DEGL against VK9 antibody using a NGS method.

Next, we wanted to translate the results to more promising NGS based parallel screening. Initially we tested the different concentrations of DEGL with different concentrations of VK9 antibody using the PCR and qPCR assays. We incubated 1 uM, 500 nM, 100 nM and 10 nM samples with 0.5 µL, 1 µL, and 2 µL of the VK9 antibody (0.5 µg/µL), and unbound glycans were washed out after precipitating the bound glycan-VK9 complex on protein A/G beads. Each assay was compared to the same amount of DEGL with no VK9 negative control. Then, washed beads were used as the template for the NGS analysis. Briefly, beads were diluted to 20 µL, and from this, 2 µL was used for the initial PCR amplification (18 cycles). PCR products were then purified using AMpure beads (Beckman Coulter) according to the manufacturer's protocol and used for the NGS fusion PCR to incorporate the index codes and ion-torrent NGS adapters. Now about 150 bp DNA codes, it was again purified using AMpure beads, and all barcoded samples were run through an Agilent Bioanalyzer for quality control. Samples were then pooled in equimolar concentration and adjusted to the desired 26 pM for the NGS, analyzed using ion-PGM semiconductor sequencer. Data were analyzed using 'FASTAPTAMER' software,[39] and an in house developed program. Unfortunately, the sequencing results were not good enough to discriminate the antibody samples with the no antibody samples with poor signal to noise ratio. We assumed this could be due to the high sensitivity of the sequencing method, and even the smallest of nonspecific DNA binding to the protein A/G beads (Ct values from qPCR suggest minor nonspecific binding) was affecting the overall performance of the assay. Hence, we decided to not pursue this procedure again and instead used biotin tagged secondary antibody specific to VK9 for separation of bound to unbound DNA-glycan conjugates. After incubation, the complex of DEGL+VK9+anti-VK9-biotin was separated using the magnetic streptavidin beads and washed several times to remove any unbound DEGL from the mixture (FIG. 25). Downstream processing of beads was performed as described above, and we compared the relative enrichment of all the library members in comparison with the no VK9 negative control. As shown in FIG. 26, only Globo-H, the antigen specific to the monoclonal antibody VK9 and its truncated analog Bb4 is enriched compared to the rest of glycans indicating the efficiency of NGS method in detecting the glycans from a mixture. Even though the results were in line of our expectation, there was some random amplification in no serum controls, which we thought might influence the overall result since the enrichment is compared with the no serum control. We assumed this might be due to the nonspecific binding of DNA to any of the components in the selection procedure, for instance binding to the secondary antibody or magnetic beads. Single stranded DNAs has the tendency to form the secondary structure, which may be the cause for aptamers like binding. To minimize this, we then hybridized the DNA conjugated glycans with their complimentary strand ssDNA to get the dsDNA which forms the helix and generally void of any binding. Next, dsDNA glycan library was incubated against the VK9 and selection and sequencing was done according to the same procedure. Yet, the random amplification in the negative control was not eliminated completely. This left with the only remaining possibility, which is a PCR induced noncompetitive amplification, means a certain DNA is amplified from the extremely low concentration of DNA templates. This was further confirmed when different sequencing run gave different DNA sequences as the dominant sequence in the negative control. To solve this, we added a control sequence immediately after the selection to all the samples, which will act both as an internal standard and a supplemented template in negative control. With this modified method we further carried out the selection and sequencing of Globo-H series+A and B glycan DEGL against the VK9 antibody. The results shown in the figure clearly indicate the selective enrichment of GbH glycan along with the BB4 glycan in a lesser extent.

To demonstrate the feasibility of detecting naturally occurring antiglycan antibodies via NGS method, we selected the 10-glycan library against various blood groups. Serum of different blood groups A, B, O and AB were used in the selection.

Conclusion and Perspectives

Comparing the methods available to study the functions of glycans are not easy, they are largely dependent on assay platform, glycans and GBPs used in the assays and several other parameters like glycan presentation, incubation time, buffers and wash time etc.[11] Even the variability is significant in same platform technology, as of the glycan arrays from different group with different fabrication and assay protocol.[40] Our findings with the DEGL involving PCR, qPCR and NGS were positively correlated with the existing methods in selectivity, specificity and sensitivity to certain extent. A notable feature with the DEGL is its high throughput and high capacity in sample handling. Moreover, unlike the ELISA, Glycan array or MGBA which are monodimensional and read the optical density or florescence of the dye conjugated secondary antibody for the glycan detection, DEGL is multi-dimensional in glycan detection. DNA encoding brings tremendous possibility in detection and selection procedures as evidenced by the diverse methods opted by various research groups for the selection of small molecules.[41] Apart from the simple PCR, qPCR and NGS approaches, many groups have developed technologies that can detect binders specifically for each proteins from a mixture of targets or even from the cell lysates.[42, 43] Billions and trillions of compounds are screened against target proteins for drug development, hence the number of glycans in the DEGL is virtually unlimited.[17] On another side, with the proper selections of barcoding and sequencing platforms it is possible to screen samples from more than 750 assays in a single run. Also, fabrication of DEGL is simple chemical reaction widely used by chemist and biologists and very flexible to incorporate the multivalent presentation of glycans, which may be critical for many weak or medium binding glycans. One drawback of the assay is the time taken from the incubation to the sequencing result;

it requires a full day of preparation before placing the sample for sequencing, which take almost five hours for the delivery of data. All together the DEGL screening take about two days to complete. However, we think our glycan specific coding based on the structure could facilitate the use of multiplex qPCR using several probes for the diagnostic and vaccine monitoring. Even with the two days of turnaround, the method is quite suited for the GBP or antiglycan antibody profiling because of the efficiency, simultaneous parallel screening can provide all the results required in this stipulated time.

Advancement of the technologies in DNA synthesis and sequencing has extended the scope of DNA beyond genetics. For example, DNA encoded libraries of small molecules in drug screening and lead optimization is a priority of research in major pharmaceutical companies. We recognized the importance of applying DEL technologies to functional glycomics, because this field is otherwise restricted by low sensitivity detection techniques and extreme difficulty in obtaining samples. Applying the highly sensitive PCR detection will enhance the reach of functional glycomics to sub-nanogram samples and allow tandem high throughput screening. For the encoding purpose, we described here a unique method to code each glycan, analogous to the codons of protein synthesis, which accounted for extensive structural information. The program which is available (131.96.145.142:8000/cgi-bin/form.py) for the use of the research community is aimed at providing a uniformity in the codes for every single glycan in future DEGL applications. A structure specific code also helps researchers to develop target specific qPCR probe to analyze the binding of specific glycan or a group of glycans having the same structural motifs without requiring a NGS. We also elaborated methods for the DNA-Glycan conjugation and various selection protocols and information retrieval. Finally, as a proof of principle application study, we synthesized DEGL consisting of the globo series glycans and demonstrated their application in detecting the antiglycan antibodies.

REFERENCES

1. Chevolot, Y., et al., DNA-based carbohydrate biochips: a platform for surface glyco-engineering. Angew Chem Int Ed Engl, 2007. 46(14): p. 2398-402.
2. Fernandez-Tejada, A., F. J. Canada, and J. Jimenez-Barbero, Recent Developments in Synthetic Carbohydrate-Based Diagnostics, Vaccines, and Therapeutics. Chemistry, 2015. 21(30): p. 10616-28.
3. Wang, D., et al., Carbohydrate microarrays for the recognition of cross-reactive molecular markers of microbes and host cells. Nature biotechnology, 2002. 20(3): p. 275-281.
4. Horlacher, T. and P. H. Seeberger, Carbohydrate arrays as tools for research and diagnostics. Chem Soc Rev, 2008. 37(7): p. 1414-22.
5. Hahm, H. S., et al., Automated glycan assembly using the Glyconeer 2.1 synthesizer. Proceedings of the National Academy of Sciences, 2017. 114(17): p. E3385-E3389.
6. Seeberger, P. H., The logic of automated glycan assembly. Accounts of chemical research, 2015. 48(5): p. 1450-1463.
7. Xiao, Z., et al., Chemoenzymatic synthesis of a library of human milk oligosaccharides. The Journal of organic chemistry, 2016. 81(14): p. 5851-5865.
8. Wong, C.-H., Chemoenzymatic Synthesis of Glycans: Overview. Glycoscience: Biology and Medicine, 2015: p. 293-294.
9. Song, X., et al., Glycan microarrays of fluorescently-tagged natural glycans. Glycoconjugate journal, 2015. 32(7): p. 465-473.
10. Pochechueva, T., et al., Multiplex suspension array for human anti-carbohydrate antibody profiling. Analyst, 2011. 136(3): p. 560-569.
11. Pochechueva, T., et al., Comparison of printed glycan array, suspension array and ELISA in the detection of human anti-glycan antibodies. Glycoconj J, 2011. 28(8-9): p. 507-17.
12. Purohit, S., et al., Multiplex glycan bead array for high throughput and high content analyses of glycan binding proteins. Nature Communications, 2018. 9.
13. Brenner, S. and R. A. Lerner, Encoded combinatorial chemistry. Proceedings of the National Academy of Sciences, 1992. 89(12): p. 5381-5383.
14. Litovchick, A., et al., Encoded Library Synthesis Using Chemical Ligation and the Discovery of sEH Inhibitors from a 334-Million Member Library. Sci Rep, 2015. 5: p. 10916.
15. Kleiner, R. E., C. E. Dumelin, and D. R. Liu, Small-molecule discovery from DNA-encoded chemical libraries. Chemical Society Reviews, 2011. 40(12): p. 5707.
16. Lerner, R. A. and S. Brenner, DNA-Encoded Compound Libraries as Open Source: A Powerful Pathway to New Drugs. Angewandte Chemie International Edition, 2017. 56(5): p. 1164-1165.
17. Goodnow, R. A., C. E. Dumelin, and A. D. Keefe, DNA-encoded chemistry: enabling the deeper sampling of chemical space. Nature Reviews Drug Discovery, 2017. 16(2): p. 131-147.
18. Kwon, S. J., et al., Signal Amplification by Glyco-qPCR for Ultrasensitive Detection of Carbohydrates: Applications in Glycobiology. Angewandte Chemie-International Edition, 2012. 51(47): p. 11800-11804.
19. Kwon, S. J., et al., High sensitivity detection of active botulinum neurotoxin by glyco-quantitative polymerase chain-reaction. Anal Chem, 2014. 86(5): p. 2279-84.
20. Thomas, B., et al., Application of Biocatalysis to on-DNA Carbohydrate Library Synthesis. Chembiochem, 2017. 18(9): p. 858-863.
21. Aoki-Kinoshita, K., et al., GlyTouCan 1.0—The international glycan structure repository. Nucleic acids research, 2015. 44(D1): p. D1237-D1242.
22. Shinmachi, D., et al., Using GlyTouCan Version 1.0: The First International Glycan Structure Repository, in A Practical Guide to Using Glycomics Databases. 2017, Springer. p. 41-73.
23. Song, X., et al., Chemistry of natural glycan microarrays. Current opinion in chemical biology, 2014. 18: p. 70-77.
24. Kornfeld, S., E. Li, and I. Tabas, The synthesis of complex-type oligosaccharides. II. Characterization of the processing intermediates in the synthesis of the complex oligosaccharide units of the vesicular stomatitis virus G protein. Journal of Biological Chemistry, 1978. 253(21): p. 7771-7778.
25. D-glucan, A., Polysaccharide nomenclature. Eur. J. Biochem, 1982. 126: p. 439-441.
26. Harvey, D. J., et al., Symbol nomenclature for representing glycan structures: Extension to cover different carbohydrate types. Proteomics, 2011. 11(22): p. 4291-4295.
27. Varki, A., et al., Symbol nomenclature for glycan representation. Proteomics, 2009. 9(24): p. 5398-5399.
28. Huang, C. Y., et al., Carbohydrate microarray for profiling the antibodies interacting with Globo H tumor antigen. Proc Natl Acad Sci USA, 2006. 103(1): p. 15-20.

29. Wu, K., et al., Electrophoretic deposition of poly [3-(3-N, N-diethylaminopropoxy) thiophene] and composite films. Materials Chemistry and Physics, 2011. 125(1): p. 210-218.
30. Cheng, S. P., et al., Aberrant expression of tumor-associated carbohydrate antigen Globo H in thyroid carcinoma. J Surg Oncol, 2016. 114(7): p. 853-858.
31. Liao, S. F., et al., Immunization of fucose-containing polysaccharides from Reishi mushroom induces antibodies to tumor-associated Globo H-series epitopes. Proc Natl Acad Sci USA, 2013. 110(34): p. 13809-14.
32. Danishefsky, S. J., et al., Development of Globo-H Cancer Vaccine. Accounts of Chemical Research, 2015. 48(3): p. 643-652.
33. Zhou, Z., et al., A Fully Synthetic Self-Adjuvanting Globo H-Based Vaccine Elicited Strong T Cell-Mediated Antitumor Immunity. Chem Sci, 2015. 6(12): p. 7112-7121.
34. O'Cearbhaill, R. E., et al., A Phase I Study of Unimolecular Pentavalent (Globo-H-GM2-sTn-TF-Tn) Immunization of Patients with Epithelial Ovarian, Fallopian Tube, or Peritoneal Cancer in First Remission. Cancers (Basel), 2016. 8(4).
35. Chang, W. W., et al., Expression of Globo H and SSEA3 in breast cancer stem cells and the involvement of fucosyl transferases 1 and 2 in Globo H synthesis. Proc Natl Acad Sci USA, 2008. 105(33): p. 11667-72.
36. Wang, C. C., et al., Glycan microarray of Globo H and related structures for quantitative analysis of breast cancer. Proc Natl Acad Sci USA, 2008. 105(33): p. 11661-6.
37. Pochechueva, T., et al., Naturally occurring anti-glycan antibodies binding to Globo H-expressing cells identify ovarian cancer patients. Journal of Ovarian Research, 2017. 10.
38. Kudryashov, V., et al., Characterization of a mouse monoclonal IgG3 antibody to the tumor-associated globo H structure produced by immunization with a synthetic glycoconjugate. Glycoconj J, 1998. 15(3): p. 243-9.
39. Alam, K. K., J. L. Chang, and D. H. Burke, FASTAptamer: A Bioinformatic Toolkit for High-throughput Sequence Analysis of Combinatorial Selections. Mol Ther Nucleic Acids, 2015. 4: p. e230.
40. Wang, L., et al., Cross-platform comparison of glycan microarray formats. Glycobiology, 2014. 24(6): p. 507-517.
41. Chan, A. I., L. M. McGregor, and D. R. Liu, Novel selection methods for DNA-encoded chemical libraries. Current opinion in chemical biology, 2015. 26: p. 55-61.
42. McGregor, L. M., T. Jain, and D. R. Liu, Identification of ligand-target pairs from combined libraries of small molecules and unpurified protein targets in cell lysates. J Am Chem Soc, 2014. 136(8): p. 3264-70.
43. Li, G., et al., Photoaffinity labeling of small-molecule-binding proteins by DNA-templated chemistry. Angew Chem Int Ed Engl, 2013. 52(36): p. 9544-9.

Materials and Methods

All chemicals and biological reagents were purchased from Thermo Fisher Scientific™ unless otherwise mentioned. Maxima SYBR™ Green/ROX qPCR Master Mix, Platinum Pfx DNA Polymerase were purchased from Life Technologies (Carlsbad, CA). Micro Bio-Gel™ P-30 Chromatography Columns were purchased from Bio-Rad™ (Hercules, CA). Tris[(1-Benzyl-1H-1,2,3-Triazol-4-yl)methyl]amine (TBTA) Click chemistry Ligand were purchased from TCI (Tokyo, Japan). MicroAmp 96 well Fast PCR Reaction Plate, MicroAmp Optical Adhesive Film, MicroAmp™ Fast Reaction Tubes, Strips were purchased from Applied Biosystems™ (Foster City, CA). All oligonucleotides were purchased from Integrated DNA Technologies (Coralville, IA). UDP-GlcNAc, UDP-GalNAc, UDP-Gal, and GDP-Fucose were prepared using one-pot multienzyme system as reported previously.[1,2] β1-3-N-acetylglucosaminyltransferase (LgtA) and β1-4-galactosyltransferase (LgtB) from Neisseria meningitides were prepared as reported previously. [3, 4] β1-3-N-acetylglucosaminyltransferase (LgtD) and α1-4-galactosyltransferase (LgtC) were prepared as reported previously.[5] α1,2-FucT (HmFucT) from Helicobacter mustelae[6] was cloned into pET-28a vector and expressed in E. coli BL21 (DE3). α1-3-N-acetylgalactosaminyltransferase (GTA) and α1-3-galactosyltransferase (GTB) from human[7] were cloned into pET-28a vector and expressed in E. coli BL21 (DE3). The purified proteins were concentrated and desalted with 10 kDa molecular weight cut-off (MilliporeSigma™, MWCO) spin filters for further use. GloboH-related oligosaccharides were prepared by following the previous protocol with minor changes. [8] Primary antibodies used was mouse anti-Globo H monoclonal antibody VK-9 (IgG; eBioscience™, Catalog #:14-9700-82). The secondary antibodies used were Biotin-conjugated Goat anti-mouse IgG(H+L) and HRP-conjugated goat anti-mouse IgG(H+L) (Thermo Fisher Scientific™, Catalog #:A16066). Beads used were streptavidin conjugated magnetic beads (Dynabeads™ MyOne™ Streptavidin T1, Invitrogen™, Catalog #:65601), Pierce Protein A/G Magnetic Beads (Thermo Fisher Scientific™, Catalog #:88803), and Agencort AMPure Beads (Beckman Coulter Life Sciences™). Taq DNA polymerase, NHS-PEG4-Biotin and Pierce DNA Coating Solution were all purchased from Thermo Fisher Scientific™.

TABLE 6

DNA codes used in the study

| Name | 5'Mod | Sequence | 3'Mod |
|---|---|---|---|
| Oligo O | 5'Hexynyl | AATGATACGGCGACCACCGAAGAAAAGACGATCTAAGCTCTACGATGTAAGA*CACGTCTGAACTCCAGTCAC* (SEQ ID NO: 213) | None |
| Oligo A | 5'Hexynyl | AATGATACGGCGACCACCGAACGCAACTTTAGAAAAGAAAACGATCTAAGATCTACGATGTAA*CACGTCTGAACTCCAGTCAC* (SEQ ID NO: 214) | None |
| Oligo B | 5'Hexynyl | AATGATACGGCGACCACCGAACGAAACTTTAGAAAAGAAAACGATCTAAGCTCTACGATGTAAGA*CACGTCTGAACTCCAGTCAC* (SEQ ID NO: 215) | None |
| Gb-H | 5'Hexynyl | AATGATACGGCGACCACCGAAAGAAAAGACGATCTACGCTCTACGAATAACGATGTAAGA*CACGTCTGAACTCCAGTCAC* (SEQ ID NO: 216) | None |

TABLE 6-continued

DNA codes used in the study

| Name | 5'Mod | Sequence | 3'Mod |
|---|---|---|---|
| Gb-5 | 5'Hexynyl | AATGATACGGCGACCACCGAAACGATCTACGCTCTACGAATAACGA TGTAAGA*CACGTCTGAACTCCAGTCAC* (SEQ ID NO: 217) | None |
| Gb-4 | 5'Hexynyl | AATGATACGGCGACCACCGAAACGCTCTACGAATAACGATGTAAGA*C ACGTCTGAACTCCAGTCAC* (SEQ ID NO: 218) | None |
| Gb-3 | 5'Hexynyl | AATGATACGGCGACCACCGAAACGAATAACGATGTAAGACCCCAGT CAGGCCTAACGTA*CACGTCTGAACTCCAGTCAC* (SEQ ID NO: 219) | None |
| Gb-2 | 5'Hexynyl | AATGATACGGCGACCACCGAAACGATGTAAGACCCCAGTCAGGCCT AACGTA*CACGTCTGAACTCCAGTCAC* (SEQ ID NO: 220) | None |
| Bb-4 | 5'Hexynyl | AATGATACGGCGACCACCGAAAGAAAAGACGATCTACGCTCTACGA *CACGTCTGAACTCCAGTCAC* (SEQ ID NO: 221) | None |
| Bb-3 | 5'Hexynyl | AATGATACGGCGACCACCGAAAGAAAAGACGATCTACGCCCCCAGT CAGGCCTAACGTA*CACGTCTGAACTCCAGTCAC* (SEQ ID NO: 222) | None |
| Bb-2 | 5'Hexynyl | AATGATACGGCGACCACCGAAAGAAAAGACGACCCCAGTCAGGCCT AACGTA*CACGTCTGAACTCCAGTCAC* (SEQ ID NO: 223) | None |
| FW Primer | None | AATGATACGGCGACCACCGAA (SEQ ID NO: 224) | None |
| RV Primer | None | *GTGACTGGAGTTCAGACGTG* (SEQ ID NO: 225) | None |

*For all 5' to 3' DNA Sequences BOLD is the forward primer and BOLD ITALIC is the reverse primer binding site.

Preparative Scale Synthesis of Blood Antigen ABO and Globo Series Glycans

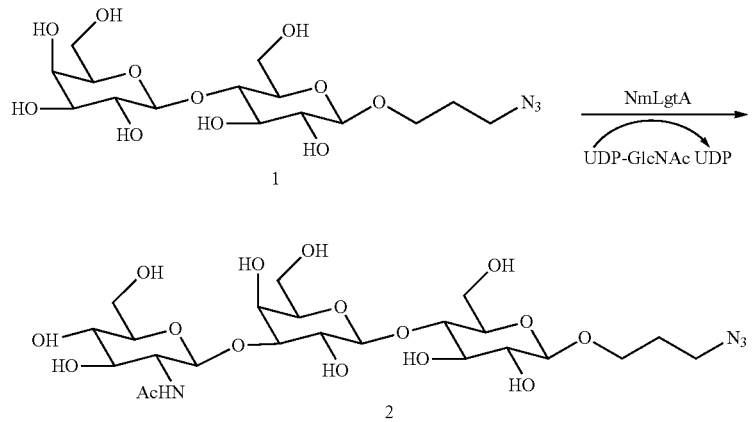

2 was prepared from 1 using LgtA from *Neisseria meningitides*. In detail, a reaction mixture in a final volume of 50 ml containing 50 mM of Tris-HCl, 425 mg of 1 (1 mmol), 607 mg of UDP-GlcNAc (1 mmol), 5 mM of $Mg^{2+}$, 8 mg of LgtA was carefully shaken at 37° C. to allow the formation of 2. The reaction was monitored by TLC (EtOAc/MeOH/ H2O/HOAc=5:2:1.4:0.4). Once the reaction was no longer move forward, equal volume ethanol was added to remove proteins and the solution was concentrated in vacuo. After purification using Bio-Gel™ P-2 column. 530 mg of 2 was obtained in 85% yield regarding 1.

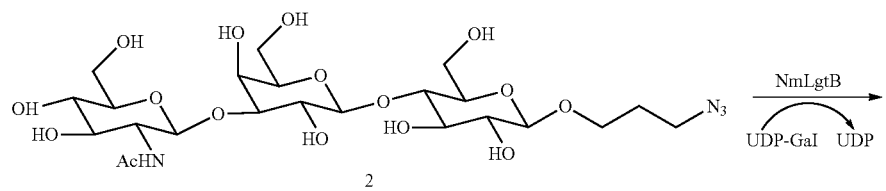

-continued

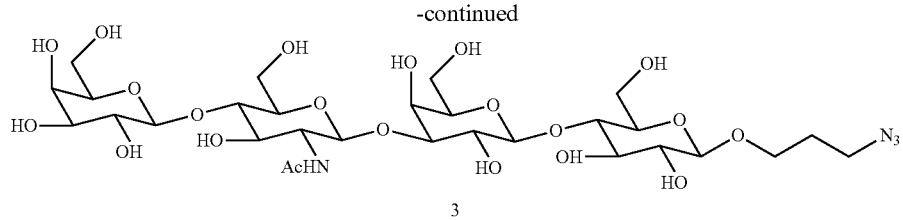

3

3 was prepared from 2 using LgB from *Neisseria meningitides*. In detail, 503 mg of 2 was dissolved in a 80 ml of reaction mixture containing 50 mM Tris-HCl, 12 mm of UDP-Gal, 5 mM of $Mg^{2+}$, 10 mg of LgB. The reaction was carefully shaken at 37° C. for overnight to allow the formation of 3. The reaction was monitored by TLC (EtOAc/MeOH/H2O/HOAc=5:2:1.4:0.4). Once reaction finished, equal volume ethanol was added to precipitate proteins and the supernatant was concentrated in vacuo. After purification by using Bio-Gel™ P-2 column. 432 mg of 3 was obtained in 76% yield regarding 2.

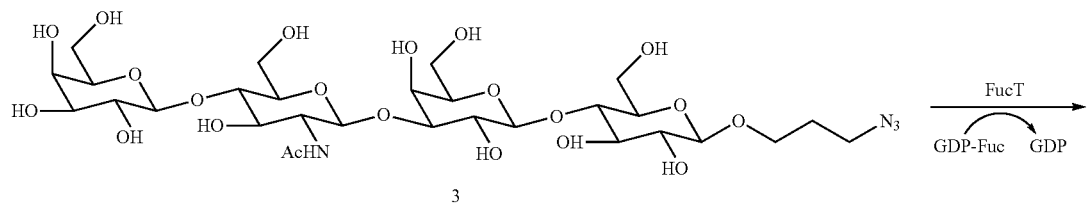

3

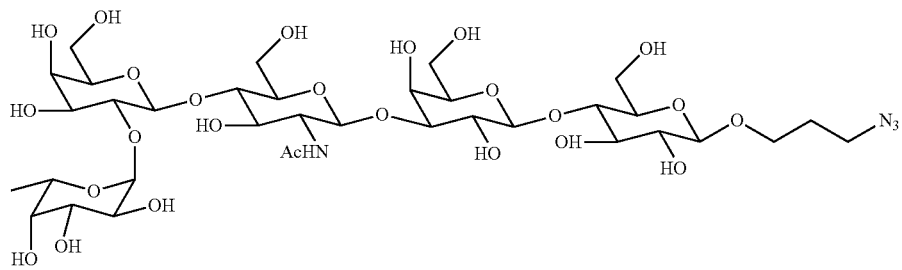

4

4 (blood O-antigen) was prepared 3 using FucT from *Helicobacter mustelae*. In detail, reaction was performed in a final volume of 35 ml mixture containing 50 mM Tris-HCl (pH 8.0), 277 mg of 3 (10 mM), 5 mM of $Mg^{2+}$, 15 mM of GDP-Fucose, and 4 mg of FucT. 20 units of alkaline phosphatase were added into reaction system to hydrolyze the newly formed GDP to improve the reaction yield. The reaction was carefully shaken at 37° C. for overnight and monitored by TLC (EtOAc/MeOH/H2O/HOAc=5:2:1.4:0.4). Once reaction finished, the product was purified by using Bio-Gel™ P-2 column. 211 mg of 4 was obtained in 64% isolated yield regarding 3. Product was confirmed by MALDI-TOF-MS analysis.

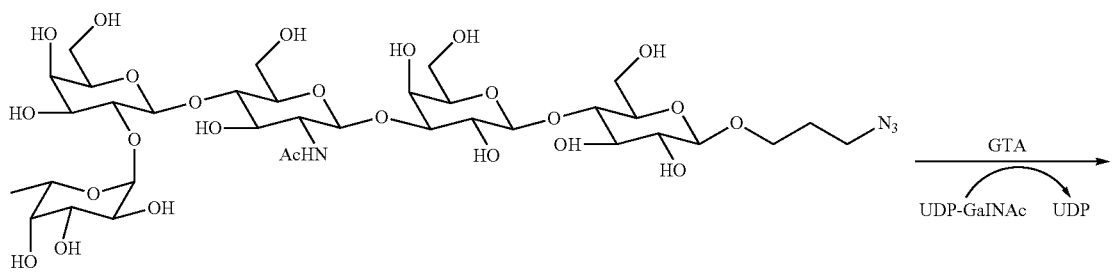

4

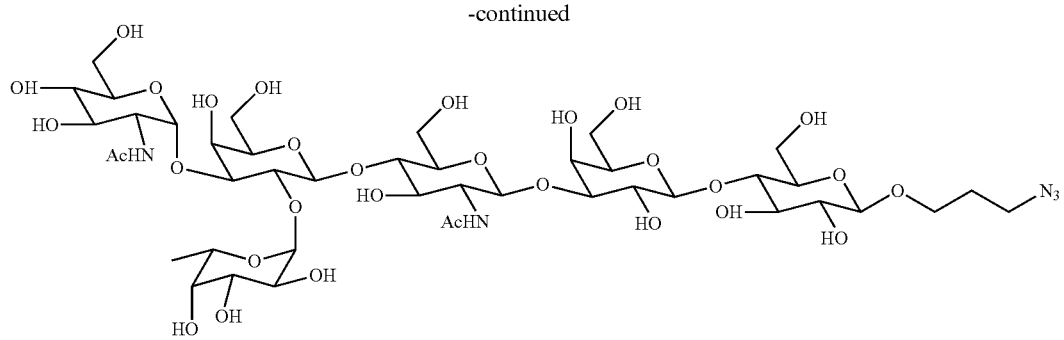

5

5 (blood A-antigen) was prepared from blood 0-antigen using GTA from human. In detail, reaction was performed in a final volume of 14 ml mixture containing 20 mM Tris-HCl (pH 8.0), 66 mg of 4 (5 mM), 3 mM of $Mg^{2+}$, 7 mM of UDP-GalNAc, and 5 mg of GTA. The reaction was carefully shaken at 37° C. for overnight for the formation of 5. The reaction was monitored by TLC (isopropanol/NH4OH/H2O=7:3:2). Once reaction finished, the product was purified by using Bio-Gel™ P-2 column. 45 mg of 5 was obtained in 56% isolated yield regarding 4. Product was confirmed by MALDI-TOF-MS analysis.

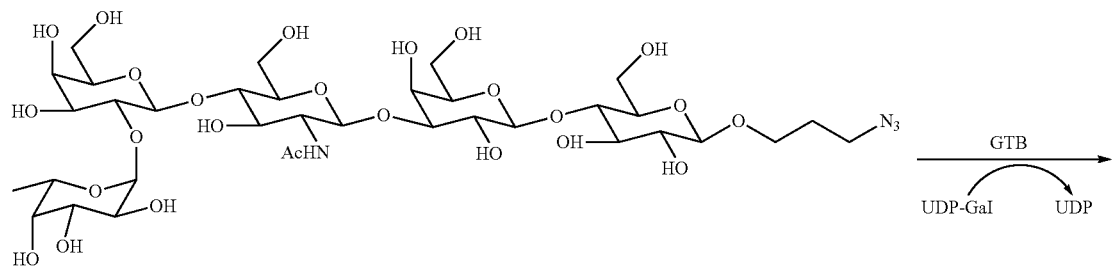

4

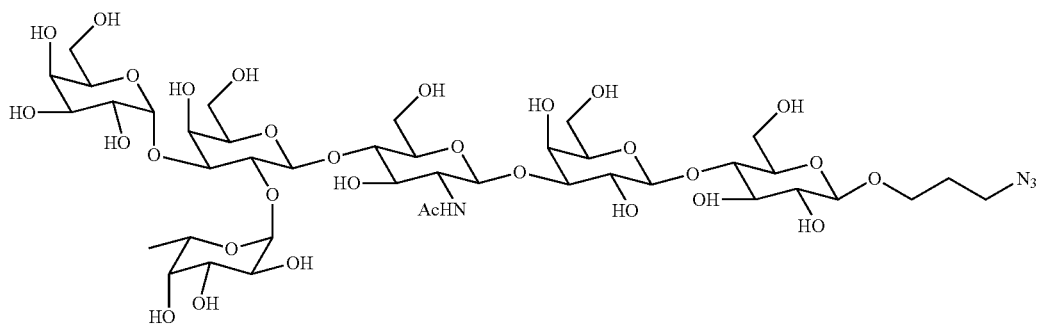

6

6 (blood B-antigen) was prepared from blood O-antigen using GTB from human. In detail, reaction was performed in a final volume of 14 ml mixture containing 20 mM Tris-HCl (pH 8.0), 66 mg of 4 (5 mM), 3 mM of $Mg^{2+}$, 7 mM of UDP-Gal, and 5 mg of GTB. The reaction was carefully shaken at 37° C. for overnight for the formation of 6. The reaction was monitored by 20 TLC (isopropanol/NH4OH/H2O=7:3:2). Once reaction finished, the product was purified by using Bio-Gel™ P-2 column. 39 mg of 6 was obtained in 51% isolated yield regarding 4. Product was confirmed by MALDI-TOF-MS analysis.

Synthesis of Globo-H and Related Glycans

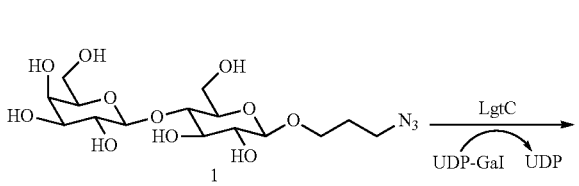

1

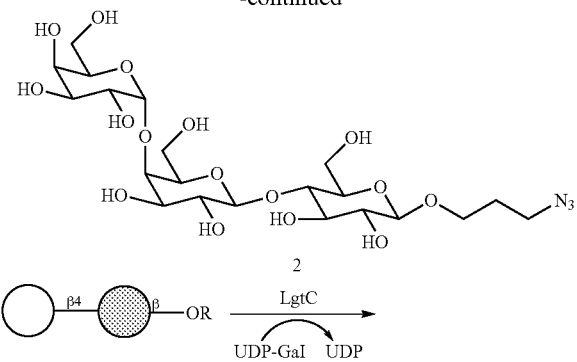

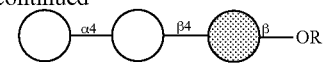

2 was prepared from 1. In detail, a reaction mixture in a final volume of 10 ml containing 50 mM Tris-HCl, 85 mg of 1 (2 mmol), 153 mg of UDP-Gal (2.5 mmol), 5 mM of $Mg^{2+}$, 2 mg of LgtC was carefully shaken at 37° C. to allow the formation of 2. The reaction was monitored by TLC (EtOAc/MeOH/H2O/HOAc=5:2: 1.4:0.4). Once the reaction was no longer move forward, equal volume ethanol was added to remove proteins and the solution was concentrated in vacuo. After purification by using Bio-Gel™ P-2 column. 99 mg of 2 was obtained in 86% yield regarding 1.

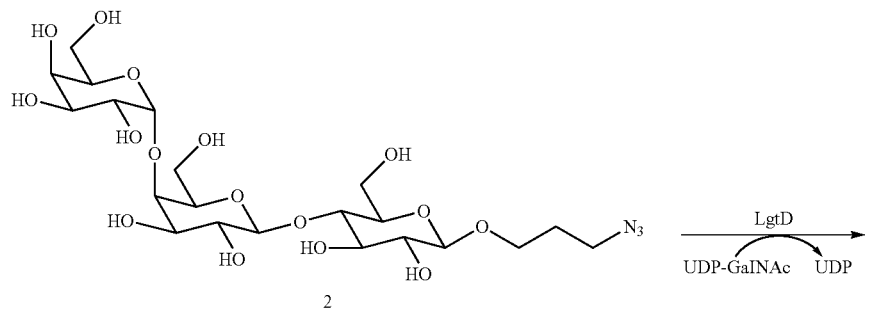

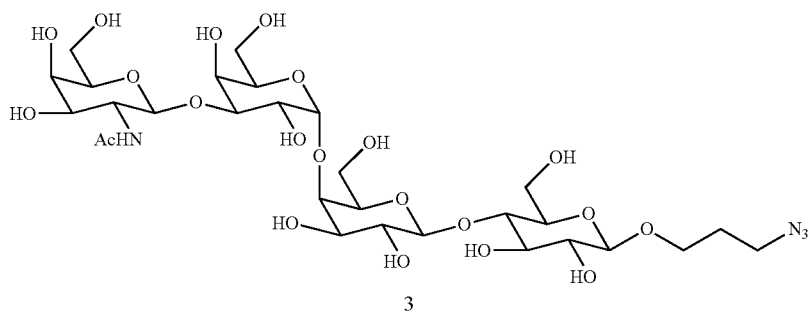

In a reaction mixture of 5 ml volume, 50 mM Tris-HCl, 59 mg of 2 (1 mmol), 5 mM of $Mg^{2+}$, 98 mg of UDP-GalNAc (1.5 mmol), 2 mg of LgtD were added. the reaction was carefully shaken at 37° C. overnight to allow the formation of 3. Once the reaction finished, equal volume ethanol was added to remove proteins and the solution was concentrated in vacuo. After purification by using Bio-Gel™ P-2 column, 63 mg of 3 was obtained in 80% yield regarding 2.

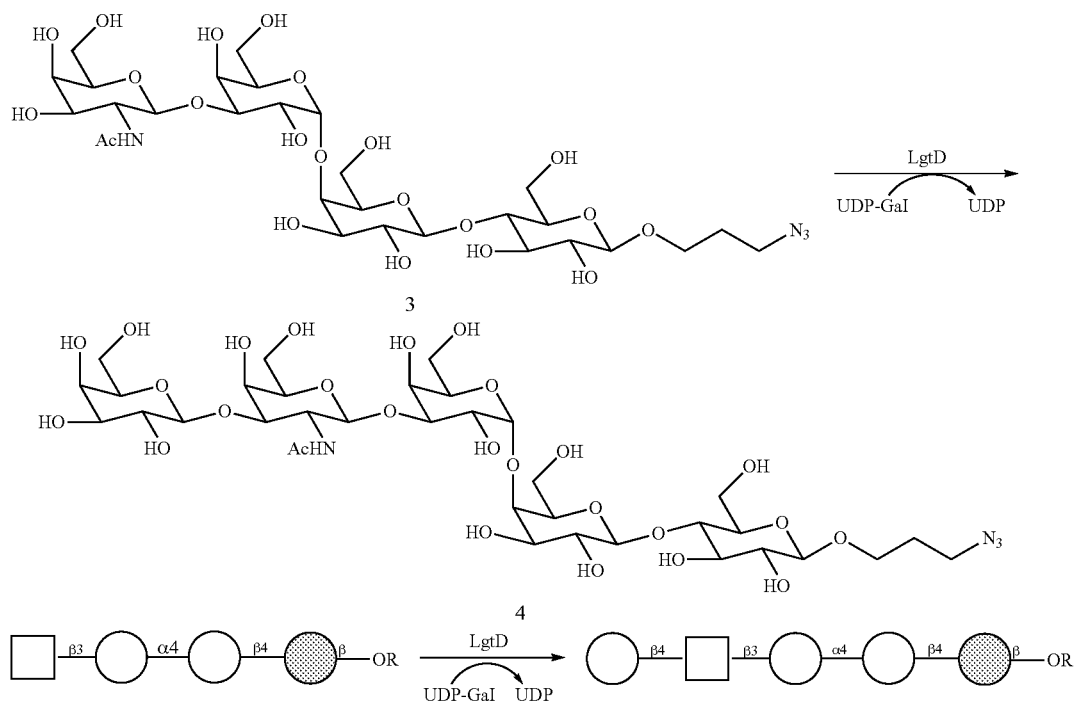

4 was prepared from 3. A 5 ml of reaction mixture containing 50 mM Tris-HCl, 5 mM of Mg', 47 mg of 3 (0.6 mmol), 65 mg of UDP-Gal (1 mmol), and 5 mg of LgtD was carefully shaken at 37° C. overnight to allow the formation of 3. 5 unit of alkaline phosphatase was added to hydrolyze the formation of UDP to improve the reaction yield. After purification by using Bio-Gel™ P-2 column, 36 mg of 4 was obtained in 62% yield.

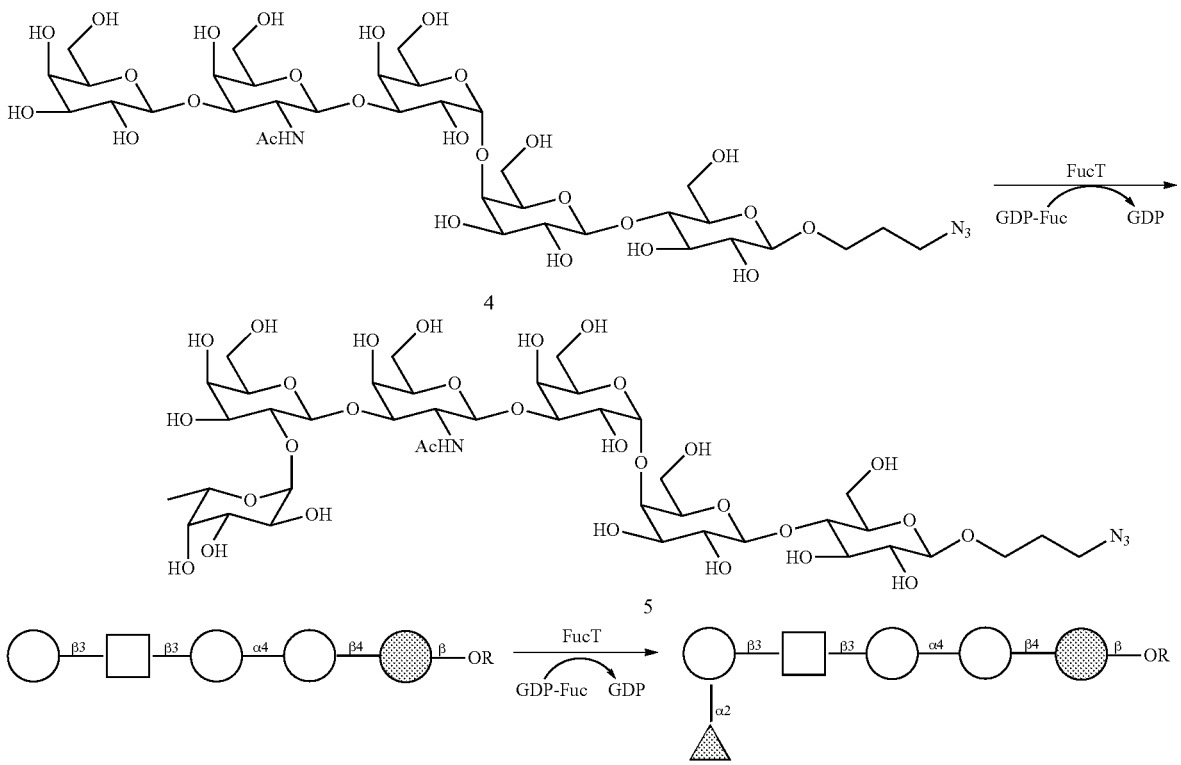

GloboH (5) was prepared from 4. A reaction mixture containing 50 mM Tris-HCl, 5 mM of $Mg^{2+}$, 29 mg of 4 (0.3 mmol), 32 mg of GDP-Fuc (1 mmol), and 2 mg of FucT was carefully shaken at 37° C. overnight to allow the formation of GloboH. 5 unit of alkaline phosphatase was added to hydrolyze the byproduct GDP to improve the reaction yield. After purification by using Bio-Gel™ P-2 column, 24 mg of GloboH was obtained in 71% yield.

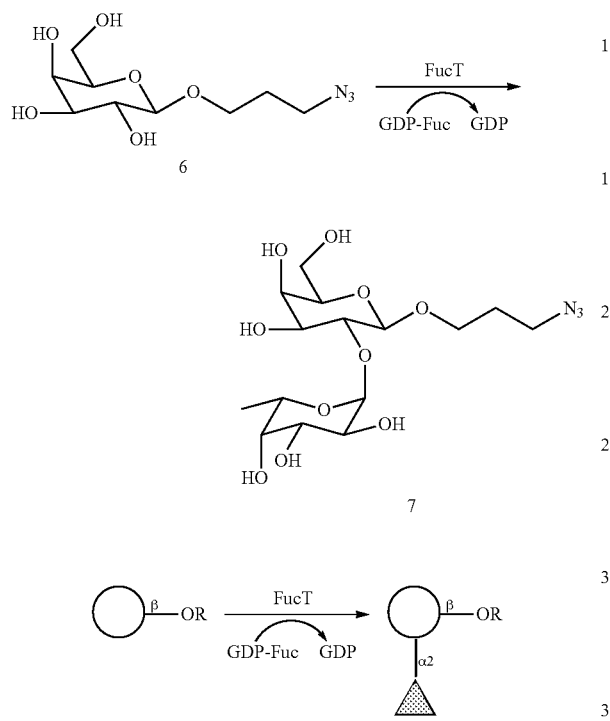

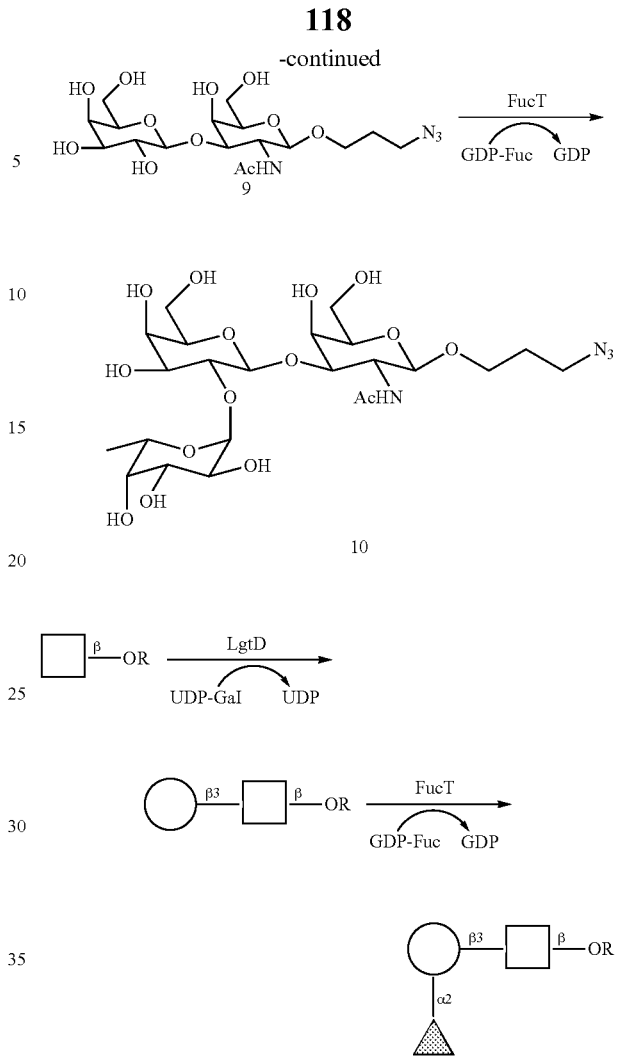

In a 10 ml of reaction mixture, 50 mM Tris-HCl, 53 mg of 6 (2 mmol), 5 mM of $Mg^{2+}$, 158 mg of GDP-Fucose (2.5 mmol), 3 mg of FucT were added. the reaction was carefully shaken at 37° C. overnight to allow the formation of 7. Once the reaction finished, equal volume ethanol was added to remove proteins and the solution was concentrated in vacuo. After purification by using Bio-Gel™ P-2 column, 61 mg of 7 was obtained in 75% yield.

10 was synthesized from 8 by two reaction steps. In a 5 ml of reaction mixture, 50 mM Tris-HCl, 5 mM of $Mg^{2+}$, 61 mg of 8 (2 mmol), 153 mg of UDP-Gal (2.5 mmol), 4 mg of LgtD were added. the reaction was carefully shaken at 37° C. overnight to allow the formation of 9. Once the reaction finished, equal volume ethanol was added to remove proteins and the solution was concentrated in vacuo. After purification by using Bio-Gel P-2 column, 77 mg of 9 was obtained in 83% yield regarding 8. In second reaction step, 77 mg of 9 was incubated in a 5 ml of 50 mM Tris-HCl with 5 mM of Mg', 47 mg of 9 (1 mmol), 127 mg of GDP-Fucose (2 mmol), and 3 mg of FucT. The reaction was carefully shaken at 37° C. overnight to allow the formation of 10. Once the reaction finished, equal volume ethanol was added to remove proteins and the solution was concentrated in vacuo. After purification by using Bio-Gel™ P-2 column, 69 mg of 10 was obtained in 57% yield regarding to 8.

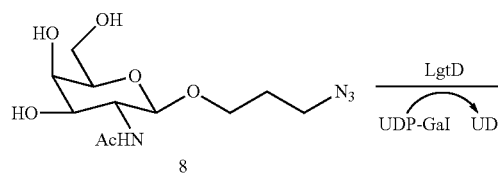

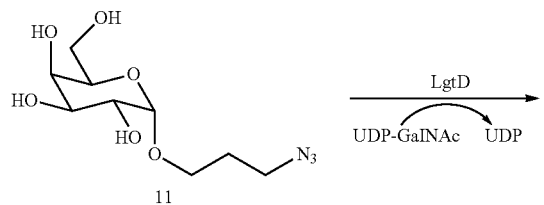

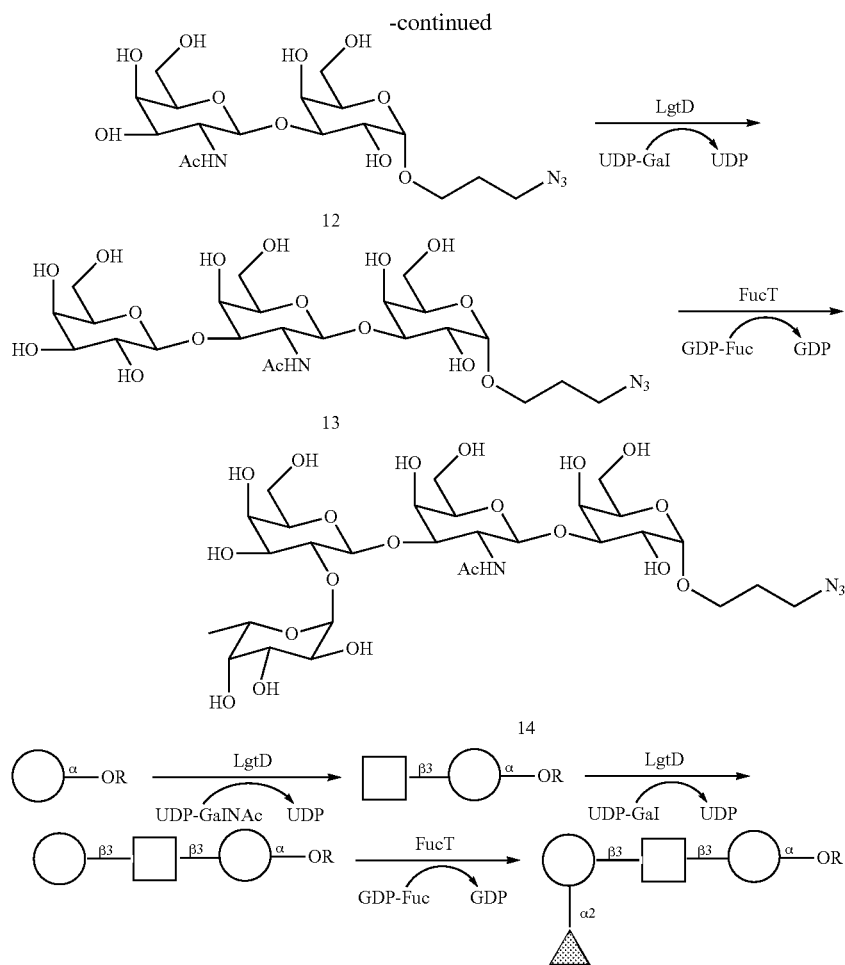

14 was prepared from 11 stepwisely. In a 10 ml of reaction system, 50 mM Tris-HCl, 5 mM of $Mg^{2+}$, 53 mg of 11 (2 mmol), 163 mg of UDP-GalNAc (2.5 mmol), and 2 mg of LgtD were added. The reaction was performed at 37° C. overnight to allow the formation of 12. 12 was purified by Bio-Gel™ P-2 column (75 mg, 81% yield). Then, 75 mg of 12 was dissolved in 10 ml water containing 50 mM Tris-HCl, 5 mM of $Mg^{2+}$, 122 mg of UDP-Gal (2 mmol) and 7 mg of LgtD were added. In addition, 5 units of alkaline phosphatase was added to hydrolyze the byproduct GDP to improve the reaction yield. The reaction was performed at 37° C. 13 was obtained after P-2 gel purification. In last reaction step, 32 mg of 13(0.5 mmol) was dissolved in 5 ml of water containing 50 mM Tris-HCl, 5 mM of $Mg^{2+}$. 1.5 mg of FucT and 48 mg of GDP-Fuc(0.75 mmol) was added to start the reaction at 37° C. 2 units of alkaline phosphatase was added to hydrolyze the byproduct GDP to improve the reaction yield. 14 was purified by P-2 column (28 mg, 73% yield).

Gradient PCR and Tm Determination

Initially a gradient PCR was performed to figure out the optimal melting temperature to be used in the further quantitation experiments. Platinum™ Pfx DNA Polymerase was used for the PCR, approximately 26 µg of template, 1 µL of primers (10 µM), 1 mm dNTP, 10× amplifying buffer, $MgSO_4$, Polymerase and nuclease free water was used for a typical 25 µL reaction (Table 7). Standard thermocycling condition were used with different temperature in the melting phase (95° C. for 10 min, X° C. for 30 s, 95° C. for 15 s, 13 cycles) wherein X represents the melting phase and temperature gradient from 50° C.-60° C. were tested during this phase. The amplified PCR products were analyzed using 4% agarose gel electrophoresis. $T_m$ determined using this method was used for qPCR (FIG. 16).

TABLE 7

Components used in reactions.

| Component | 25 µl | 50 µl | Final Concentration |
|---|---|---|---|
| 10X Amplifying Buffer | 5 | 10 | — |
| MgSO4 | 1 | 2 | — |
| dNTP(10 mM) | 0.75 | 1.5 | 0.3 mM |
| Forward Primer(10 uM) | 0.75 | 1.5 | 0.3 uM |
| Reverse Primer(10 uM) | 0.75 | 1.5 | 0.3 uM |
| Template(1 uM) | 1 | 2 | 0.04 |
| Polymerase | 0.3 | 0.5 | — |
| Nuclease Free Water | 15.4 | 31 | — |

Synthesis of Glycan DNA Conjugates

Glycan(Antigen)-DNA Conjugates were synthesized using Azido-Alkyne cycloaddition click reaction. The 5'-/SHexynyl-terminated DNA was procured from the commercial suppliers (IDT) with standard desalting purified. Desalted DNA was HPLC purified before click conjugation. All glycans were synthesized via chemo enzymatic method with the azido propyl linker at the reducing end as described above.

Click Reaction Procedure

5'-Hexynyl-terminated DNA (500 μM, 20 μL), azido glycan (1.5 mM, 30 μL), 2M TEA buffer (pH 7, 20 μL, final concentration of 0.2 M), 5 mM of freshly prepared Ascorbic acid solution (20 μL, final concentration 0.5 mm), 10 mm of copper-TB TA in 55% DMSO (10 μl, final concentration 0.5 mm) and 50 volume % DMSO (100 μl) were mixed together in a tube. The reaction mixture was vortexed and kept at room temperature for overnight. The reaction mixture was purified using Micro Bio-Gel™ P-30 Chromatography Columns (20 base pair cut-oft). A, B and O glycan conjugates in the initial PCR and qPCR methods are directly used after this step without further purification.

Figure 27:
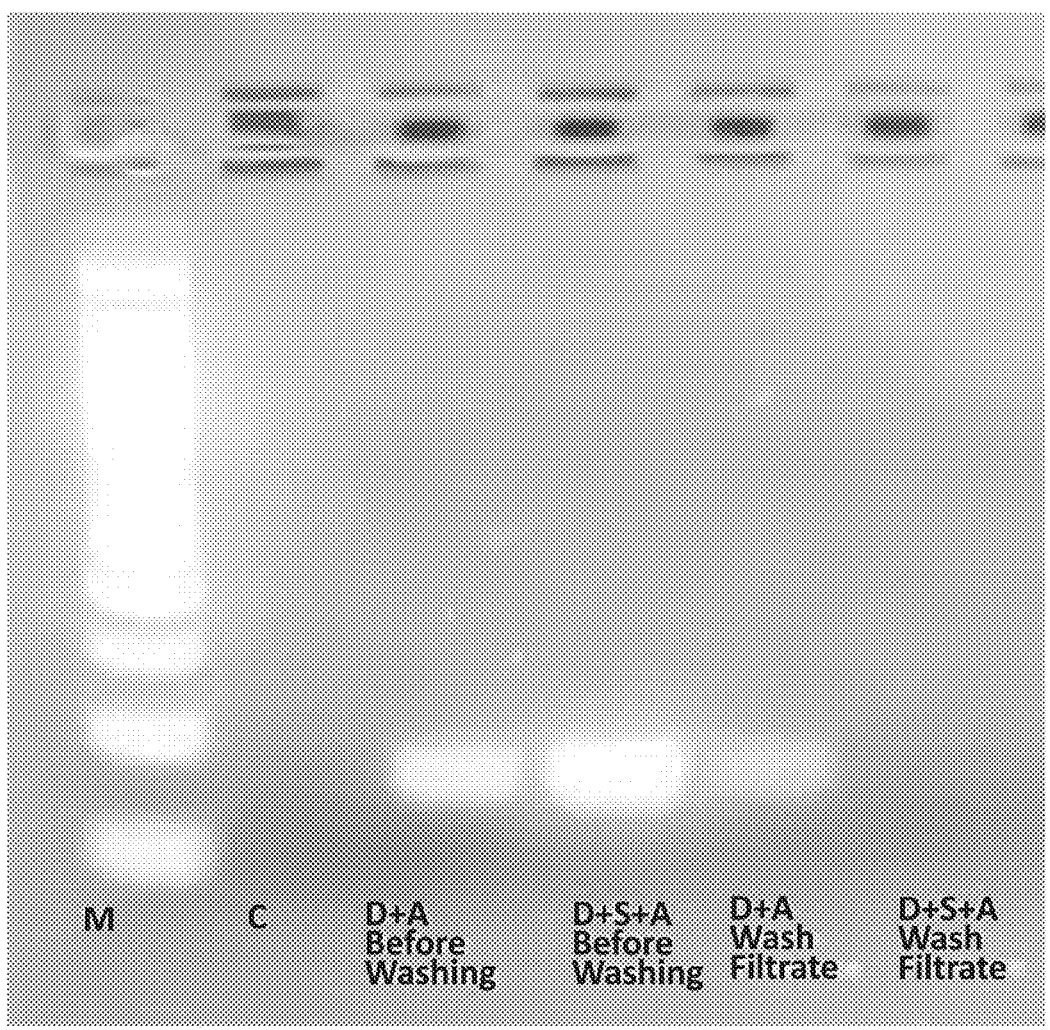
FIG. 27 shows a gel analysis of 'clicked' DNA. Lane 1, ladder; lane 2, empty; lanes 3 and 4, B DNA and B+DNA elution after incubation with the anti-B antibody; lanes 5 and 6, B DNA and B+DNA wash fraction collected before final elution.

Any presence of residual unreacted DNA was further tested by PCR amplification and gel electrophoresis. Recovered reaction mix was incubated with the specific antibody for two hours and washed with the washing buffer, and later eluted with the elution buffer. Both wash and elution buffers were collected and performed a PCR. Gel analysis of the PCR product did not show a band in the wash buffer (residual unreacted DNA) but a strong band was seen in elution buffer indicating all DNA is coupled with the azido sugar (FIG. 27), For the NGS application, the product was dried and further HPLC purified. The concentration of the Glycan (Antigen)-DNA Conjugates was determined by absorbance at 260/280 using Nanodrop (ThermoFisher).

Figure 33B:
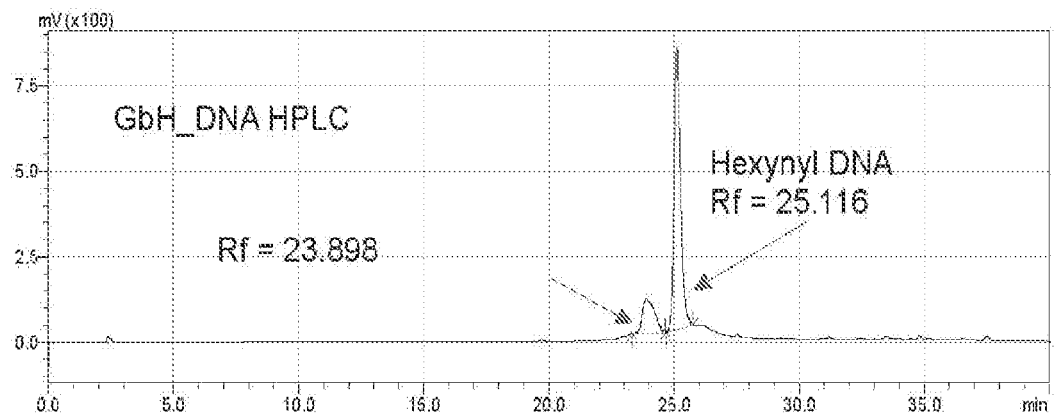
FIG. 33B shows HPLC traces of the DNA-glycan conjugate before purification, and at FIG. 33C the final product after click conjugation.
Figure 33C:
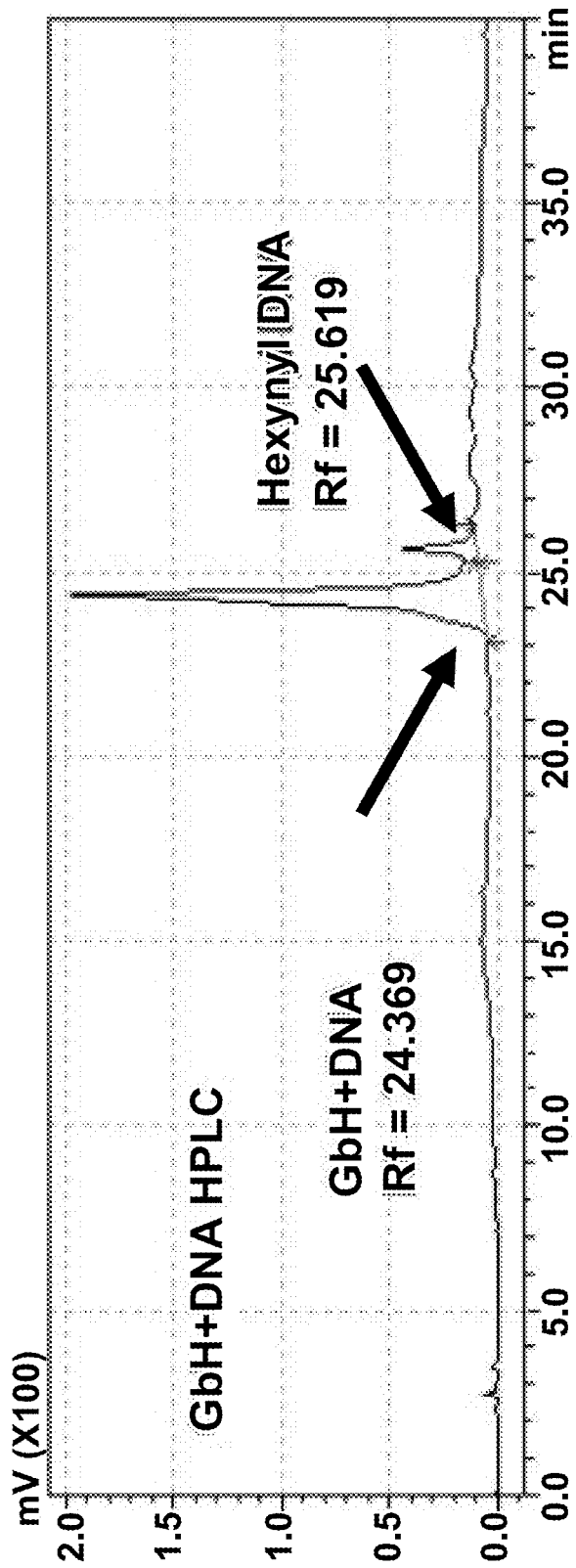
FIG. 33A shows a representative reaction to produce a DNA-glycan conjugate.
FIG. 33D shows the MALDI-TOF spectra of the GbH+DNA conjugate.
Figure 33D:
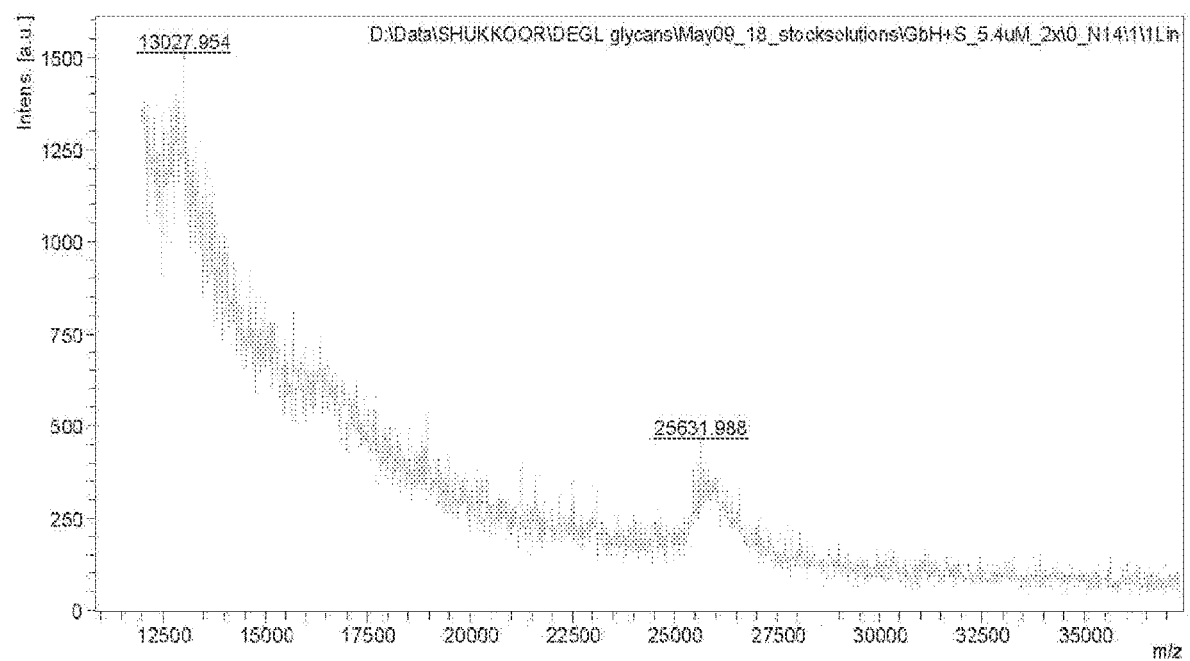

DNA codes for each glycan were purified by HPLC before used in click reaction. Preparative HPLC purification was achieved using following conditions; Agilent 1200 HPLC system, Xbridge semi prep C18 column, 5 uM, 10× 150 mm; Solvent A: pH 7.0 TEAA buffer 0.1 M, Solvent B: 20% ACN in solvent A; 5% B to 95% B over 30 minutes with a flow rate of 1.2 mL/minute. After click reaction, products were either gel purified or HPLC purified (NGS) and analyzed by HPLC and MALDI-TOF. Full characterization of GbH+DNA conjugate is provided as an example (see FIG. 33).

Analytical HPLC method: Shimadzu LC20AT, Eclipse Plus C18, 3.5 uM, 4.6×100 mm column; Solvent A: pH 7.0 TEAA buffer 0.1 M, Solvent B: 20% ACN in solvent A; 5% B to 95% B over 30 minutes, 30-40 minutes 95% B with a flow rate of 0.6 mL/minute.

MALDI-TOF MS Analysis

Matrix preparation: 10 mg 3-Hydroxypicolinic Acid (HPA) was dissolved in 200 ul of 50% ACN; in another tube, 10 mg of dibasic ammonium citrate (DAC) was dissolved in 200 ul of H2O. Then mixed HPA to DAC in 8:1 in a new tube for the final working matrix. Next, 1 uL of matrix solution was spotted to the MALDI target plate and allowed to air dry, on top of the dried matrix 1 uL of HPLC purified DNA glycan conjugates were spotted, allowed to complete dryness and analyzed using Bruker MALDI-TOF instrument. A representative reaction is disclosed at FIG. 33.

PCR Comparison of DNA and G+DNA

Figure 28:
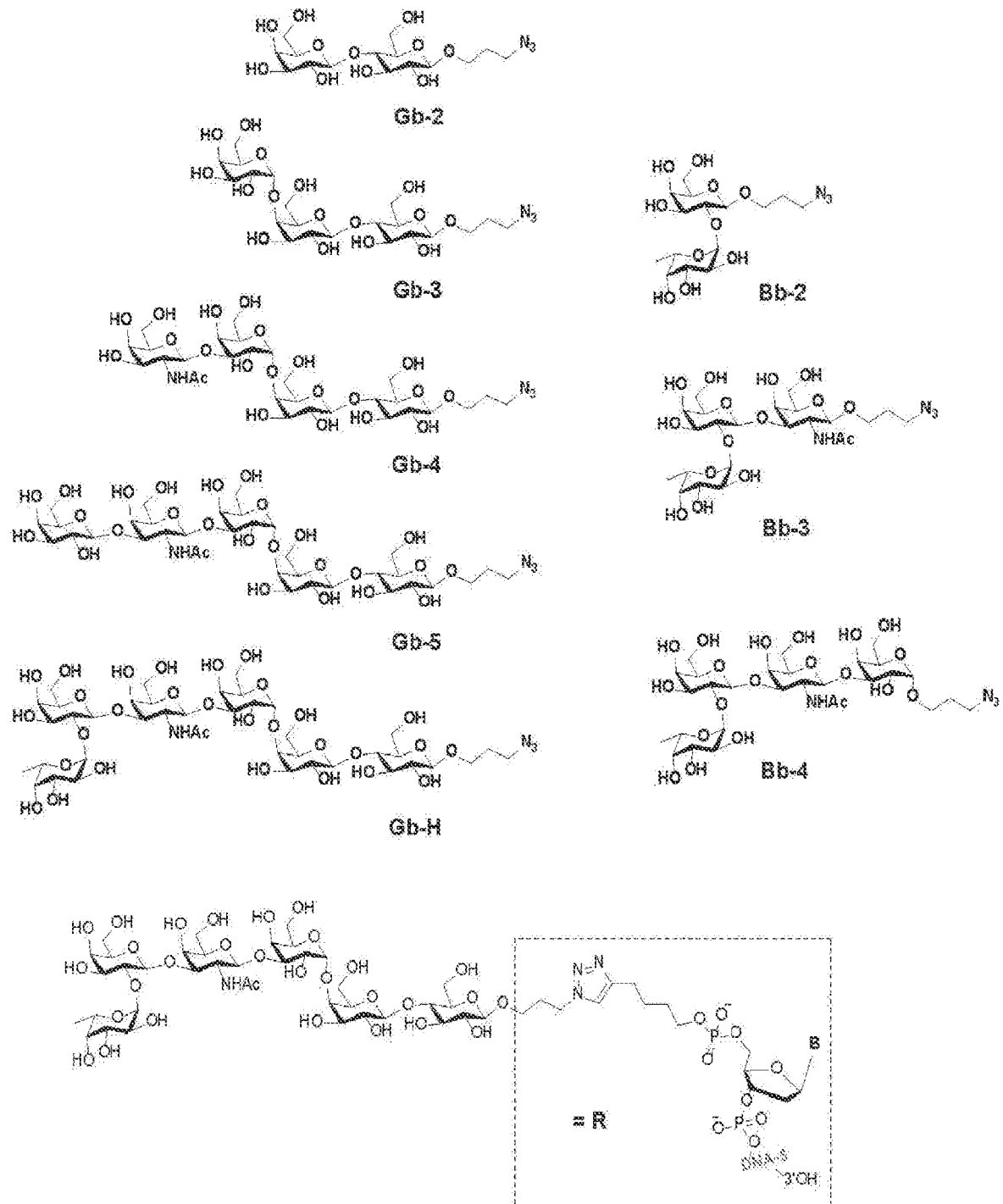
FIG. 28 shows glycan structures used for conjugation with alkyne DNA and alkyne biotin.
Figure 29:
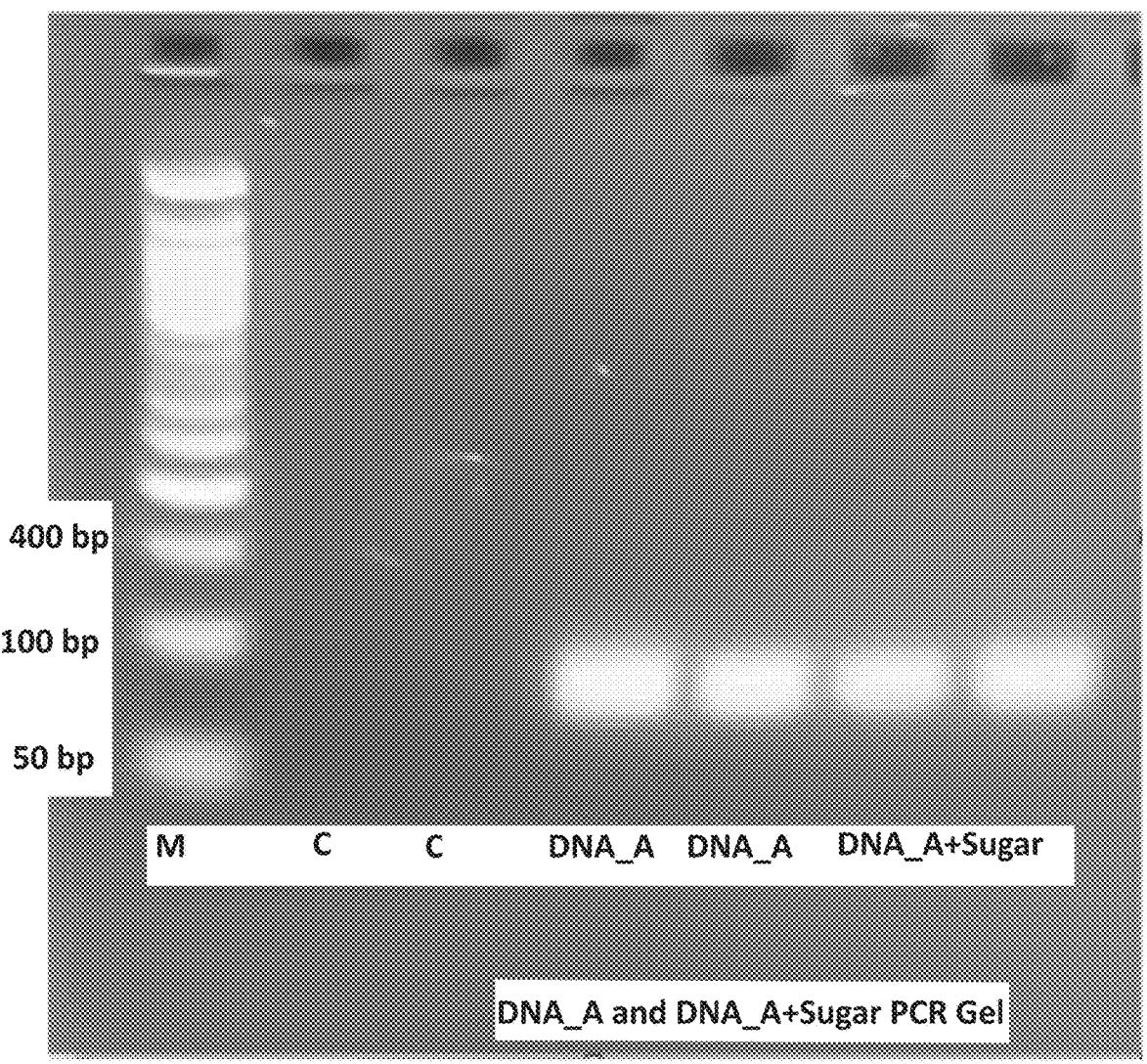
FIG. 29 shows PCR comparison of pure DNA and glycan conjugated DNA. Lane 1, DNA 100 Ladder; lane 2, Control; lane 3, Control; lane 4, DNA_A; lane 5, DNA_A; lane 6, G+DNA_A; lane 7, G+DNA_A.

A PCR comparison was conducted between pure DNA and G+DNA to make sure that the DNA can be used for further PCR reaction after conjugation with glycan. PCR was conducted under the same conditions as stated under Gradient PCR and Tm Determination and analyzed using 4% agarose gel electrophoresis (FIG. 28).

qPCR Methods

General qPCR protocol for a typical 12.5 μL reaction: The glycan(Antigen)-DNA Conjugates were added to 6.25 μL 2× Maxima SYBR Green/ROX qPCR Master Mix with 1 μL primers (Forward Primer—500 nM and Reverse Primer—300 nm). qPCR was performed with Applied Biosystems Stepone™ System (50° C. for 2 mins (Holding), 95° C. for 10 mins (Holding), 95° C. for 15 s, 60° C. for 10 s, 72° C. for 10 s for 40 cycles).

Ct or threshold cycle, is a measurement of signal intensity for qPCR experiments. In a qPCR experiment, PCR is performed in presence of a fluorogenic intercalating dye (SYBR™ Green). The dye intercalates with double-stranded DNA, as more double-stranded DNA is produced in each PCR cycle the dye increases the fluorescence intensity. Once the fluorescence intensity reaches a threshold level, the cycle number is recorded by the instrument as Ct value. Therefore, sample having large amount of DNA will have a lower Ct value compared to those samples containing relatively less amount of DNA.

Standard Curve Plot of DNA and G+DNA

To prove the consistency over concentration for both pure DNA and G+DNA, a qPCR standard curve reaction was conducted over a series of 8 different concentrations (2.4 nM, 1.2 nM, 600 nM, 206 nM, 130 nM, 64 pM, 32 pM, and 16 pM) with standard thermocycling conditions stated above Table 8.

TABLE 8

Components used for standard curve reaction.

| Component | Volume (in uL) |
| --- | --- |
| 2x Maxima SYBR ™ Green/ROX qPCR master mix | 6.25 |
| Forward Primer(500 nm) | 1 |
| Reverse Primer(300 nm) | 1 |
| Template(Gradient as stated above) | 1 |
| Nuclease Free Water | 3.25 |

Immunoprecipitation of Antibody-Antigen-DNA Conjugates

10 μL of glycan(antigen)-DNA Conjugate (5 μM) was incubated with 2 μL of antibody (if plasma was used then 2 μL of plasma was diluted to 8 μL using water) for 2 hours at room temperature. After two hours, the reaction volume was made up to 100 μL using TBST buffer and added to 20 μL of prewashed A/G protein bead, and incubated for one hour at room temperature with occasional shaking at an interval of 15 mins. After one hour the beads were washed thoroughly for 7 times using TBST buffer. After washing the beads were reconstituted in 20 μL of TBST buffer. The beads (2 μL) were directly used as template for qPCR analysis.

DNA Encoded Glycans for the Detection of Glycan Binding Proteins

Selectivity and Specificity Analysis of DEGL

Glycan-DNAs with the mixture of antibodies A, B and O (G+DNA Vs ABO Abs 1:1:1): Antibody mixture was prepared by mixing 2 μL each of Blood Group A Antigen Antibody HE-193 (MA1-19693), Blood Group B Antigen Antibody HEB-29 (MA1-19691) and Blood Group ABH Antigen Antibody RE-10 (MA1-19694). Then, 10 μL of each glycan conjugates (2.5 μM) were incubated with 2 μL of antibody mix separately. Immunoprecipitation and qPCR analysis was performed as described above. A no antigen control with none conjugated DNA (A DNA, 2.5 μM) was used in immunoprecipitation and a no template control was used in qPCR. G2+B DNA vs A, B, and O antibodies: In this experiment, 10 μL of G2+B DNA (2.5 μM) was incubated with 2 μL of each antibody. A no antibody control was used in immunoprecipitation and a no template control was used in qPCR. Immunoprecipitation and qPCR analysis was performed as described above.

Globo-H vs VK-9: The immunoprecipitation procedure for Globo-H with VK9 were same as stated in Immunoprecipitation of Antibody-Antigen-DNA Conjugates. The volume of antibody used was 2 µL and Globo-H was 10 µL (2.5 µM).

ELISA Experiment.

Figure 30:
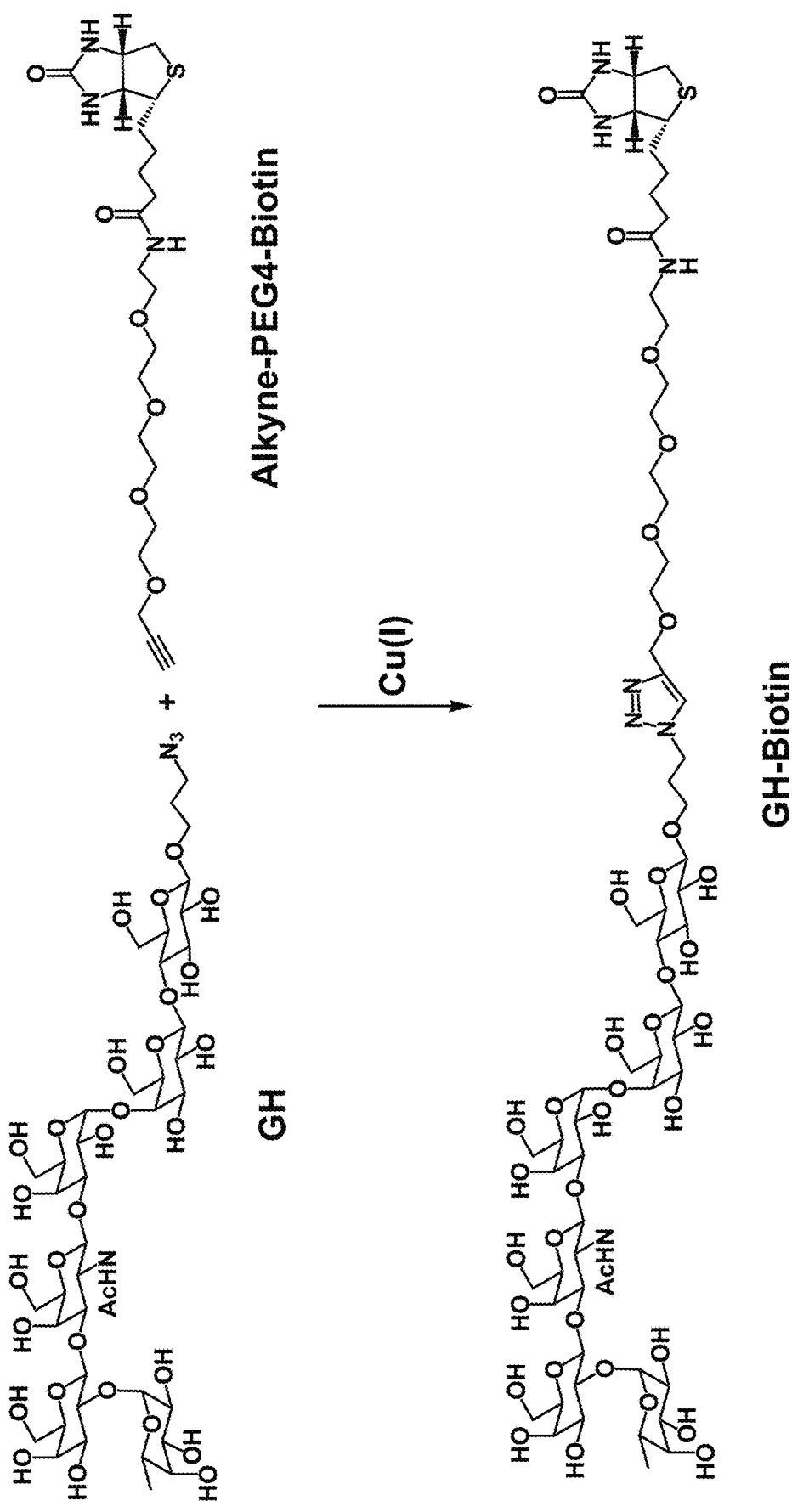
FIG. 30 shows MALDI TOF analysis of GH and biotinylated-GbH.

A 96-well plate (Costar® Polystyrene High Binding Plate 3590) was coated with 100 ml of 10 ug/ml Streptavidin (Sigma) in 0.01 M PBS (pH 7.4) at 4° C. overnight. The coated plate was then washed with 150 ul of 0.05% Tween-20/PB S buffer (pH 7.4) (PBST) for three times and then add 100 ul Biotinylated sugar (synthesized via click reaction, FIG. 30) for capturing. After 30 minutes, the plate was washed. For DNA-sugar ELISA, the only difference was to coat the DNA-sugar onto plastic surfaces directly using Pierce DNA Coating Solution for overnight. Then the plate was blocked with 2% (w/v) BSA in PBST for 2 hrs. After washed with another 150 ul PBST for 3 times, 100 ul VK9 (a mouse IgG anti-Globo H monoclonal antibody) with a series of dilution was added for incubation at room temperature for 2 hrs. After washing with 200 ul PBST for 6 times, HRP-goat anti-mouse IgG(H+L) was added to the plate at a dilution as recommended for 1 hr at room temperature. After washed with another 200 ul PBST for 6 times, 100 ul TMB solution was added to the plate and then stopped by 100 ul 1 M phosphoric acid. The plate was then read at OD450 with a plate reader (PerkinElmer®, 2030 Multilabel Reader Victor®). The result was calculated by minus OD450 value of control (no antibody).

NGS Experiment
NGS Protocol

1. Selection: 10 ul of 100 nM DEGL was incubated with 2 ul (1 ug) VK9 antibody (Globo H Monoclonal Antibody, eBioscience; Catalog Number: 14-9700-82) for 2 hrs at 37° C. After 2 hrs 0.2 ul of Biotin Conjugated Goat Anti-Mouse IgG Secondary Antibody (Thermofischer Scientific™; Catalog Number:31800), 40 ul of Sheared Salmon Sperm DNA (Thermofischer Scientific™; catalog Number: AM9680) and 50 ul of TB ST buffer (0.1% Tween 20, 0.1% BSA) was added and incubated at 37° C. for 1 hr. 20 ul of Streptavidin Magnetic beads (Dynabeads™ Myone™ Streptavidin Ti; Catalog Number: 65601) was prewashed using PBS as per user instructions. After 1 hr the solution was incubated with prewashed Streptavidin beads for 30 mins at 37° C. The beads were washed 7 times using 100 ul TB ST buffer. The washed beads were then diluted in 20 ul of TBST buffer.

2. Library Preparation: 1 ul of washed streptavidin beads were used for amplification using template primers with Taq polymerase (Thermofischer Scientific™; Catalog Number: EP0402) for 18 cycles. The PCR product was purified using Agencourt AMPure XP Magnetic beads (30% PEG) as per user instructions. The purified PCR product was amplified again using NGS adapters (30 Cycles) and purified using Agencourt AMPure XP Magnetic beads. The purified product's concentration was measured using Agilent 2100 Bioanalyzer. An equimolar solution of 26 pM was prepared which was loaded in Ion Chef™ for the Chip Preparation and sequencing by Ion PGW™.

REFERENCES FOR MATERIALS AND METHODS

1. Zhao, G., et al., Enzymatic route to preparative-scale synthesis of UDP-GlcNAc/GalNAc, their analogues and GDP-fucose. Nat Protoc, 2010. 5(4): p. 636-46.
2. Muthana, M. M., et al., Efficient one-pot multienzyme synthesis of UDP-sugars using a promiscuous UDP-sugar pyrophosphorylase from Bifidobacterium longum (BLUSP). Chemical Communications, 2012. 48(21): p. 2728-2730.
3. Lau, K., et al., Highly efficient chemoenzymatic synthesis of (β1-4-linked galactosides with promiscuous bacterial β1-4-galactosyltransferases. Chemical Communications, 2010. 46(33): p. 6066-6068.
4. Li, Y., et al., Donor substrate promiscuity of bacterial β1-3-N-acetylglucosaminyltransferases and acceptor substrate flexibility of β1-4-galactosyltransferases. Bioorganic & medicinal chemistry, 2016. 24(8): p. 1696-1705.
5. Su, D. M., et al., Enzymatic synthesis of tumor-associated carbohydrate antigen Globo-H hexasaccharide. Org Lett, 2008. 10(5): p. 1009-12.
6. Heidtman, M. I., M. Merighi, and J. M. McCoy, Alpha (1, 2) fucosyltransferases suitable for use in the production of fucosylated oligosaccharides. U.S. Pat. No. 9,029,136.
7. Seto, N. O., et al., Enzymatic synthesis of blood group A and B trisaccharide analogues. Carbohydr Res, 2000. 324(3): p. 161-9.
8. Wang, C. C., et al., Glycan microarray of Globo H and related structures for quantitative analysis of breast cancer. Proc Natl Acad Sci USA, 2008. 105(33): p. 11661-6.

Example 2

Alternative Synthetic Approaches for DNA-Glycan Conjugates

Glycan Code Ligation

Figure 31A:
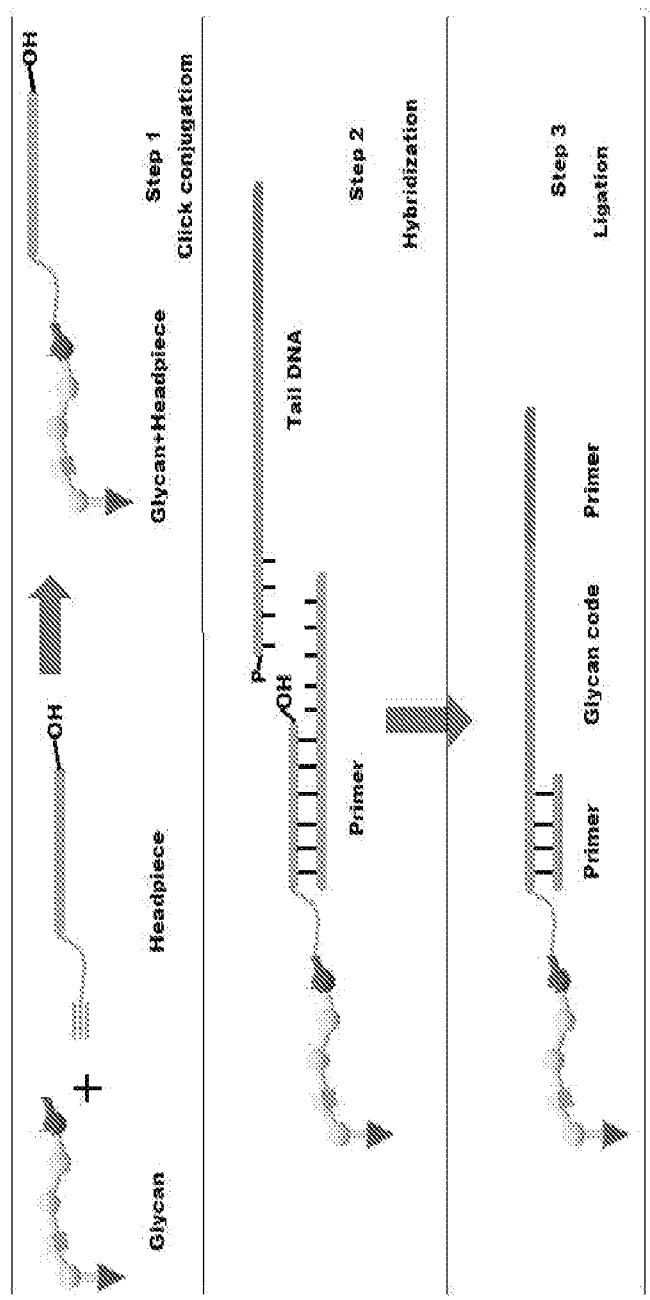
Figure 31C:
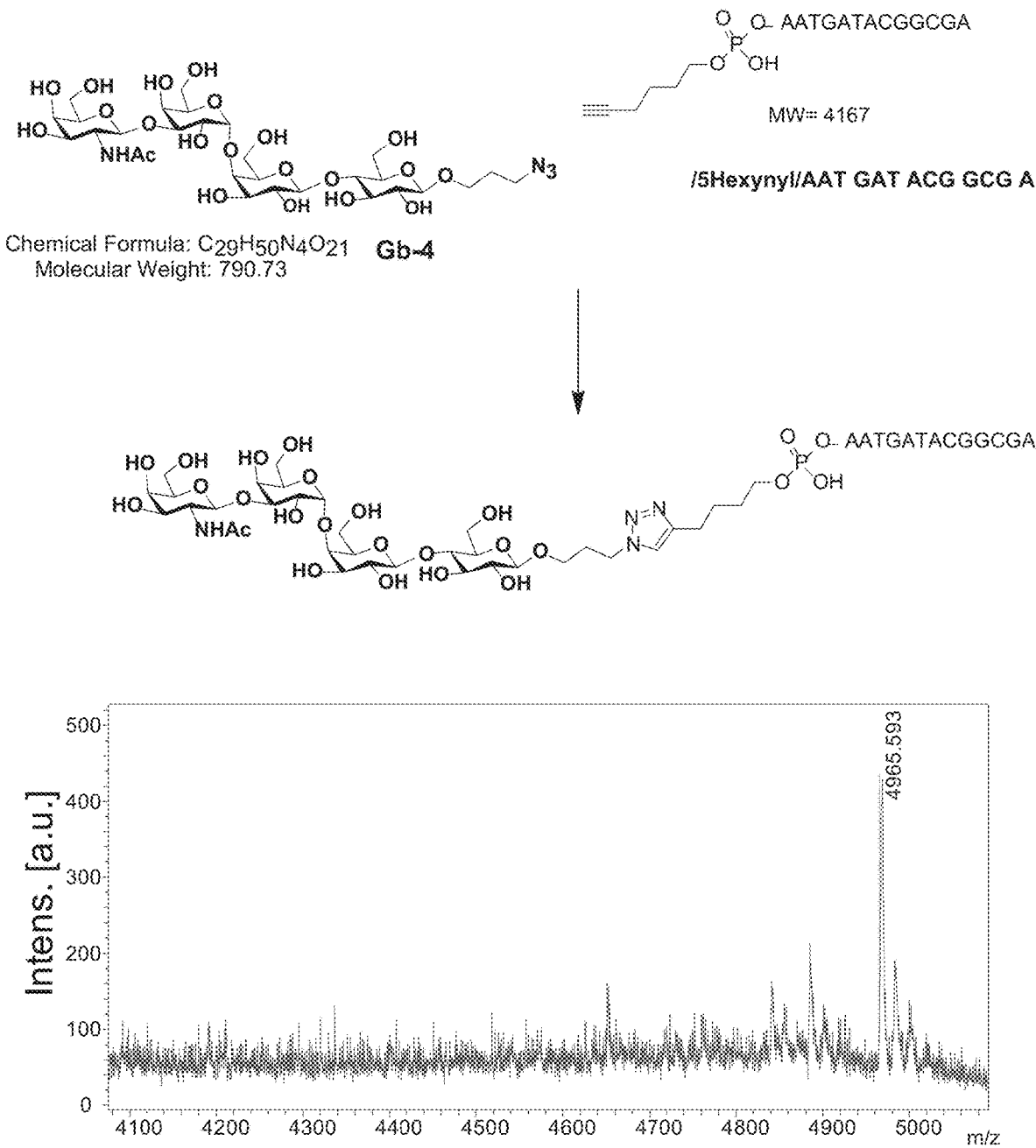

To take advantage of a split and pool strategy with a DEGL, the DNA code was split into two parts, a common primer region (hereafter headpiece) and the glycan code. Then, the headpiece was split with an alkyne modification for the first click conjugation with several glycans in the library. Next, the glycan specific DNA code was ligated via T4 DNA ligase reaction. This approach significantly reduces the cost of DEGL fabrication because DNA codes without the modifications are far less expensive compared to the modified one. Moreover, a small DNA headpiece allows the monitoring and quality control of glycan DNA conjugation via MALDI TOF, and hence many alternative chemical approaches may be also used. This is particularly advantageous when required to include amine terminated glycans to be added to the library. A typical procedure is shown in FIG. 31.

Procedure

Step 1:

Click reactions were carried out according to the previously reported procedure,[1] In brief, 10 ul of DNA headpiece (500 uM) were added to the premixed CuSO4 and THPTA in a 500-uL eppendorf tube (5 uL of 1:1 solution, 10 mM). Immediately added 2.5 equals of azido sugar and followed by ascorbic acid (1 uL, 250 mM). Water was added to make the final reaction volume to 50 uL and the mixture was vortexed and kept at room temperature for two hours. After 2 hours of reaction, the mixture was quenched by addition of excess (5 eq, 12.5 µL) THPTA ligand. The oligo was desalted by passing through Clarion Desalt S-25N MINI Columns (Sorbent technologies), MALDI-TOF was used to evaluate the efficiency of the reaction. Concentration was measured using nanodrop and the conjugated headpiece directly used in the ligation to get the final DNA encoded glycan conjugate.

Steps 2 and 3:

Initially Glycan-headpiece (10 uL, 20 uM) was hybridized with the equimolar primer compliment (10 uL, 20 uM), then added glycan code DNA (10 uL, 20 uM), followed by 5 uL of 5× ligation buffer and 14 uL of water. The solution was heated to 95° C. for 1 min, then cooled to 16° C. over 10 min. A solution of T4 DNA ligase (1 μL, 5 U/μL) was then added and the ligation mixture incubated at 16° C. for 16 h. The DNA product was heated to 70° C. to denature the enzyme and used directly in assays.

Multivalent Presentation of Glycans

Figure 32A:
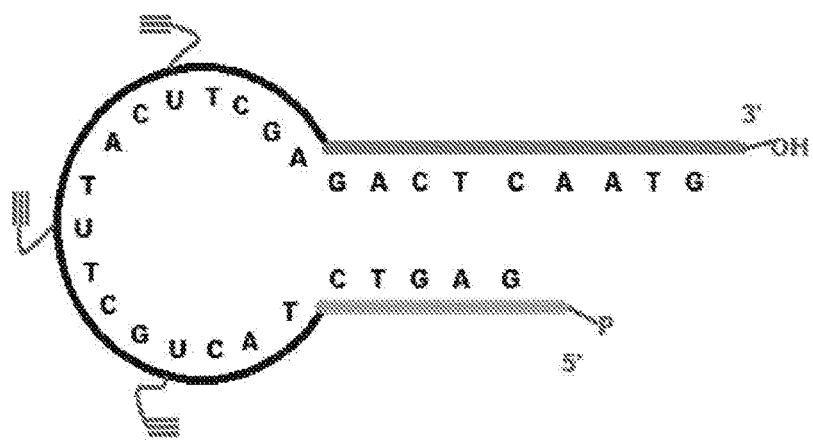
FIG. 32A-B shows an example of fabrication of a DNA-glycan conjugate by glycan code ligation using a multivalent headpiece.
Figure 32B:
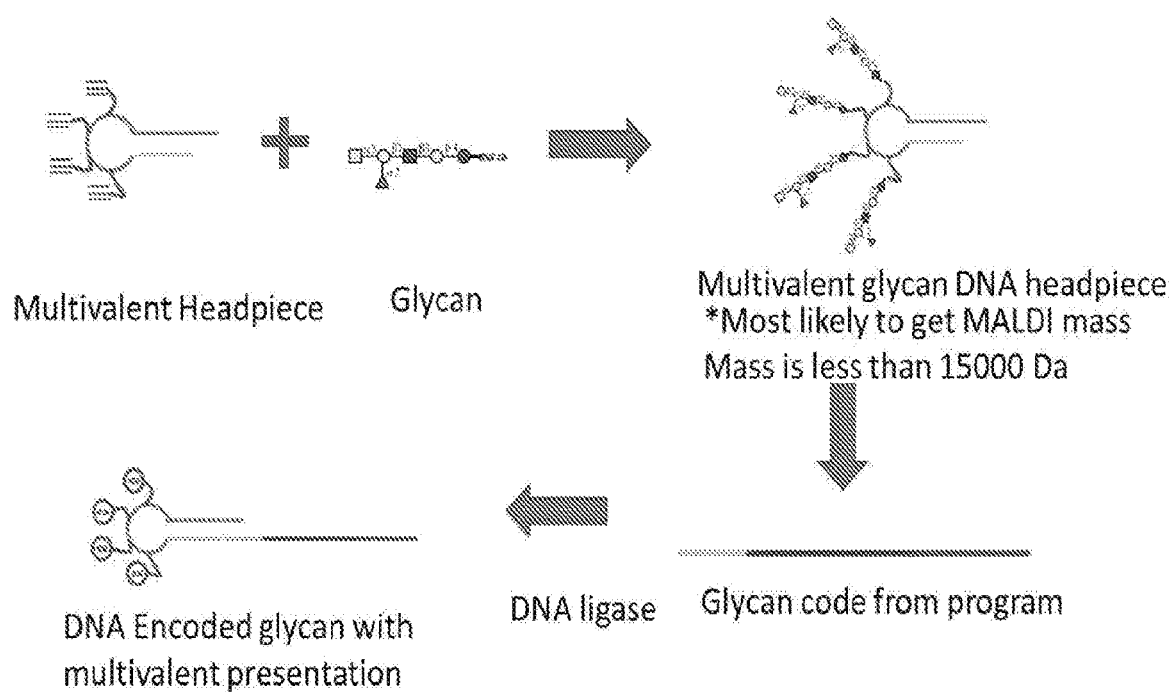

Glycans interact with the target proteins in a multivalent manner, hence to take the advantage of this DNA-glycan conjugates were designed featuring multiple glycans with a single code tail. The same protocol was used for the multivalent glycan conjugate as well (FIG. 32B), but with a different headpiece with three to four different alkyne group as internal modifications (FIG. 32A). The headpiece was designed in a way that a loop is formed with the DNA complementarity and an additional sticky tail for the code DNA to hybridize and facilitate DNA ligation.

REFERENCES

1. Temme, J. S., et al., Directed Evolution of 2G12-Targeted Nonamannose Glycoclusters by SELMA. Chemistry-A European Journal, 2013. 19(51): p. 17291-17295.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A DNA-glycan conjugate comprising:
a glycan comprising a glycan structure of at least two carbohydrate monomers,
wherein each carbohydrate monomer is attached to at least one other carbohydrate monomer by a glycosidic linkage; and
a polynucleotide covalently attached to the glycan, the polynucleotide comprising a plurality of modules, each module comprising a nucleotide string,
wherein the plurality of modules comprises:
a monomer module identifying each carbohydrate monomer present in the DNA-glycan conjugate, and
a linkage module identifying each glycosidic linkage present between each carbohydrate monomer in the DNA-glycan conjugate,
wherein the nucleotide sequence of the plurality of modules corresponds to the glycan structure.

2. The DNA-glycan conjugate of claim 1, wherein each carbohydrate monomer is selected from the group consisting of All, AllNAc, AllN, AllA, Alt, AltNAc, AltN, AltA, Glc, GlcNAc, GlcN, GlcA, Man, ManNAc, ManN, ManA, GpL, GulNAc, GulN, GulA, Ido, IdoNAc, IdoN, IdoA, Gal, GalNAc, GalN, GalA, Tal, TalNAc, TalN, TalA, Tag, TagA, Hep, DDManHep, Dha, LDManHep, Fuc, FucNAc, FucN, Qui, QuiNAc, QuiN, Rha, RhaNAc, RhaN, Tyv, Oli, Par, Dig, 6dAlt, 6dTal, Abe, Api, Col, Neu5Ac, Neu5GC, Kdn, Kdo, Mur, MurNAc, MurNGc, Sia, Neu, Fru, Sor, Psi, Rib, Ara, Xyl, or Lyx.

3. The DNA-glycan conjugate of claim 1, wherein each linkage module identifies a glycosidic linkage that comprises an anomeric configuration and linkage position of each glycosidic linkage, the glycosidic linkage selected from: a1-1, a1-2, a1-3, a1-4, a1-5, a1-6, a1-7, a1-8, a2-1, a2-2, a2-3, a2-4, a2-5, a2-6,a2-7, a2-8, b1-1, b1-2, b1-2, b1-4, b1-5, b1-6, b1-7, b1-8, a?, b?, ?1, ?2, ?2, ?4, ?5, ?6, ?7, ?8, ??,), and (, wherein ? means i) the position or configuration of the anomeric carbon of a monomer is not characterized or (ii) the linkage position between the anomeric carbon of the monomer and the carbon bearing the connecting oxygen of the following monomer is not characterized.

4. The DNA-glycan conjugate of claim 1, wherein the glycan comprises a sequence of at least 3 carbohydrate monomers,
wherein at least 2 of the carbohydrate monomers are joined by a branch, and
wherein the plurality of modules further comprises a branch beginning module and a branch ending module identifying each branch present in the DNA-glycan conjugate.

5. The DNA-glycan conjugate of claim 4, wherein the branch linkage is selected from: a1-1, a1-2, a1-3, a1-4, a1-5, a1-6, a1-7, a1-8, a2-1, a2-2, a2-3, a2-4, a2-5, a2-6,a2-7, a2-8, b1-1, b1-2, b1-2, b1-4, b1-5, b1-6, b1-7, b1-8, a?, b?, ?1, ?2, ?2, ?4, ?5, ?6, ?7, ?8, ??,), and (, wherein ? means i) the position or configuration of the anomeric carbon of a monomer is not characterized or (ii) the linkage position between the anomeric carbon of the monomer and the carbon bearing the connecting oxygen of the following monomer is not characterized.

6. The DNA-glycan conjugate of claim 1, wherein a carbohydrate monomer comprises a modification, and
wherein the plurality of modules further comprises a modification module identifying each modification present in the DNA-glycan conjugate.

7. The DNA-glycan conjugate of claim 6, wherein each modification is selected from 2Y, 4Y, 7Y, 8Y, ?Y, 20H, 40H, 70H, 80H, ?OH, 2V, 4V, 7V, 8V, ?V, 2S, 4S, 7S, 8S, ?S, 2P, 4P, 7P, 8P, ?P, 2J, 4J, 7J, 8J, ?J, 2NAc, 4NAc, 7NAc, 8NAc, ?Nac, 2Ac, 4Ac, 7Ac, 8Ac, ?Ac, 2COOH, 4COOH, 7COOH, 8COOH, ?COOH, 2IN, 3IN, 7IN, 81N, ?IN, 2EE, 4EE, 7EE, 8EE, ?EE, 2EH, 4EH, 7EH, 8EH, ?EH, 2Q, 4Q, 7Q, 8Q, ?Q, 2QS, 4QS, 7QS, 8QS, ?QS, 2PYR, 4PYR, 7PYR, 8PYR, ?PYR, 2ECO, 4ECO, TECO, 8ECO, ?ECO, 2PC, 4PC, 7PC, 8PC, ?PC, 2PE, 4PE, 7PE, 8PE, ?PE, 2ME, 3ME, 4ME, 7ME, 8ME, ?ME, and 3 S, wherein "?" means the position of the modification is not characterized.

8. A kit for identifying a DNA-glycan conjugate bound to a glycan-binding compound, comprising in separate containers:
the DNA-glycan conjugate of claim 1; and
primers for amplification of the polynucleotide of the DNA-glycan conjugate.

9. A kit for determining whether a specific glycan associated with a blood group is present in a sample, comprising in separate containers:
- DNA-glycan conjugates of claim 1, wherein separate DNA-glycan conjugates comprise glycans that comprise a blood group selected from A blood group, B blood group, the O group, blood group P, blood group p1, blood group Pk, blood group FORS1, blood group LKE, blood group I, and blood group I; and
- primers for amplification of the polynucleotides of the DNA-glycan conjugates.

10. A composition of at least two populations of DNA-glycan conjugates, wherein each population of DNA-glycan conjugate is different and comprises the structure of the DNA-glycan conjugate of claim 1.

11. A library comprising the DNA-glycan conjugate of claim 1 and at least two different DNA-glycan conjugates, wherein each of the at least two different DNA-glycan conjugates comprise:
- a glycan comprising a glycan structure of at least two carbohydrate monomers,
  - wherein each carbohydrate monomer is attached to at least one other carbohydrate monomer by a glycosidic linkage; and
- a polynucleotide covalently attached to the glycan, the polynucleotide comprising a plurality of modules, each module comprising a nucleotide string,
- wherein the plurality of modules comprises:
  - a monomer module identifying each carbohydrate monomer present in the DNA-glycan conjugate, and
  - a linkage module identifying each glycosidic linkage present between each carbohydrate monomer in the DNA-glycan conjugate,
- wherein the nucleotide sequence of the plurality of modules corresponds to the glycan structure.

12. A method for identifying a glycan-binding compound, the method comprising:
- contacting a portion of a sample suspected of comprising one or more glycan-binding compounds with the DNA-glycan conjugate of claim 1 to result in a mixture, wherein the sample is suspected of comprising a glycan-binding compound that will bind the DNA-glycan conjugate, and wherein the contacting is under conditions suitable for binding of the glycan-binding compound and the DNA-glycan conjugate to form a complex; and
- identifying any DNA-glycan conjugate bound to the glycan-binding compound.

13. The method of claim 12 wherein the sample does not comprise a glycan-binding compound that will bind a DNA-glycan conjugate present in the mixture.

14. The method of claim 12 wherein the sample comprises a biological sample.

15. The method of claim 14 wherein the biological sample comprises blood.

16. The method of claim 12 wherein the glycan-binding compound comprises a protein.

17. The method of claim 16 wherein the protein comprises an antibody.

18. The method of claim 12 wherein the identifying comprises determining the nucleotide sequence of the polynucleotide attached to the DNA-glycan conjugate bound to the glycan-binding compound.

19. A method for identifying a glycan-binding compound, the method comprising:
- contacting a sample suspected of comprising a plurality of glycan-binding compounds with a plurality of the DNA-glycan conjugates of claim 1 to result in a mixture, wherein the sample is suspected of comprising at least one glycan-binding compound that will bind a DNA-glycan conjugate of the plurality of the DNA-glycan conjugates, and wherein the contacting is under conditions suitable for binding a glycan-binding compound of the sample to a DNA-glycan conjugate of the plurality of the DNA-glycan conjugates; and
- identifying any DNA-glycan conjugates bound to glycan-binding compounds.

* * * * *

UNITED STATES PATENT AND TRADEMARK OFFICE
CERTIFICATE OF CORRECTION

PATENT NO. : 11,884,961 B2
APPLICATION NO. : 16/617756
DATED : January 30, 2024
INVENTOR(S) : Peng George Wang et al.

Page 1 of 1

It is certified that error appears in the above-identified patent and that said Letters Patent is hereby corrected as shown below:

In the Claims

In Column 215, Line 49 (Claim 2): "GpL" should read -GµL-.

In Column 216, Line 59 (Claim 7): "TECO" should read -7ECO-.

Signed and Sealed this
First Day of April, 2025

Coke Morgan Stewart
*Acting Director of the United States Patent and Trademark Office*